US 9,510,784 B2

(12) United States Patent
Benson et al.

(10) Patent No.: US 9,510,784 B2
(45) Date of Patent: Dec. 6, 2016

(54) MATTRESS HEALTH MONITORING

(71) Applicant: Blue Ocean Laboratories, Inc., North York (CA)

(72) Inventors: Ronald Stuart Benson, Toronto (CA); Ryan Cameron Denomme, Kitchener (CA)

(73) Assignee: Blue Ocean Laboratories, Inc., North York (CA)

( * ) Notice: Subject to any disclaimer, the term of this patent is extended or adjusted under 35 U.S.C. 154(b) by 0 days.

(21) Appl. No.: 14/571,916

(22) Filed: Dec. 16, 2014

(65) Prior Publication Data
US 2015/0164238 A1 Jun. 18, 2015

(30) Foreign Application Priority Data
Dec. 16, 2013 (CA) .................................... 2836431

(51) Int. Cl.
*G08B 21/00* (2006.01)
*A61F 13/42* (2006.01)
(Continued)

(52) U.S. Cl.
CPC .............. *A61B 5/4812* (2013.01); *A47C 27/15* (2013.01); *A47C 31/00* (2013.01); *A61B 5/0024* (2013.01); *A61B 5/01* (2013.01); *A61B 5/024* (2013.01); *A61B 5/02444* (2013.01); *A61B 5/0816* (2013.01); *A61B 5/11* (2013.01); *A61B 5/1115* (2013.01); *A61B 5/1116* (2013.01); *A61B 5/4266* (2013.01); *A61B 5/4806* (2013.01); *A61B 5/4809* (2013.01); *A61B 5/4815* (2013.01); *A61B 5/4818* (2013.01); *A61B 5/6892* (2013.01); *A61B 5/7264* (2013.01); *A61B 5/7278* (2013.01); *A61B 5/742* (2013.01); *A61B 5/746* (2013.01); *A61B 5/7445* (2013.01); *A61B 7/003* (2013.01); *A61G 7/05* (2013.01); *A61M 21/00* (2013.01); *G06F 19/3418* (2013.01); *G06F 19/3431* (2013.01); *A61B 5/02405* (2013.01); *A61B 2560/0242* (2013.01); *A61B 2562/0204* (2013.01); *A61B 2562/029* (2013.01); *A61B 2562/0219* (2013.01); *A61B 2562/0247* (2013.01); *A61B 2562/0252* (2013.01); *A61B 2562/0271* (2013.01); *A61M 2021/0022* (2013.01); *A61M 2021/0027* (2013.01); *A61M 2021/0044* (2013.01); *A61M 2021/0083* (2013.01); *A61M 2205/13* (2013.01); *A61M 2205/18* (2013.01); *A61M 2205/332* (2013.01); *A61M 2205/3306* (2013.01); *A61M 2205/3375* (2013.01); *A61M 2205/3553* (2013.01); *A61M 2205/3569* (2013.01);
(Continued)

(58) Field of Classification Search
CPC ..................................................... A47C 31/00
See application file for complete search history.

(56) References Cited

U.S. PATENT DOCUMENTS 7,107,642 B2 * 9/2006 Wong ................... A47C 27/082
5/713
2006/0271207 A1 * 11/2006 Shaw ................. A61G 7/05776
700/17

(Continued)

*Primary Examiner* — Travis Hunnings
*Assistant Examiner* — Pameshanand Mahase
(74) *Attorney, Agent, or Firm* — Rowand LLP

(57) ABSTRACT

Sleep systems having embedded sensors are described. In one aspect, a sleep system includes a mattress and one or more force sensors embedded within the mattress. The force sensors are positioned within the mattress to sense movement of an occupant of the mattress. The sleep system also includes one or more processors coupled with the one or more force sensors. At least one of the processors is configured to determine sleep state information for the occupant based on data obtained from one or more of the force sensors.

20 Claims, 18 Drawing Sheets

(51) Int. Cl.
*G08B 3/10* (2006.01)
*G08B 25/14* (2006.01)
*A61B 5/00* (2006.01)
*A47C 31/00* (2006.01)
*A61B 5/01* (2006.01)
*A61B 5/024* (2006.01)
*A61B 5/08* (2006.01)
*A61B 5/11* (2006.01)
*A61B 7/00* (2006.01)
*A61G 7/05* (2006.01)
*A61M 21/00* (2006.01)
*A47C 27/15* (2006.01)
*G06F 19/00* (2011.01)

(52) U.S. Cl.
CPC .............. *A61M2205/3584* (2013.01); *A61M 2205/3592* (2013.01); *A61M 2205/505* (2013.01); *A61M 2205/52* (2013.01); *A61M 2205/8206* (2013.01); *A61M 2230/06* (2013.01); *A61M 2230/42* (2013.01); *A61M 2230/50* (2013.01); *A61M 2230/62* (2013.01); *A61M 2230/63* (2013.01)

(56) References Cited

U.S. PATENT DOCUMENTS

| | | | |
|---|---|---|---|
| 2007/0157385 A1* | 7/2007 | Lemire | A61G 7/005 5/600 |
| 2009/0056020 A1* | 3/2009 | Caminade | A61B 5/447 5/600 |
| 2010/0011839 A1* | 1/2010 | Browning | G01M 3/24 73/40 |
| 2010/0250448 A1* | 9/2010 | Towe | G06Q 10/06 705/302 |
| 2011/0169481 A1* | 7/2011 | Nguyen | H01M 2/1055 324/126 |
| 2012/0108215 A1* | 5/2012 | Kameli | H04M 1/0256 455/412.2 |
| 2013/0340500 A1* | 12/2013 | Miller | G01N 25/56 73/29.02 |
| 2014/0276504 A1* | 9/2014 | Heil | A61F 13/42 604/361 |
| 2014/0333744 A1* | 11/2014 | Baym | G08B 21/245 348/77 |

* cited by examiner

Mattress Hygiene

| | |
|---|---|
| Total Usage | 4h 53min 5sec —1920 |
| Wash Sheets On | December 10 2013 |
| Refresh Mattress On | December 10 2013 |
| Replace Mattress On | December 10 2013 |
| Rotate Mattress On | December 10 2013 |

Reminders

Reminder —1902
It is time to wash your sheets!
Yes   No

Reminder —1904
It is time to refresh your mattress!
Yes   No

Reminder —1906
It is time to rotate your mattress!
Yes   No

MATTRESS HEALTH MONITORING

This application claims priority to Canadian Patent Application Number 2,836,431, the contents of which are hereby incorporated by reference.

TECHNICAL FIELD

The present disclosure relates to mattresses and, more particularly, to an intelligent sleep system.

BACKGROUND

Applications have been developed which monitor a user's sleep state. Such applications often operate on mobile devices, such as smartphones, and often require the user to place their mobile device on a mattress in order for the sleep state to be monitored. Such applications rely on an accelerometer of the mobile device for sleep state detection.

Such applications are generally limited in their functionality and convenience. More particularly, a user must remember to set their mobile device on their mattress or the application will not track their sleep state and must ensure that the mobile device is placed at a particular location of the mattress or the application will not track their sleep state.

Additionally, the hardware provided on a mobile device only allows limited information to be obtained and may suffer from accuracy issues.

Thus there exists a need for methods and systems for monitoring sleep state.

BRIEF DESCRIPTION OF THE DRAWINGS

FIG. 19 is an example display screen;
FIG. 20 is an example display screen;
and
FIG. 21 is an example display screen.

Like reference numerals are used in the drawings to denote like elements and features.

DETAILED DESCRIPTION OF EXAMPLE EMBODIMENTS

In one aspect, the present disclosure describes a sleep system. The sleep system includes a mattress and one or more force sensors embedded within the mattress. The force sensors are positioned within the mattress to sense movement of an occupant of the mattress. The sleep system also includes one or more processors coupled with the one or more force sensors. At least one of the processors is configured to determine sleep state information for the occupant based on data obtained from one or more of the force sensors.

In another aspect, a sleep system is described which includes a mattress and one or more sensors embedded within the mattress. The sleep system also includes an output interface and one or more processors coupled with the one or more sensors and the output interface. At least one of the processors is configured to determine mattress health information based on data obtained from one or more of the sensors and to generate an alert via the output interface based on the mattress health information. The sleep system also includes a memory coupled with the at least one processor.

In yet another aspect, a sleep system is described which includes one or more sensors embedded within a mattress. The sleep system also includes one or more sensors provided in a peripheral that is external to the mattress. The sleep system further includes an output interface and one or more processors receiving data from the one or more sensors embedded within the mattress and the one or more sensors provided in the peripheral. At least one of the processors is configured to determine sleep environment information based on the data from one or more of the sensors embedded within the mattress and the data from the one or more sensors provided in the peripheral. At least one of the processors is configured to generate an output on the output interface based on the sleep environment information.

In yet another aspect, a mobile device is described. The mobile device includes a communication subsystem and a processor coupled with the communication subsystem. The mobile device further includes a memory coupled with the processor. The memory is configured to receive data from a sleep system that includes one or more embedded sensors via the communication subsystem and to generate one or more display screens based on the received data.

In yet another aspect, a server is described. The server includes a communication subsystem and a processor coupled with the communication subsystem. The server further includes a memory coupled with the processor. The memory is configured to receive data from a sleep system that includes one or more embedded sensors via the communication subsystem and to generate one or more display screens based on the received data.

Other example embodiments of the present disclosure will be apparent to those of ordinary skill in the art from a review of the following detailed description in conjunction with the drawings.

Figure 1:
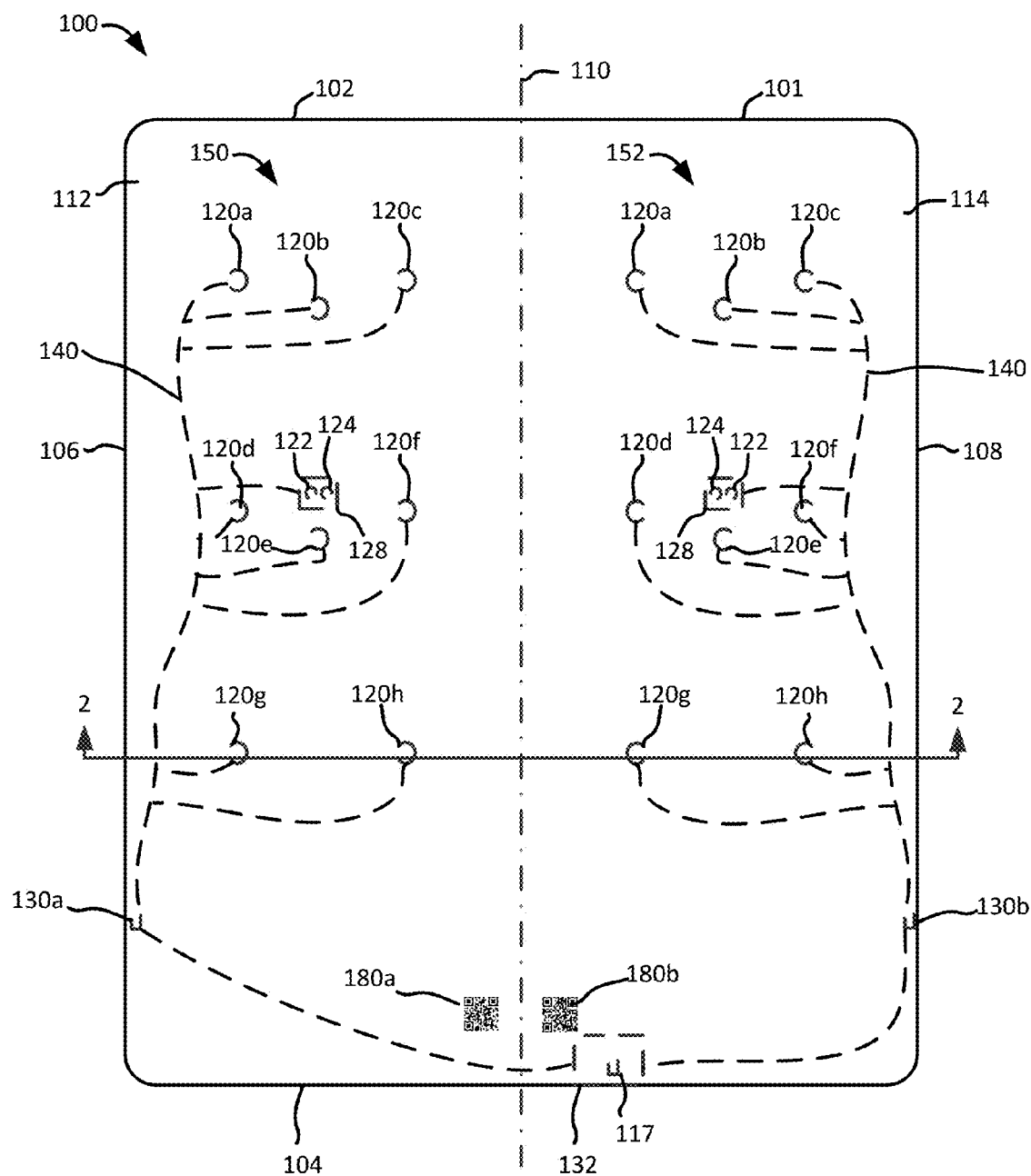
FIG. 1 is a top view of a sleep system in accordance with example embodiments of the present disclosure.

Referring now to FIG. 1, a top view of an example sleep system 100 in accordance with example embodiments of the present disclosure is illustrated. The sleep system 100 may, in at least some embodiments, be referred to as a smart mattress, an intelligent mattress, a sleep information tracking assembly or in some cases as simply a mattress.

The sleep system 100 includes a mattress 101. The mattress 101 provides support for an occupant while sleeping. The mattress 101 may, for example, be sized according to any one of a plurality of traditional mattress sizes. For example, in various embodiments the mattress 101 may be sized according to one of the following standard sizes: crib/toddler, single, twin, double, full, queen, king, wide double, Olympic queen, queen, king, super king, California king, or king long. Dimensions associated with these mattresses are readily available and will not be listed exhaustively herein. However, by way of example, in an embodiment in which the mattress is a queen sized mattress, it may have a height of 80 inches and a width of 60 inches.

The mattress 101 may be of other sizes apart from those listed above. For example, custom mattress sizes may be used in some embodiments.

The mattress 101 is generally a large pad for supporting a reclining body (the reclining body is generally referred to herein as the occupant). The interior of the mattress may be constructed of, for example, an absorbing layer such as foam and may, in some embodiments, be constructed of a coil.

Occupant Monitoring Sensors

In addition to the mattress, the sleep system 100 includes one or more sensors which may be used for monitoring an occupant of the mattress. These occupant monitoring sensors may include force sensors 120a-120h, which may be used to detect movement and positioning of an occupant, a body temperature sensor 122 used to detect a body temperature of an occupant, and/or a humidity sensor 124 used to detect humidity associated with an occupant. These sensors will be discussed in greater detail below.

Force Sensors

As noted above, the sleep system 100 may include one or more force sensors 120a-120h. The force sensors 120a-120h are embedded within the mattress 101 in at least some embodiments and are, therefore, illustrated with broken lines in the top view of FIG. 1. In at least some embodiments, one or more of the force sensors 120a-120h are positioned within the mattress to sense movement of an occupant of the mattress.

To facilitate understanding of the layout of the force sensor 120a-120h with respect to the mattress 101, the various sides of the mattress have been labelled in FIG. 1. More specifically, a top side 102 is the side of the mattress 101 which is generally nearest an occupant's head and which may also be nearest a headboard (not shown) of a bed on which the mattress rests. A bottom side 104 is opposite the top side 102 and is generally nearest an occupant's feet and which may also be nearest a footboard (not shown) of the bed.

The top side 102 and the bottom side are connected by two generally parallel sides which may be referred to as a left side 106 and a right side 108. It will be appreciated that the orientations of sides referred to above describe the mattress in one possible position and these orientations may change, for example, if the mattress is flipped or rotated.

In the example illustrated, the mattress is sized for concurrent use by two occupants (i.e. it is a two-person mattress). For example, the mattress 101 may be a queen, king, wide double, Olympic queen, queen, king, super king, California king, king long, or in some cases a full or double sized mattress. In such embodiments, a center line 110 may be defined which is located equidistant from the left side 106 and the right side 108 and which bisects the mattress 101 to divide it into two equal parts, which may generally be referred to as a left portion 112 and a right portion 114. Each of these portions may be associated with a separate sensor set 150, 152. That is, each of the left portion 112 and the right portion 114 may be associated with a separate set 150, 152 of sensors such as a separate set of force sensors 120a-120h.

Accordingly, in the example illustrated, there are two sets of sensors—a first set 150 is located on the left portion 112 of the mattress 101 to obtain data from a first occupant, who sleeps on the left portion 112 of the mattress 101, generally near the left side 106. Similarly, a second set 152 is located on the right portion 114 of the mattress 101 to obtain data from a second occupant, who sleeps on the right portion 114 of the mattress 101, generally near the right side 108.

It will be appreciated that, in other embodiments, there may be other sets of sensors included in the mattress instead of or in addition to the first set 150 and the second set 152 of sensors illustrated in FIG. 1. For example, in some embodiments, the mattress may be sized for single occupancy. By way of example, in some such embodiments the mattress may be a twin mattress which may be occupied by a single person. In such embodiments, the mattress may be equipped with a single set of sensors. Further, in other embodiments, the mattress 101 may be equipped with more than two sets of sensors. For example, the embodiment of FIG. 1 could additionally include a third set of sensors which may, for example, be disposed in the middle of the mattress. For example, the third set could be symmetric across the center line 110. This third set could, for example, be used to obtain data associated with an occupant when the mattress (which is large enough to be occupied by two people), is only occupied by a single person who generally sleeps in the center of the bed.

Each sensor set 150, 152 is used for obtaining data associated with a single occupant and, in the example illustrated, each sensor set 150, 152 includes a plurality of force sensors 120a-120b. The force sensors 120a-120b include one or more force sensors 120a, 120b, 120c that are generally oriented near an upper body of an occupant. These force sensors 120a, 120b, 120c may be referred to as upper body force sensors. These force sensors 120a, 120b, 120c are oriented to capture data in the vicinity of an occupant's head, shoulder, and/or chest region. These force sensors 120a, 120b, 120c are generally in an upper third of the mattress 101. In at least some embodiments, one or more of these upper body force sensors 120a, 120b, 120c are located approximately sixteen to nineteen inches from the top side 102 of the mattress 101. In some embodiments, the upper body force sensors 120a, 120b, 120c may be located in the range of twelve to twenty-four inches from the top side 102 of the mattress 101.

In the example embodiment illustrated, the upper body force sensors 120a, 120b, 120c include three force sensors: a first upper body force sensor 120a, a second upper body force sensor 120b, and a third upper body force sensor 120c. The first upper body force sensor 120a is the left-most upper body force sensor in the set 150, 152 and the third upper body force sensor 120c is the right-most upper body force sensor in the set 150, 152. The second upper body force sensor 120b may be located along a line that is midway between the first upper body force sensor 120a and the third upper body force sensor 120c. More particularly, the second upper body force sensor 120b may be equidistant from the first upper body force sensor 120a and the third upper body force sensor 120c. In at least some embodiments, the second upper body force sensor 120b associated with the left portion 112 of the mattress may be midway between the left side 106 and the center line 110. Similarly, the second upper body force sensor 120*b* associated with the right portion 114 of the mattress may be midway between the right side 108 and the center line 110.

The first upper body force sensor 120*a* and the third upper body force sensor 120*c* may have a separation which is in the range of eight to fifteen inches, in at least some embodiments. In one example embodiment, the first upper body force sensor 120*a* and the third upper body force sensor 120*c* may have a twelve inch separation.

In at least some embodiments, the upper body force sensors 120*a*, 120*b*, 120*c* may be located at differing distances from the top side 102 of the mattress 101. In the example illustrated, the first upper body force sensor 120*a* and the third upper body force sensor 120*c* are both located at common distances from the top side 102 of the mattress 101. The second upper body force sensor 120*b* is located at a different distance from the top side 102 than the first and third upper body force sensors 120*a*, 120*c*. More specifically, in the example illustrated, the second upper body force sensor 120*b* is relatively further from the top side 102 than are the first and third upper body force sensors 120*a*, 120*c*. By placing the upper body sensor which is in the middle of the other two sensors at a different distance from the top side 102 than the other upper body sensors, the area of coverage of the upper body sensors may be increased. That is, this arrangement may provide a larger coverage area for the upper body sensors than an embodiment where all of the upper body sensors are equidistant from the top side 102.

The example of FIG. 1 includes three upper body force sensors in each sensor set 150, 152. The sensor sets 150, 152 may include a greater or lesser number of upper body force sensors in other embodiments.

In the example illustrated, each sensor set 150, 152 also includes one or more middle body force sensors 120*d*, 120*e*, 120*f*. These middle body force sensors 120*d*, 120*e*, 120*f* are located generally nearer the middle of an occupant's body; for example, near their lower back region. The middle body force sensors 120*d*, 120*e*, 120*f* are generally in a middle third of the mattress 101. In at least some embodiments, one or more of these middle body force sensors 120*d*, 120*e*, 120*f* is located approximately thirty one to thirty three inches from the top side 102 of the mattress 101. In some embodiments, the middle body force sensors 120*d*, 120*e*, 120*f* may be located in the range of twenty nine to thirty six inches from the top side 102 of the mattress 101.

In the example embodiment illustrated, the middle body force sensors 120*d*, 120*e*, 120*f* include three force sensors: a first middle body force sensor 120*d*, a second middle body force sensor 120*e*, and a third middle body force sensor 120*f*. The first middle body force sensor 120*d* is the left-most middle body force sensor in the set 150, 152 and the third middle body force sensor 120*f* is the right-most middle body force sensor in the set 150, 152. The second middle body force sensor 120*e* may be located along a line that is midway between the first middle body force sensor 120*d* and the third middle body force sensor 120*f*. More particularly, the second middle body force sensor 120*e* may be equidistant from the first middle body force sensor 120*d* and the third middle body force sensor 120*f*. In at least some embodiments, the second middle body force sensor 120*e* associated with the left portion of the mattress may be midway between the left side 106 and the center line 110. Similarly, the second middle body force sensor 120*e* associated with the right portion 114 of the mattress may be midway between the right side 108 and the center line 110.

The first middle body force sensor 120*d* and the third middle body force sensor 120*f* may have a separation which is in the range of eight to fifteen inches, in at least some embodiments. In one example embodiment, the first middle body force sensor 120*d* and the third middle body force sensor 120*f* may have a twelve inch separation.

In at least some example embodiments, the middle body force sensors 120*d*, 120*e*, 120*f* may be located at differing distances from the top side 102 of the mattress 101. In the example illustrated, the first middle body force sensor 120*d* and the third middle body force sensor 120*f* are both located at common distances from the top side 102 of the mattress 101. The second middle body force sensor 120*e* is located at a different distance from the top side 102 than the first and third middle body force sensors 120*d*, 120*f*. More specifically, in the example illustrated, the second middle body force sensor 120*e* is relatively further from the top side 102 than are the first and third middle body force sensors 120*d*, 120*f*. As noted above in the discussion of the upper body force sensors, by placing the middle body sensor which is in located between the other two middle body force sensors at a different distance from the top side 102 than the other middle body sensors, the area of coverage of the middle body sensors may be increased. That is, this arrangement may provide a larger coverage area for the middle body sensors than an embodiment where all of the middle body sensors are equidistant from the top side 102.

The example of FIG. 1 includes three middle body force sensors in each sensor set 150, 152. The sensor sets 150, 152 may include a greater or lesser number of middle body force sensors in other embodiments.

In the example illustrated, each sensor set 150, 152 further includes one or more lower body force sensors 120*g*, 120*h*. The lower body force sensors 120*g*, 120*h* are generally located in a leg region of the mattress. The leg region of the mattress is a region that is associated with an occupant's legs. That is, the leg region is a region where a person of average size would place their legs on the mattress. The average size of a person may, for example, be region-specific to account for differing height averages in different parts of the world.

The lower body force sensors 120*g*, 120*h* are generally in a lower third of the mattress 101. In at least some embodiments, one or more of these lower body force sensors 120*g*, 120*h* is located approximately fifty to fifty five inches from the top side 102 of the mattress 101. In some embodiments, the lower body force sensors 120*g*, 120*h* may be located in the range of forty eight to fifty eight inches from the top side 102 of the mattress 101.

In the example embodiment illustrated, the lower body force sensors 120*g*, 120*h* include two force sensors: a first lower body force sensor 120*g* and a second lower body force sensor 120*h*. The first lower body force sensor 120*g* is the left-most lower body force sensor in the set 150, 152 and the second lower body force sensor 120*h* is the right-most lower body force sensor in the set 150, 152.

The first lower body force sensor 120*g* and the second lower body force sensor 120*h* may have a separation which is in the range of eight to fifteen inches, in at least some embodiments. In one example embodiment, the first lower body force sensor 120*g* and the second lower body force sensor 120*h* may have a twelve inch separation.

The example of FIG. 1 includes two lower body force sensors in each sensor set 150, 152. The sensor sets 150, 152 may include a greater or lesser number of lower body force sensors in other embodiments.

The force sensors 120a-120h may be of a variety of different forms. In at least some embodiments, the force sensors 120a-120h may include force sensitive resistors. A force sensitive resistor is a material whose resistance changes when a force is applied. In at least some embodiments, the force sensitive resistors may be used in a voltage divider circuit. By way of example, in at least some embodiments, the force sensitive resistor may be a model 402 force sensitive resistor from Interlink Electronics™. Other force sensors could be pressure sensitive foams (such as a polyurthethane foam doped with carbon) or conductive threads/fabrics that change resistance with deformation, as an example.

Furthermore, in other embodiments, other sensors could be used to sense movement and position of an occupant instead of or in addition to the force sensors 120a-120h. For example, in some embodiments, one or more accelerometers could be embedded into the mattress.

The layout of the sensors described with reference to FIG. 1 may, in at least some embodiments, be varied from that described and claimed above to account for variations in the sizes of occupants. For example, the layout may be varied to account for regional-based differences, age-based differences and/or gender-based differences. For example, in one embodiment, a sensor set 150, 152 may be arranged to accommodate a female of average size. In one embodiment, a sensor set 150, 152 may be arranged to accommodate a male of average size. In some embodiments, the arrangement of sensors may be customized for an individual. For example, measurements of an individual may be obtained and the force sensors 120a-120h arranged in accordance with the obtained measurements. That is, a processor associated with a manufacturing system used to manufacture the sleep system may determine sensor locations based on the measurements. The measurements may, for example, be obtained by performing an image-based analysis on a photograph of the individual. In other embodiments, the measurements may be manually obtained an input into the manufacturing system using an input device.

Figure 2:
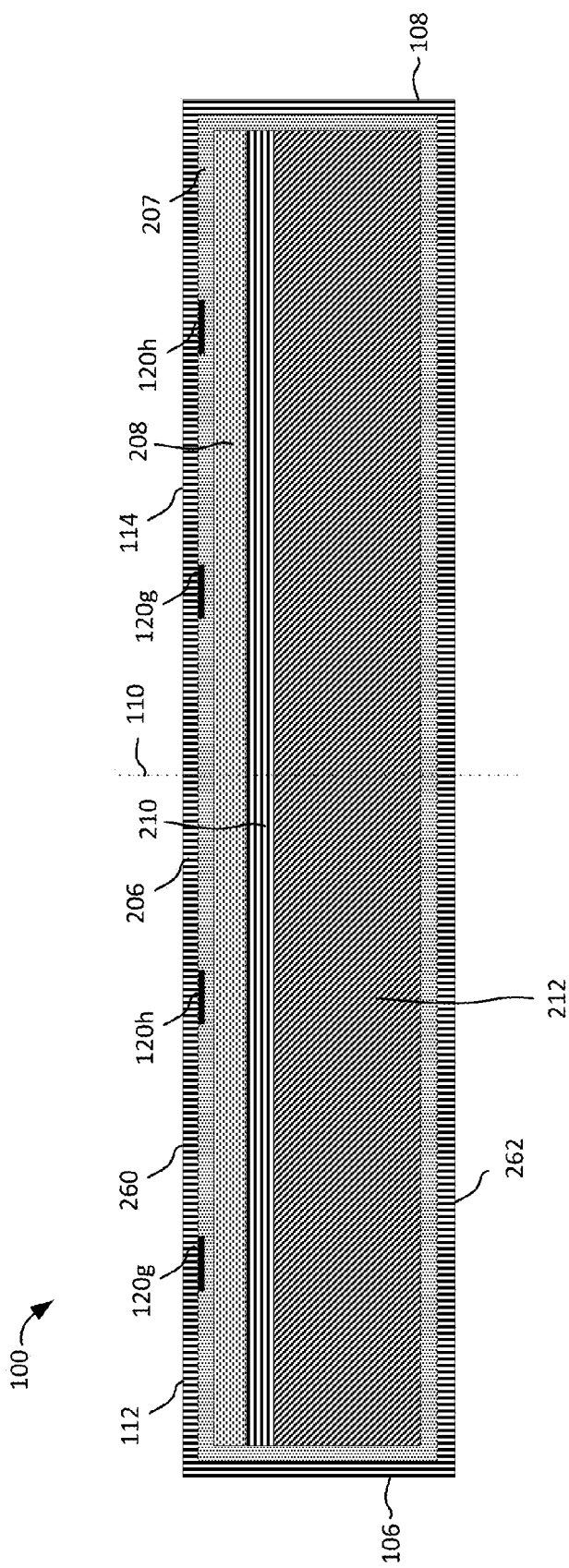
FIG. 2 is a cross section of the sleep system of FIG. 1 taken along line 2-2 of FIG. 1.

Referring briefly to FIG. 2, a cross-section of the mattress 101 taken along line 2-2 of FIG. 1 is illustrated. The cross section of the mattress illustrates the embedding of sensors within the mattress. As illustrated in FIG. 2, the mattress may be composed of one or more internal supporting layers which generally provide support to an occupant of the mattress. The internal support layers may include foam layers and/or coils. Other supporting materials may be used in other embodiments. In the example illustrated, the mattress 101 is constructed of three foam layers 212, 210, 208. A lower foam layer 212 is the thickest foam layer in the example. This lower foam layer 212 supports a middle foam layer 210. The middle foam layer 210 may support an upper foam layer 208. The various foam layers may have different softness ratings. That is, the firmness of the foam layers may differ and some of the foam layers may have different indentation force deflection (IFD) ratings than other of the foam layers. For example, the upper foam layer 208 may be softer than the lower foam layer 212 to provide a pillow-top effect.

The supporting layer(s) of the mattress may be enclosed by a sock layer 207. The sock layer 207 is an internal casing and is typically a fabric. The sock layer 207 surrounds the supporting layers and is, itself, surrounded by a ticking layer 206 (which may be referred to as the "ticking").

The ticking layer 206 is the outermost layer of the mattress 101. That is, the ticking is the final layer of the mattress which encases the other layers of the mattress. The ticking is typically constructed of a durable fabric.

As illustrated in FIG. 2, in at least some embodiments, sensors, such as the force sensors 120a-120h described above (and/or a body temperature sensor 122 and/or a humidity sensor 124 which will be described in greater detail below) may be embedded within the mattress. That is, these sensors may be disposed internally within the mattress 101. In some embodiments, these sensors may be attached to an internal side of the ticking layer 206. In other embodiments, these sensors may be attached to the sock layer 207 of the mattress 101. In some embodiments, these sensors may be attached to the ticking layer 206 or the sock layer 207 using an adhesive, such as a glue. Accordingly, in at least some embodiments, the sensing components of the sleep system 100 is non-contact; that is, the user does not directly contact the sensors.

To facilitate an understanding of mattress flipping and rotation, which will be discussed below with reference to FIG. 10, two additional sides of the mattress will be described—an upper side 260 and a lower side 262. The upper side 260 is the side that supports an occupant and the lower side 262 supports the mattress itself. The lower side may rest on a floor, frame or box spring.

Temperature Sensor(s)

Referring again to FIG. 1, the sensor sets 150, 152 may include other sensors instead of or in addition to the force sensors described above. For example, in at least some embodiments, a body temperature sensor 122 may be included in one or more of the sensor sets 150, 152. The body temperature sensor 122, which is embedded into the mattress, is positioned to obtain temperature readings associated with an occupant of the mattress. That is, the body temperature sensor 122 detects an occupant's body temperature.

In order to accurately measure an occupant's body temperature, the body temperature sensor 122 is placed in a region of the mattress in which an occupant frequently sleeps. In at least some embodiments, the body temperature sensor 122 may be located in a middle body region of the mattress 101. The middle body region of the mattress 101 is a region of the mattress that is located generally nearer the middle of an occupant's body; for example, near their lower back region. The body temperature sensor 122 may generally be in a middle third of the mattress 101. In at least some embodiments, the body temperature sensor 122 is located approximately thirty one to thirty three inches from the top side 102 of the mattress 101. In some embodiments, the body temperature sensor 122 may be located in the range of twenty nine to thirty six inches from the top side 102 of the mattress 101.

The body temperature sensor 122 may, in at least some embodiments, be located at or near the middle of the left portion 112 and/or the right portion 114 of the mattress 101. In at least some embodiments, the body temperature sensor 122 associated with the left portion of the mattress may be approximately midway (i.e. within a two inch variation) between the left side 106 and the center line 110. Similarly, the body temperature sensor 122 associated with the right portion 114 of the mattress may be approximately midway (i.e. within a two inch variation) between the right side 108 and the center line 110. In some embodiments, such as embodiments where the mattress is sized for a single occupant, a body temperature sensor may be located near the center line 110 (i.e. within 2 inches of the center line 110).

The body temperature sensor 122 may be of a variety of different types. In one embodiment, the body temperature sensor includes a thermistor. A thermistor is a resistor whose resistance is highly temperature-dependent. That is, the resistance of the thermistor changes greatly due to changes in temperature. By way of example, in at least one embodiment, the temperature sensor 122 may be a model MCP9700 or TC1047 model thermistor from Microchip™. It will be appreciated that other temperature sensors may also be used.

In at least some embodiments, the body temperature sensor 122 may be located to be near at least one force sensor 120a-120h. For example, the body temperature sensor 122 may be placed in an area of the mattress which is defined by the middle body force sensors 120d, 120e, 120f. In at least some embodiments, the body temperature sensor 122 may be within five inches of at least one force sensor. In the example illustrated, the body temperature sensor 122 is located in proximity to the second middle body force sensor 120e. That is, the body temperature sensor 122 and the second middle body force sensor 120e are within five inches of one another.

In at least some embodiments, before a processor (which will be described in greater detail below) utilizes a temperature reading obtained from the temperature sensor 122 for an operation that relies upon an occupant's body temperature, it will determine whether the body temperature sensor 122 has, in fact, been engaged by an occupant's body when determining whether a temperature reading represents a body temperature, the processor may analyze the temperature reading. If the temperature is too low (i.e. if it is less than a predetermined threshold), then the processor may determine that the temperature sensor is not engaged and that the temperature being reported by the temperature sensor is a room temperature and not a body temperature. In at least some embodiments in which a force sensor 120a-120h is located near the body temperature sensor 122, data from the force sensor may be used to determine whether the body temperature sensor 122 is likely engaged by an occupant's body. For example, if the force being reported by the force sensor 120a-120h nearest the body temperature sensor 122 exceeds a predetermined threshold, then the processor may determine that the body temperature sensor 122 is likely engaged and is likely reporting a body temperature. If, however, the force is less than a threshold, then the processor may determine that the body temperature sensor 122 is not reporting a body temperature.

In will be appreciated that, in at least some embodiments, a plurality of temperature sensors 122 may be embedded into the mattress at a plurality of different locations. For example, a first temperature sensor may be located at a first location and a second temperature sensor may be located at a second location.

Furthermore, as will be discussed in greater detail below with reference to FIG. 3, in at least some embodiments, the sleep system 100 may include a room temperature sensor which is located to obtain temperature readings associated with the room where the sleep system 100 is located so that the temperature of a sleep environment may be assessed.

Humidity Sensor(s)

In at least some embodiments, the sensor sets 150, 152 may also include one or more humidity sensors 124 which are embedded into the mattress 101. In some embodiments, at least one of the humidity sensors 124 may be a body humidity sensor 124. The body humidity sensor 124 may be used to obtain humidity readings which indicate an amount of perspiration of the occupant. Accordingly, the body humidity sensor 124 may, in at least some embodiments, be referred to as a perspiration sensor or a sweat sensor.

To detect humidity caused by an occupant, the body humidity sensor 124 may be placed at a location where it is aligned with an occupant's typical or expected sleeping position. For example, the humidity sensor 124 may be placed in a region of the mattress in which an occupant frequently sleeps. In at least some embodiments, the humidity sensor 124 may be located in the middle body region of the mattress 101. The humidity sensor 124 may generally be in a middle third of the mattress 101. In at least some embodiments, the humidity sensor 124 is located approximately thirty one to thirty three inches from the top side 102 of the mattress 101. In some embodiments, the humidity sensor 124 may be located in the range of twenty nine to thirty six inches from the top side 102 of the mattress 101.

The humidity sensor 124 may, in at least some embodiments, be located at or near the middle of the left portion 112 and/or the right portion 114 of the mattress 101. In at least some embodiments, the humidity sensor 124 associated with the left portion of the mattress may be approximately midway (i.e. within a two inch variation) between the left side 106 and the center line 110. Similarly, a humidity sensor 124 associated with the right portion 114 of the mattress may be approximately midway (i.e. within a two inch variation) between the right side 108 and the center line 110. In some embodiments, such as embodiments where the mattress is sized for a single occupant, a humidity sensor 124 may be located near the center line 110 (i.e. within 2 inches of the center line 110).

The humidity sensor 124 may be of a variety of different types. By way of example, in at least one embodiment, the humidity sensor 124 may be a Honeywell™ model HIH-5030 or model HCH-1000 humidity sensor.

In at least some embodiments, the humidity sensor 124 may be located to be near at least one force sensor 120a-120h. For example, in at least some embodiments, the humidity sensor 124 may be placed in an area of the mattress which is defined by the middle body force sensors 120d, 120e, 120f. In at least some embodiments, the humidity sensor 124 may be within five inches of at least one force sensor. In the example illustrated, the humidity sensor 124 is located in proximity to the second middle body force sensor 120e. That is, the humidity sensor 124 and the second middle module force sensor 120e are within five inches of one another.

In at least some embodiments, before a processor interprets a reading from the humidity sensor as a perspiration reading (and/or incontinence reading) for an occupant of the mattress, it will determine whether the humidity sensor 124 has, in fact, been engaged by an occupant's body. In at least some embodiments in which a force sensor 120a-120h is located near the humidity sensor 124, data from the force sensor may be used to determine whether the humidity sensor 124 is likely engaged by an occupant's body. For example, if the force being reported by the force sensor 120a-120h nearest the humidity sensor 124 exceeds a predetermined threshold, then the processor may determine that the humidity sensor 124 is likely engaged and is likely reporting a perspiration reading (i.e. a reading representing humidity caused by a user perspiring). If, however, the force is less than a threshold, then the processor may determine that the humidity sensor 124 is not reporting a perspiration reading (i.e. that the humidity being reported is not caused by a user perspiring) or incontinence reading.

As will be described below with reference to FIG. 10, the humidity sensor 124 may also, in at least some embodiments, be used to assess the health of the mattress itself. More particularly, a processor may monitor the humidity level associated with the mattress and may generate an alert if the humidity level exceeds a threshold and/or if the humidity level exceeds a threshold for at least a predetermined period of time. In embodiments in which the humidity sensor 124 is used to assess the mattress health, the humidity sensor 124 may have a different location than that noted above. More particularly, in such embodiments the humidity sensor 124 may not be located in a location that is typically associated with an occupant. However, in other embodiments, the humidity sensor 124 used for assessing mattress health may be located in a location associated with an occupant.

In some embodiments, a humidity sensor 124 may be located in a region associated with occupant's middle body and, more particularly, to a region which would typically be near the occupant's urethra. In at least some such embodiments, the humidity sensor 124 could be used to detect a bedwetting condition (which may also be referred to as an incontinence condition). That is, if the humidity level reported by the humidity sensor exceeds a predetermined threshold, then an associated processor may determine that an occupant has urinated in bed.

In will be appreciated that, in at least some embodiments, a plurality of humidity sensors 124 may be embedded into the mattress at a plurality of different locations. For example, a first humidity sensor may be located at a location associated with a occupant's genitals and may be used to detect bedwetting and a second humidity sensor may be located at a location in which it would be likely to be engaged by an occupant's back so that it could be used to detect excessive perspiration from the occupant's back. Similarly, in some embodiments, another humidity sensor could be located at another location where it is unlikely to be engaged by the occupant. This humidity sensor could be used for detecting a humidity level associated with mattress health.

Furthermore, as will be discussed in greater detail below with reference to FIG. 3, in at least some embodiments, the sleep system 100 may include a room humidity sensor 330 which is located to obtain humidity readings associated with the room where the sleep system 100 is located so that the humidity of a sleep environment may be assessed.

In at least some embodiments, the body temperature sensor 122 and the humidity sensor 124 embedded into the mattress 101 are provided on a common printed circuit board 128 and/or a flexible circuit board, which may provide further comfort for the occupant. The printed circuit board 128 may, for example, facilitate connection of the sensors to one or more transport mediums 140 (e.g. wires) which may connect the sensors to one or more processors.

Transport Mediums

As illustrated in FIG. 1, the various sensors (such as force sensors 120a-120h, temperature sensors 122 and/or humidity sensors 124) that are embedded into the mattress 101 may be connected to one or more processors 130a, 130b, 117 using one or more transport mediums 140, which are embedded into the mattress 101. That is, the transport mediums 140 are internally run within the mattress so that an occupant cannot access the transport mediums 140.

In the example illustrated in FIG. 1, only a single transport medium 140 on each side of the mattress has been labelled to avoid clutter. However, it will be appreciated that transport mediums may connect each sensor to at least one processor and, in at least some embodiments, a power source 312 (FIG. 3).

The transport mediums 140 are conductive mediums that may be used to transmit an electrical signal from the sensors to the processor(s) 130a, 130b, 117.

The transport mediums 140 may, in at least some embodiments, include wires. In some embodiments, at least some of the wires which run through a region of the mattress where an occupant might be expected to contact during sleep are small gauge wires (for example, up to 20 American Wire Gauge (AGW)) to ensure that the occupant cannot feel the wires.

In one embodiment, the transport mediums 140 may include conductive thread, fabric, or ink/paint. Conductive thread or fabric is thread or fabric that is composed of a material which conducts an electrical signal. The conductive thread provides an electrical connection between one or more sensors (such as a force sensor 120a-120h) to the processor(s) 130a, 130b, 117. The conductive thread may be sewn into a layer of the mattress 101, such as a sock layer 207 or a ticking layer 206 of the mattress 101 (which are described above with reference to FIG. 2). In at least some embodiments, a conductive thread may be used which is a silver-plated nylon yarn.

In FIG. 1, it appears that a single transport medium connects to each sensor. In practice, a plurality of transport mediums 140 may connect to each sensor. For example, one or more transport mediums may connect a sensor to a power source 312 (FIG. 3) and another one or more transport mediums may be used for transmitting data.

Processors

The sleep system 100 includes one or more processors 130a, 130b, 117. The processors 130a, 130b, 117 may be used to analyze data obtained from sensors associated with the sleep system 100, such as the force sensors 120a-120h, the temperature sensor(s) 122, the humidity sensor(s) 124, a microphone 334 (FIG. 3), a light sensor 336 (FIG. 3), a dust sensor 338 (FIG. 3), a room humidity sensor 330 (FIG. 3) and/or a room temperature sensor 332 (FIG. 3).

In the embodiment illustrated, the sleep system includes a plurality of processors 130a, 130b, 117. More specifically, each sensor set 150, 152 is associated with a separate processor, which are microcontrollers 130a, 130b, in the example. In the example embodiment illustrated, the microcontrollers 130a, 130b are both electrically connected to a main processor 117.

The microcontrollers 130a, 130b may include small processors which are capable of doing simple calculations and data manipulation. Tasks that are more processing-intensive may be performed by the main processor 117 and/or by another processor which may be provided on a remote server or a mobile device.

Each microcontroller 130a, 130b may be connected to a plurality of sensors via one or more transport mediums 140. These transport mediums 140 may be of the type described above. For example, in at least some embodiments, the microcontrollers 130a, 130b may connect to the sensors using conductive thread.

In the example illustrated, each microcontroller 130a, 130b is connected to all of the sensors in one of the sensor sets 150, 152. That is, a first microcontroller 130a is connected to the sensors in the first set 150, which is the set that generally provides coverage on the left portion 112 of the mattress 101 and a second microcontroller 130b is connected to the sensors in the second set 152, which is the set that generally provides coverage on the right portion 114 of the mattress 101. More particularly, the first microcontroller 130a is connected to force sensors 120a-120h on the left portion 112 of the mattress 101 and, in at least some embodiments, a body temperature sensor 122 and/or a humidity sensor 124 associated with the left portion 112 of the mattress 101. Similarly, the second microcontroller 130b is connected to force sensors 120a-120h on the right portion 114 of the mattress 101 and, in at least some embodiments, a body temperature sensor 122 and/or a humidity sensor 124 associated with the right portion 114 of the mattress 101. Since each microcontroller 130a, 130b services a set of sensors associated with a particular side of the mattress in the example, the combination of a microcontroller 130a and the sensors which that microcontroller 130a services may be referred to as a sensing array or a sensor block. Accordingly, the first microcontroller 130a and the first sensor set 150 may be referred to as a first sensing array or a left occupant sensing array 302 (FIG. 3), in at least some embodiments. Similarly, the second microcontroller 130b and the second sensor set 152 may be referred to as a second sensing array or a right occupant sensing array 304 (FIG. 3), in at least some embodiments.

The microcontrollers 130a, 130b may connect to the main processor 117 using one or more transport mediums. In some embodiments, these transport mediums may be conductive thread. However, in other embodiments, these transport mediums may be wires. Thus, the main processor is coupled with the sensors via the microprocessors 130a, 130b, in at least some embodiments.

In at least some embodiments, the microcontrollers 130a, 130b may communicate with the main processor 117 over more or more buses, which are provided over the transport mediums connecting the microcontrollers 130a, 130b to the main processor 117. In some embodiments, the microcontrollers 130a, 130b may communicate with the main processor 117 over and Inter-Integrated Circuit ($I^2C$) bus. The $I^2C$ bus may use two bidirectional open-drain lines for communications, including a serial data line (SDA) and a serial clock (SCL). These lines may be pulled up with resistors, which may be 4.7 kilo-ohm resistors, in some embodiments.

Depending on the type of sensors and processors used, the processors may interface with one or more analog to digital converters (ADC) and/or one or more digital to analog converters (DAC), which may connect to one or more of the processors 130a, 130b, 117. The ADC may, for example, be used to convert an analog signal generated by a sensor (such as a force sensor 120a-120h) into a digital signal which may be input to a processor (such as the microcontrollers 130a, 130b and/or the main processor 117).

The main processor 117 may act as a master controller and the microcontrollers 130a, 130b may act as slaves. In at least some embodiments, the slave microcontrollers 130a, 130b are configured to include identifying information in communications which are sent by the microcontrollers 130a, 130b over the bus to the main processor 117. For example, a first byte of data sent to the main processor 117 from the microcontrollers 130a, 130b may be used to identify the microcontroller 130a, 130b which sent that data. Such identification allows for easy expansion of the system to incorporate more sensors if needed.

The microprocessors 130a, 130b may be configured to periodically collect data from the sensors in an associated sensor set 150, 152. The microprocessor(s) 130a, 130b may collect data from different types of sensors at different rates. For example, to perform some of the analysis discussed below, a large resolution in the time domain may be required for force sensor data. Accordingly, in some embodiments, data from force sensors 120a-120h may be collected at a period that is in the range of 80 to 120 ms. In some embodiments, data from the force sensors 120a-120h may be collected every 100 ms. However, other sensors, such as the body temperature sensor 122 and/or the humidity sensor 124 may not require as high a resolution in the time domain. Thus, the microprocessor(s) 130a, 130b may sample the body temperature sensor 122 and/or the humidity sensor 124 at a lower rate than the force sensors 120a-120h. For example, in some embodiments, data from the body temperature sensor 122 and/or the humidity sensor 124 may be collected at a period that is in the range of 2500 to 4500 ms.

While FIG. 1 illustrates an embodiment in which three processors are utilized (including a main processor 117 and two microcontrollers 130a, 130b), in other embodiments a greater or lesser number of processors may be used. For example, in some embodiments, the main processor 117 may perform some data calculations and manipulations and may output the data to a connected peripheral which contains a further processor which performs additional analysis on the data.

The microcontroller(s) 130a, 130b are embedded into the mattress 101 in the illustrated embodiment. For example, the microcontroller(s) 130a, 130b may be attached to a sock layer 207 of the mattress 101 or an interior side of the ticking layer 206 of the mattress. These layers are described in greater detail above with reference to FIG. 2. The microcontroller(s) are disposed internally within the mattress so that they cannot be viewed by the occupant of the mattress 101. The microcontrollers may, in at least some embodiments, be provided on PCBs or flexible PCBs.

Furthermore, in some embodiments, some of the analysis described herein may be performed using a processor that is remote from the mattress 101. For example, as will be described below with reference to FIG. 3, the sleep system 100 may be equipped with a communication subsystem, such as a wireless communication subsystem 370. The wireless communication subsystem may, for example, be a WiFi connection and/or a Bluetooth™ connection. This connection may be used for sending data to a remote server or computer, which contains a processor. By way of example, in some embodiments, data may be collected and periodically sent to the remote server or computer for analysis. For example, the wireless communication subsystem may provide a connection between the main processor 117 and a mobile device 1200 (FIG. 12) such as a smartphone or tablet computer (or a computer of another type). The mobile device 1200 may include a processor 1217 (FIG. 12) which may be associated with computer executable instructions which configure the processor to perform at least some of the analysis described below. Further, in some embodiments, data may be sent over the Internet to a server. This data may be sent directly from the main processor 117 to the remote server (i.e. via the wireless communication subsystem 370), or may be sent by engaging a mobile device 1200 or other computer which may have Internet connectivity and which may forward the data to the remote server. Thus, the remote server may include a processor which may be associated with computer executable instructions which configure the processor to perform at least some of the analysis described below.

The main processor 117 is, in some embodiments, provided internally within the mattress 101. In the example illustrated, the main processor 117 is provided in a central processing unit 132 which is integrated with the mattress 101. The central processing unit 132 may be provided at one end of the mattress 101. In the example illustrated, the central processing unit 132 is provided at a bottom side 104 of the mattress 101. However, the central processing unit 132 may be provided at different locations in other embodiments.

By way of further example, in some embodiments the central processing unit 132, or a portion thereof, may be provided at a location that is external to the mattress 101. For example, the central processing unit 132 (or a portion thereof) may be provided as a peripheral which connects to other components of the sleep system 100 (such as the microcontrollers 130a, 130b) either via a wired or wireless connection. The peripheral may, for example, be configured to rest on a table, such as a night table, located near the mattress 101.

Machine-Readable Code(s)

Figure 12:
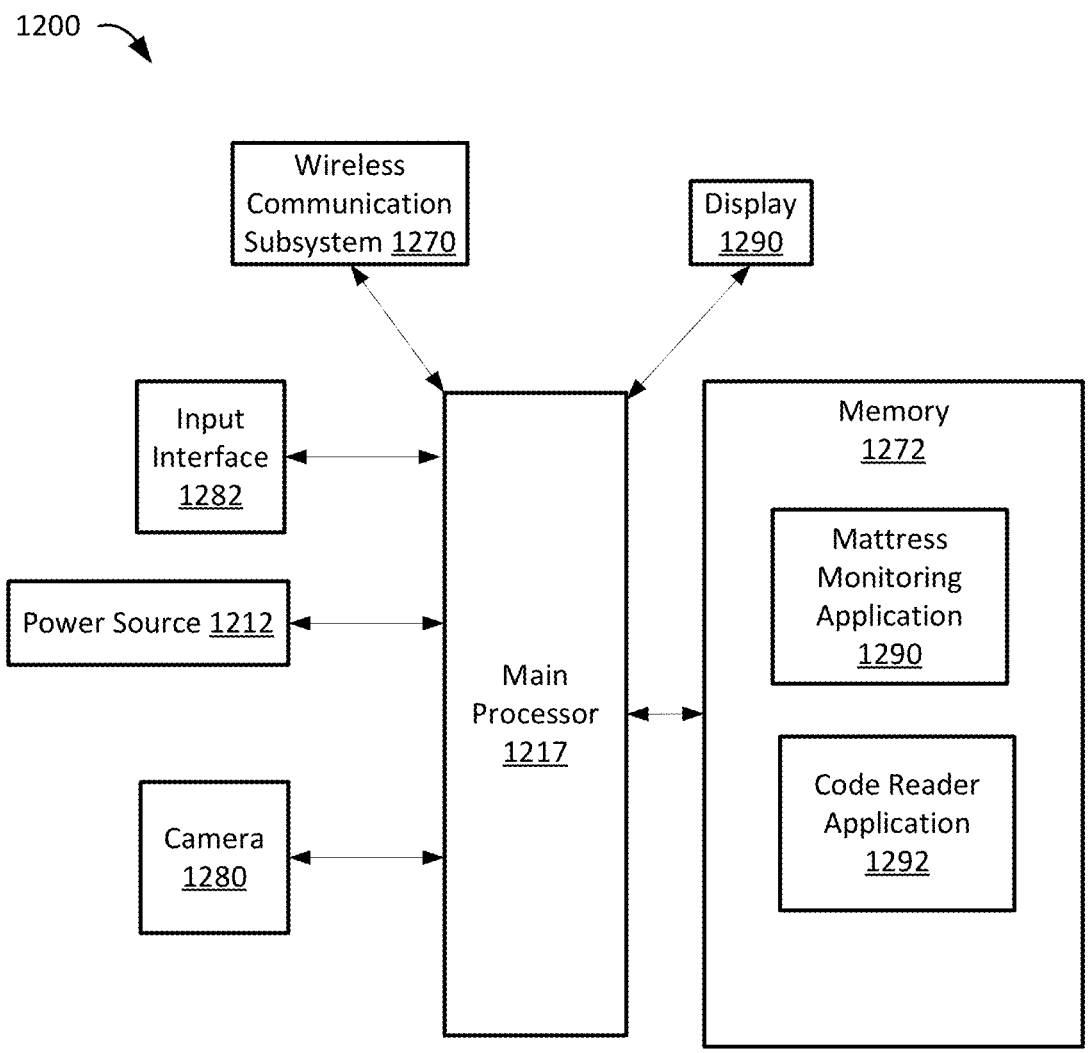
FIG. 12 is a block diagram of a mobile device in accordance with example embodiments of the present disclosure.

As will be discussed in greater detail below, in some embodiments, the sleep system 100 may be configured to communicate with an associated mobile device 1200 (FIG. 12). The mobile device 1200 may, for example, be a smartphone or tablet computer.

In at least some embodiments, to facilitate download of a mattress monitoring application 1290 (FIG. 12) onto the mobile device and/or setup of the mattress monitoring application 1290 on the mobile device, one or more machine readable codes 180a, 180b may be affixed to the mattress 101. This code may, for example, be a quick response (QR) code. The machine-readable code may, in at least some embodiments be unique to the mattress. That is, the machine-readable code may uniquely identify the mattress 101 from other mattresses. In at least some embodiments, the machine-readable code 180a, 180b is readable by the mobile device 1200 to associate the mobile device with the mattress. In some embodiments, this may allow the mobile device to communicate with a server and to register the mattress in a user profile maintained by the server.

In some embodiments, both the left and right portions 112, 114 of the mattress 101 may include separate machine-readable codes 180a, 180b which may be used to associate a mobile device 1200 with a specific side of the mattress. Each of these machine-readable codes is associated with a separate portion 112, 114 of the mattress 101. For example, a first code 180a may be located at a left portion 112 of the mattress and associated with the left portion 112 and a second code 180b may be located at a right portion 114 of the mattress and associated with the right portion 114. A user of a mobile device 1200 (FIG. 12) may use a camera 1280 (FIG. 12) on that device to scan the code 180a, 180b. The codes 180a, 180b uniquely identify the mattress from other mattresses, and each of the codes uniquely identifies the side of the mattress associated with that code. For example, the first code 180a may identify the left side and the second code 180b may identify the right side.

In such embodiments, the code 180a, 180b may be used by the mobile device 1200 to associate the mobile device 1200 with a specific side of the mattress. That is, an occupant who sleeps on the left portion 112 may scan the code 180a associated with the left portion. In at least some embodiments, by doing so the mobile device 1200 will then obtain and/or display information obtained from the sleep system about the left portion of the mattress. For example, sleep state information and/or raw data generated from a first sensor set 150 located at the left portion may be retrieved by the mobile device which has scanned the code 180a on the left portion, but sleep state information and/or raw data generated from the second sensor set 152 located at the right portion may not be retrieved by the mobile device which has scanned the code 180a on the left portion. Accordingly, in at least some embodiments, a mobile device 1200 may only retrieve and/or display information associated with a portion of the bed for which it has scanned the associated code 180a, 180b.

In at least some embodiments, the codes may have encoded therein a location where the mobile device 1200 (FIG. 12) may download the mattress monitoring application 1290. This location may, for example, be a server location such as the location of a file on an application store, such as Google Play™ or Apple™ app store.

In some embodiments, the sleep system 100 may be equipped with one or more wireless tags which store the machine readable code(s) referred to above. For example, in some embodiments, a near field communication (NFC) tag or radio frequency identification (RFID) tag may be provided on the sleep system 100. The tag may be read by a mobile device 1200 (FIG. 12) to cause the mobile device to perform one or more of the functions described above (e.g. to cause the mobile device to download the mattress monitoring application 1290 (FIG. 12) onto the mobile device and/or setup the mattress monitoring application 1290, and/or to associate the mobile device with a specific side of the mattress). In at least some embodiments, the sleep system 100 may include a plurality of tags and each tag may be physically located near a separate side of the mattress. In such embodiments, when the mobile device 1200 scans the tag, it may associate the mobile device 1200 with the side where the tag was located.

Block Diagram of Sleep System

Figure 3:
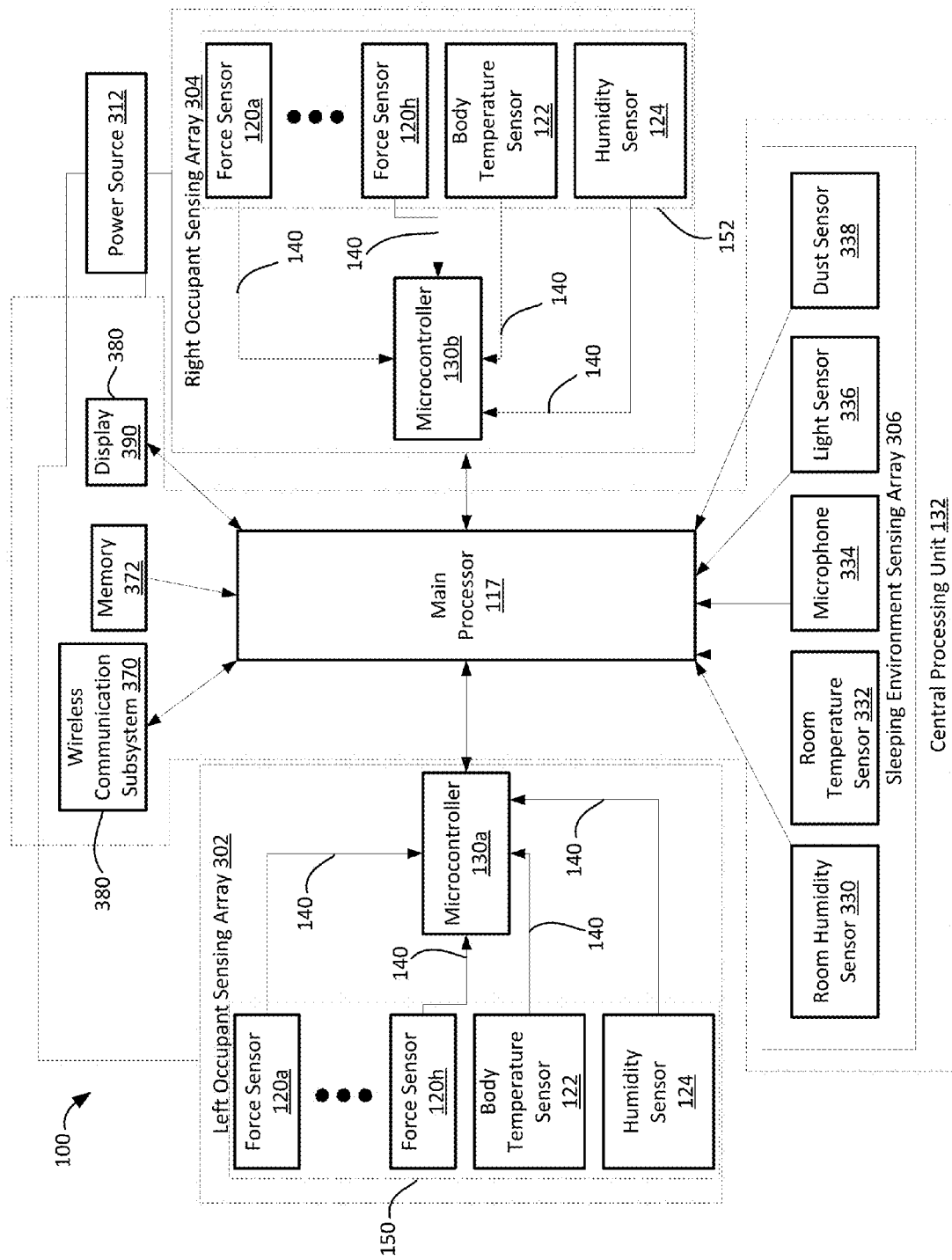
FIG. 3 is a block diagram of an example sleep system.

Referring now to FIG. 3, a block diagram of the sleep system 100 is illustrated. The block diagram includes components discussed above.

As illustrated, the sleep system 100 includes a plurality of occupant monitoring sensors. The occupant monitoring sensors include force sensors 120a-120h, a body temperature sensor 122 and a humidity sensor 124. In the example illustrated, the sensors are divided into two sensor sets 150, 152. A first sensor set 150 is associated with a left portion 112 of the mattress 101 and is included in a left occupant sensing array 302. A right sensor set 152 is associated with a right portion 114 of the mattress and is included in a right occupant sensing array 304. Each of the sensing arrays 302, 304 in the example includes an associated microcontroller 130a, 130b, which receives sensor data from the sensors in the sensing array 302, 304 associated with the microcontroller 130a, 130b.

In the example, each sensor set 150, 152 includes a plurality of force sensors 120a-120h, a body temperature sensor 122 and a humidity sensor 124. The sensor sets 150, 152 may include other types of sensors instead of or in addition to the sensors described above. Further, in some embodiments, one or more of the sensors illustrated in FIG. 3 may be omitted. The sensors may, for example, generate an electric signal which includes sensor data and may provide the electric signal to a processor, such as the microcontroller 130a, 130b and/or the main processor 117.

The sensors in the sensor sets 150, 152 may be arranged in the manner described above with reference to FIGS. 1 and 2.

As noted above, transport mediums 140 may connect the sensors in a sensing array 302, 304 to a processor, such as an associated microcontroller 130a, 130b.

The microcontrollers 130a, 130b include a processor and associated memory. The microcontrollers 130a, 130b are coupled with a main processor 117. The main processor is coupled with a memory 372. The memory associated with the microcontrollers 130a, 130b and the memory associated with the main processor 117 may store processor-executable instructions which configure the associated processor to perform a method, such as one or more of the methods described below.

The memory 372 associated with the main processor 117 is, in the embodiment illustrated, external to the main processor 117. In other embodiments, the memory, the memory may be internal memory of the main processor 117.

The memory 372 associated with the main processor 117 and the memories associated with the microcontrollers 130a, 130b may take a variety of forms and may include a plurality of different types of memories. For example, in some embodiments, flash memory may be utilized. In some embodiments, random access memory (RAM) may be used. It will be appreciated that any one of the processors may be coupled with memory of a plurality of types. For example, the main processor 117 may use both flash memory and RAM.

A memory 372 coupled with a processor (such as the main processor 117) may be used, in at least some embodiments, for storing data obtained or derived from the sensors. For example, information derived from the sensor data may be stored in the memory 372 for further analysis or reporting. For example, various scores that may be determined in accordance with some embodiments described below may be stored in the memory 372. These scores may, for example, include a sleep score, a sleep environment score, a mattress health score, etc. Further, in at least some embodiments, a processor may use the memory 372 to store sleep state information for an occupant of the mattress 101. The sleep state information may be of various types. For example, in at least some embodiments, the processor may store information regarding times associated with various sleep stages of the occupant. For example, the time when a user fell asleep and/or woke up may be recorded in the memory. Similarly, in at least some embodiments, sleep disorder information for an occupant may be stored in the memory 372. This information may indicate whether a user has or is likely to have a sleep disorder. The sleep disorder may, for example, include any one or combination of: insomnia, narcolepsy, sleep apnea, bruxism, delayed sleep phase syndrome, advanced sleep phase syndrome, periodic limb movement disorder, sleep walking, sleep talking, bed wetting, etc. Techniques which may be used to allow one or more of the processors 117 to detect such conditions are described in greater detail below with reference to FIG. 9.

Furthermore, in some embodiments, the processor(s) 117 may store in memory 372 information about the health of the mattress. This information may, for example, include, for example, mattress health information. Mattress health information is information about the health of the mattress 101. The mattress health information may, for example, quantify the usage of the mattress over its lifetime (i.e. since manufacture of the mattress), quantify the usage of the mattress since a maintenance event (such as the usage since a last flip or rotation of the mattress, the usage since the last vacuuming of the mattress, the usage since the last change of bedding, the usage since the last deodorizing and/or disinfecting of the mattress), and/or may be based on the humidity level associated with the mattress. Techniques which may be used to allow one or more of the processors to detect such conditions are described in greater detail below with reference to FIG. 10.

Furthermore, in some embodiments, the processor(s) may store in memory information about a sleeping environment associated with the mattress 101. The sleeping environment information may, for example, include a measure of a humidity level in the room where the mattress is located, or a measure of a temperature level in the room where the mattress is located. Other sleeping environment information may be stored in the memory in other embodiments.

In some embodiments, raw sensor data may be stored in the memory 372 for further analysis or reporting. This raw sensor data may, for example, include force sensor data (i.e. data obtained from one or more of the force sensors 120a-120h), body temperature sensor data (i.e. data obtained from a body temperature sensors 122), humidity sensor data (i.e. data obtained from a humidity sensors 124), dust sensor data (i.e. data obtained from a dust sensor), audio data (which may be data obtained from a microphone 334), light sensor data (i.e. data obtained from a light sensor), room temperature sensor data (i.e. data obtained from a room temperature sensor 332), and/or room humidity sensor data (i.e. data obtained from a room humidity sensor 330), etc.

The sleep system 100 may include one or more output interfaces 380. The output interface 380 may be used for outputting information from the sleep system 100. In some embodiments, the output interfaces 380 may include a display 390. The display 390 may, for example, be a liquid crystal display (LCD) or a display of another type. In some embodiments, the display 390 may be a touchscreen display. The touchscreen display may be used both as an output interface and an input interface for receiving input at the sleep system 100. The display 390 may be controlled by the main processor 117 and used for providing a visual output of information derived from one or more of the sensors. For example, in at least some embodiments, the display 390 may, in one operating mode, display a display screen which provides a score such as a sleep score, a sleep environment (a.k.a. hygiene) score, a mattress health score, etc. The output interfaces may be used for providing feedback based on sleep state information determined at the sleep system 100. Such sleep state information will be described in greater detail below.

Accordingly, in at least some embodiments, a processor may cause the display 390 to display sleep state information for an occupant of the mattress 101. Such information may, for example, indicate times when an occupant fell asleep, woke up, entered a particular stage of sleep, etc.

In some embodiments, a processor 117 may cause a display 390 to display sleep disorder information for an occupant. As noted above, this information may indicate whether a user has or is likely to have a sleep disorder. The sleep disorder may, for example, include and one or combination of: insomnia, narcolepsy, sleep apnea, bruxism, delayed sleep phase syndrome, advanced sleep phase syndrome, periodic limb movement disorder, sleep walking, sleep talking, bed wetting, etc.

Furthermore, in some embodiments, the processor(s) may cause the display 390 to display information about the health of the mattress 101. As noted above, this information may, for example, include an indication of when the mattress was last rotated and/or flipped, an indication of a total amount of usage of a mattress over its life, an indication of a total amount of usage of a mattress since its last flip or rotation, and/or an indication of a humidity level associated with the mattress. In at least some embodiments, the processor may cause an alert to be displayed if it determines that the humidity levels associated with the mattress are likely to cause mattress health issues, such as mold. Similarly, in some embodiments, the processor may cause a mattress life indicator to be displayed. The mattress life indicator may alert the occupant when it is time to replace the mattress. In at least some embodiments, the processor may cause a mattress flip or rotation indicator to be displayed. The mattress flip or rotation indicator may alert the occupant when it is time to flip or rotate the mattress.

Furthermore, in some embodiments, the processor(s) may cause information about a sleeping environment associated with the mattress 101 to be displayed. The sleeping environment information may, for example, include a measure of a humidity level in the room where the mattress is located, or a measure of a temperature level in the room where the mattress is located. Other sleeping environment information may be displayed in other embodiments.

The output interfaces 380 may also include one or more wireless communication subsystems 370. The wireless communication subsystem 370 may be coupled with the main processor 117 and used to send data to or receive data from another system or device.

In at least some embodiments, the wireless communication subsystems 370 may include a Bluetooth™ subsystem. The Bluetooth subsystem is a short-range communication subsystem which may, for example, use Bluetooth-formatted communications to connect with a nearby paired device, such as a mobile device 1200 (FIG. 12) including a smartphone or tablet computer. The mobile device may, in at least some embodiments, have installed thereon a mattress monitoring application which is configured to interface with the sleep system 100. For example, the sleep system application may be configured to use the data received from the sleep system 100 to generate a display on a display 1290 (FIG. 12) of a mobile device and/or a laptop or desktop computer. The display may display information of the type described above as being displayed on the sleep system's display 390. For example, various information about an occupant's sleep, the sleeping environment and/or the mattress health may be displayed.

In some embodiments, the wireless communication subsystems 370 may include a Wi-Fi subsystem and/or a cellular subsystem such as a 3G, 4G or Long Term Evolution (LTE) network subsystem. The Wi-Fi subsystem may be configured to communicate using a Wi-Fi protocol. The Wi-Fi subsystem may, for example, provide connectivity to the Internet via a router.

In at least some embodiments, the wireless communication subsystem 370 allows the sleep system 100 to send data to another device, server or system for further processing. For example, the other device, server or system may be configured to perform one or more of the methods described below, or a portion thereof.

The electrical components of the sleep system 100 (such as the processor(s), sensors, etc.) may be connected to and receive power from one or more power source 312. In some embodiments, the sleep system 100 may include or be connectable to a power cable which connects the sleep system 100 to a mains power source, which may be an alternating current (AC) power source. In at least some embodiments, an AC to DC (direct current) converter may be used to convert the alternating current provided by the mains power source to DC, which may be required by at least some of the electrical components of the sleep system in some embodiments.

Further, in at least some embodiments, the power source 312 may include a battery, which may be inserted into a battery interface. The battery may be included instead of or in addition to a connection to a mains power source.

In at least some embodiments, the wireless communication subsystem 370, the memory 372, the display 390 (and/or another output interface 380), and/or the main processor 117, may be provided in a central processing unit 132. The central processing unit 132 may include a housing which houses the components of the central processing unit 132. In some embodiments, the central processing unit 132 may be included in the mattress 101. For example, in the example embodiment of FIG. 1, the central processing unit 132 is embedded into the mattress. The central processing unit 132 may be located at a side of the mattress. Such a location may provide less obstruction for signals sent and received via the wireless communication subsystem 370 than embodiments where the central processing unit 132 is more centrally located. Further, such a location may allow the display 390 to protrude from a side of the mattress 101 where it may be easily viewed.

In the embodiment illustrated in FIG. 1, the central processing unit 132 is located at a bottom side 104 of the mattress 101. In other embodiments, the central processing unit 132 may be located at either the left side 106 or the right side 108 of the mattress 101. In at least some embodiments, the central processing unit is located away from a location of the mattress where the occupant typically sleeps. Such locations may minimize the interference on a wireless signal caused by the occupant.

In other embodiments, the central processing unit 132 or a portion thereof, may be provided in an external peripheral which may connect to the sleep system 100 through either a wired or wireless connection. For example, in some embodiments, a cable may connect the external peripheral to the sleep system 100. The peripheral may, for example, be configured to rest on a flat surface, such as a tabletop. By way of example, the external peripheral may be placed on a nightstand in some embodiments.

Furthermore, in other embodiments, the components of the central processing unit 132 may be physically separated, with some of the components being provided in the mattress 101 and some of the components being provided in a connected external peripheral. In some such embodiments, both the mattress 101 and the external peripheral may include a processor. One or both of these processors may be configured to perform any one or more of the methods described below.

The sleep system 100 may also include sensors associated with a sleeping environment sensing array 306. The sleeping environment sensing array is configured to obtain information about the environment where the mattress 101 is located. In at least some embodiments, the sleeping environment sensing array 306 may be provided in the central processing unit 132. As noted above, the sleeping environment sensing array 306 may be provided in the mattress 101 itself or in an external peripheral. Accordingly, in at least some embodiments, one or more of the sensors in the sleeping environment sensing array 306 may be provided in the mattress 101 and, in at least some embodiments, one or more of the sensors in the sleeping environment sensing array 306 may be provided in the external peripheral.

As will be described in greater detail below, this information could be used to provide reports to an occupant (e.g. via a display, such as the display 390 of the sleep system or a display 1290 (FIG. 12) on another device such as a mobile device 1200 connected to the smart mattress). These reports may evaluate the sleep environment (i.e. the area in the vicinity of the mattress). By way of example, information about the lighting levels, dust levels, gas levels (such as carbon monoxide levels or natural gas levels), humidity levels, temperature levels and/or ambient noise levels may be provided. Furthermore, in at least some embodiments, data of various types may used to generate a sleep environment score. The sleep environment score may be based on two or more of the following factors: lighting levels, gas levels, dust levels, humidity levels, temperature levels and/or ambient noise levels.

Room humidity information may be obtained from a room humidity sensor 330. The room humidity sensor 330 may be of the type described above (i.e. the body humidity sensor 124). However, in at least some embodiments, the room humidity sensor 330 may be located away from a region of the mattress in which an occupant typically sleeps, to prevent the humidity sensor from capturing humidity information associated with the occupant. For example, in some embodiments, the room humidity sensor 330 may be included in an external peripheral which may connect to the sleep system 100 through either a wired or wireless connection. The room humidity sensor 330 generates an electrical signal based on the amount of humidity in the region of the humidity sensor 330. That is, the electrical signal output by the humidity sensor includes humidity information. This humidity information may be provided to a processor such as the main processor 117 for analysis.

Room temperature information may be obtained from a room temperature sensor 332. The room temperature sensor 332 may be of the type described above with reference to the body temperature sensor 122. However, in at least some embodiments, the room temperature sensor 332 may be located away from a region of the mattress in which an occupant typically sleeps, to prevent the temperature sensor from capturing temperature information associated with the occupant. For example, in some embodiments, the room temperature sensor 332 may be included in the external peripheral described above. The room temperature sensor 332 generates an electrical signal based on the temperature in the region of the room temperature sensor 332. That is, the electrical signal output by the temperature sensor includes temperature information. This temperature information may be provided to a processor such as the main processor 117 for analysis.

In some embodiments, the sleeping environment sensing array 306 may include a microphone 334. The microphone 334 may, for example, be used to obtain sound information. As is known, the microphone may convert sound waves into electrical energy variations, which may be provided as an electrical signal to a processor (this signal may be converted to a digital signal by an ADC before input to the processor in some embodiments). This electrical signal may be said to contain sound information. This sound information may, for example, indicate the amount of ambient noise in the room where the sleep system 100 is located. In at least some embodiments, the microphone 334 may be located away from a region of the mattress in which an occupant typically sleeps, to minimize the effect of noise from the occupant (e.g. due to movements, snoring, etc.) on the captured sound. That is, the microphone may be separated from the occupant so that the captured sound indicates sound caused by other sources of noise or sound, apart from the occupant. In other embodiments, the microphone may be located near the occupant to detect occupant-generated audio, such as snoring, breathing, etc.

In at least some embodiments, the microphone 334 may be a condenser microphone, which may also be referred to as a capacitor microphone or an electrostatic microphone. By way of example, in some embodiments, the microphone 334 may be a CMC-2742WBL-25L model microphone manufactured by CUI Inc.

In some embodiments, the sleeping environment sensing array 306 includes a light sensor 336. The light sensor 336 includes a light sensitive element which generates an electrical signal responsive to received light. That is, the electrical signal includes light information which indicates the amount of received light received at the light sensor 336. Thus, the light information indicates how light (or how dark) the room is. In at least some embodiments, the light sensor is an Everlight Electronics™ ambient light sensor, such as an AS-PT243-3C/L177. The light sensor 336 may sense light in the visible range. In at least some embodiments, the light sensor 336 may sense light with a wavelength in the range of 390 to 700 nm. The light information generated by the light sensor is provided to a processor (such as the main processor 117) as an electrical signal. The light sensor 336 may not function if it is obstructed. Accordingly, in at least some embodiments, the light sensor 336 is not included in the mattress 101 where it might be obscured by bedding, for example; instead, the light sensor 336 may be included in the external peripheral.

In some embodiments, the sleeping environment sensing array 306 includes a dust sensor 338. The dust sensor 338 may be an optical dust sensor and may include an emitting diode and a photoresisitor. By way of example, in some embodiments, the dust sensor 306 may be a model GP2Y1010AU0F dust sensor manufactured by Sharp™. In some embodiments, the dust sensor 338 may measure dust concentrations in the range of 0 to 0.8 mg/m$^3$. The dust sensor 338 generates an electrical signal which indicates the amount of dust in the vicinity of the dust sensor 338. The amount of dust in the vicinity of the dust sensor 338 may be referred to as dust information. This dust information may be provided to a processor (such as the main processor 117) as an electrical signal.

The dust sensor 338 may not function if it is obstructed. Accordingly, in at least some embodiments, the dust sensor 338 is not included in the mattress 101 where it might be obscured by bedding, for example; instead, the dust sensor 338 may be included in the external peripheral.

The sensors in the sleeping environment sensing array 306 are coupled to one or more processors, such as the main processor 117. In the embodiment illustrated, the sensors in the sleeping environment sensing array 306 connect directly to the main processor 117. However, in other embodiments, these sensors may not connect directly to the main processor; one or more microcontrollers may be connected between the sleeping environment sensing array and the main processor.

In some embodiments (not shown), the sleep environment sensing array 306 may be provided in whole or in part by a mobile device 1200. More particularly, sensors on the mobile device 1200 could be used as the sleeping environment sensing array 306.

It will be appreciated that the sleep system 100 may include components in addition to those described above, including, for example, additional sensors and that the components described above may be arranged in a different manner than that illustrated in FIG. 1, 2 or 3. For example, in some embodiments, the microphone (which is illustrated as being included in the sleeping environment sensing array 306 in FIG. 3) could be instead included in an occupant sensing array (such as the left occupant sensing array 302 and/or the right occupant sensing array 304). Such a microphone could, for example, be used to detect sounds associated with the occupant, such as snoring, etc.

By way of further example, in at least some embodiments, the sleep system 100 may include one or more input interfaces which are not illustrated in FIG. 3. Such input interfaces may include a keyboard, keypad, button, touchscreen, etc. The input interface(s) may be connected to a processor (such as the main processor 117) to allow the processor to receive input. The input interfaces may also be referred to as input mechanisms or input devices, in some embodiments.

Furthermore, the humidity sensor(s) 124 which are described as being embedded into the mattress 101 could be used for other purposes apart from sensing conditions associated with the occupant. For example, they may also be used to detect mattress health information. For example, they may be used to determine whether the mattress is too wet, which could cause mould.

As will also be described in greater detail below, in at least some embodiments, one or more of the force sensors 120a-120h which are embedded into the mattress 101 may be used for evaluating the health of the mattress. For example, the force sensors 120a-120h could be used to monitor usage of the mattress. Usage information may be used to provide feedback via an output interface 380 about the health of the mattress. This feedback may, for example, prompt a user to flip and/or rotate the mattress and/or may suggest replacement of the mattress.

Additionally, in at least some embodiments, the sleep system 100 may include timing circuitry or timing components. The timing circuitry or timing components may be used, for example, to track a time of day and/or a date. Accordingly, in at least some embodiments, such timing components may include a clock. This information may be used in some of the methods described below. For example, this information, together with information from the force sensors 120a-120h may be used to determine the time when an occupant went to bed and/or when the occupant woke up. The timing circuitry or timing components may be provided on a processor such as the main processor 117 in at least some embodiments.

Furthermore, it will be appreciated that at least some of the components described above may be omitted in at least some embodiments. For example, one or more sensors could be omitted. For example, in some embodiments, sensors associated with one or more of the occupant sensing arrays 302, 304 may be included but sensors associated with the sleeping environment sensing array 306 may be omitted. By way of further example, in other embodiments, sensors associated with one or more of the sleeping environment sensing arrays 306 could be included and the sensors associated with the occupant sensing arrays 302, 304 omitted.

Sleep State Information Determination

In at least some embodiments, one or more of the processors that are included in the sleep system 100 or in a server, system or device that is coupled to the sleep system may be configured to determine sleep state information for an occupant based on data obtained from one or more of the force sensors. The one or more processors may include, for example, the main processor 117, the microprocessors 130a, 130b, a processor provided on an external peripheral of the type described above, a processor 1217 on a mobile device 1200 connected or connectable to the sleep system 100, a processor on a remote server connectable to the sleep system 100, and/or another processor associated with the sleep system 100.

More particularly, one or more memories associated with the one or more processors may include processor-executable instructions which, when executed, configure the processor to perform one or more of the methods 400, 500, 600, 700, 800, 900 described below with reference to FIGS. 4 to 9. For example, in some embodiments, memory 372 associated with the main processor 117 may include such processor-executable instructions to configure the main processor 117 to perform one or more of the methods.

The methods 400, 500, 600, 700, 800, 900 described below with reference to FIGS. 4 to 9 may be used to determine sleep state information. As will be described in greater detail below with reference to FIGS. 4 to 9, the sleep state information may include, for example: sleep stage information which indicates a sleep stage of an occupant and/or the times at which the occupant entered and/or exited various sleep stages (see FIG. 5), awake and/or asleep status information which indicates whether the occupant is awake or asleep and/or the times at which the occupant fell asleep and/or woke up (see FIG. 5), sleep onset latency information which is a measure of the amount of time required by an occupant to fall asleep (see FIG. 5), sleep position information which indicates a sleeping position of the occupant and/or the times when the occupant entered and exited various sleeping positions (see FIG. 8), and/or sleep disorder information (see FIG. 9). The sleep disorder information may indicate whether an occupant is suffering from a sleep disorder, the nature of the sleep disorder affecting the occupant, and/or a likelihood score which indicates the likelihood that the occupant is suffering from a given sleep disorder.

Figure 6:
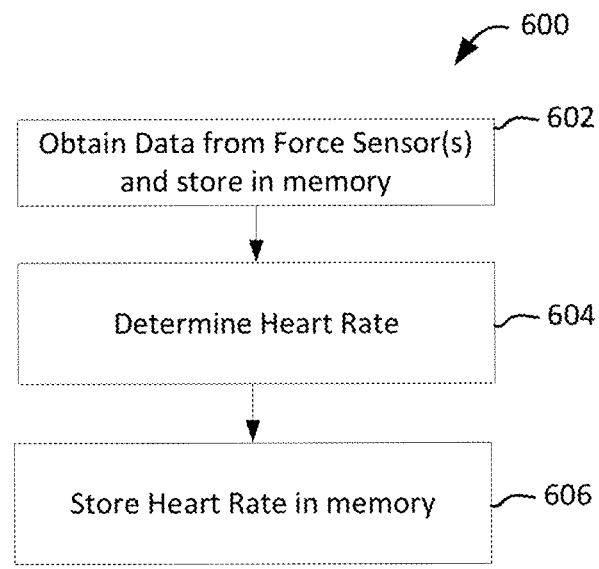
FIG. 6 is a flowchart of a method of determining heart rate.
Figure 7:
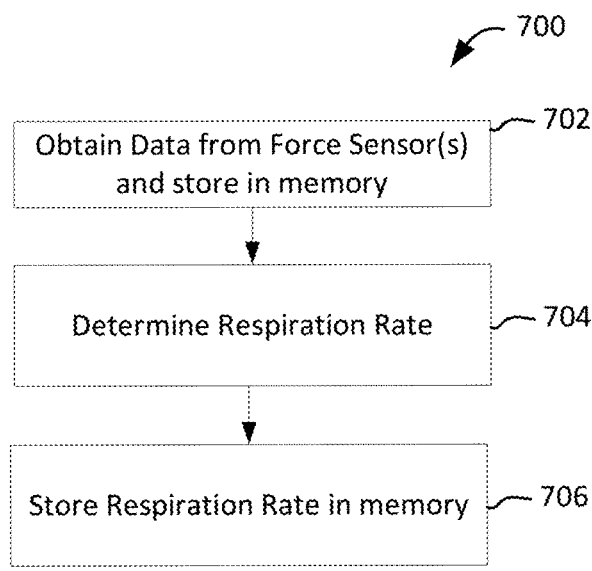
FIG. 7 is a flowchart of a method of determining respiration rate.

At least some of the sleep state information described above may be determined based on movement information which indicates the quantity and or times of movements of an occupant (see FIG. 4), heart rate information which indicates a heart rate of the occupant and which may track changes in the heart rate over time (see FIG. 6), and/or respiration rate information which indicates a respiration rate of the occupant and which may track changes in the respiration rate over time (see FIG. 7).

After sleep state information is determined by a processor associated with the sleep system, it may be store in memory (such as the memory 372 associated with the main processor 117 and/or memory associated with a mobile device 1200 wirelessly connected to the sleep system 100 and/or memory associated with a server connected to the sleep system 100 and/or the mobile device 1200) and/or may be used to generate an output at an output interface associated with the sleep system or a mobile device connected or connectable to the sleep system. In some embodiments, the output interface may be a display. For example, in some embodiments, an alarm may be generated on the display based on the sleep state information. By way of example, the alarm may inform a user that they are likely suffering from a sleep disorder.

Extraction of Movement Component

In at least some embodiments, the sleep system 100 may extract a movement component from the data obtained from the force sensors. This extraction may, for example, obtain a movement component which represents movements of the occupant which are not caused by heart or breathing induced movements. That is, the movement component may represent movements that are caused by an occupant shifting in bed, changing positions in bed, moving a limb, etc.

In some embodiments, the sleep system 100 may determine whether a given sample obtained from a force sensor 120a-120h represents movement of the occupant. In at least some embodiments, this determination may be performed based on changes of force over time using a moving average difference method. That is, sudden changes of force measured at one of the force sensors may be interpreted as a movement.

Figure 4:
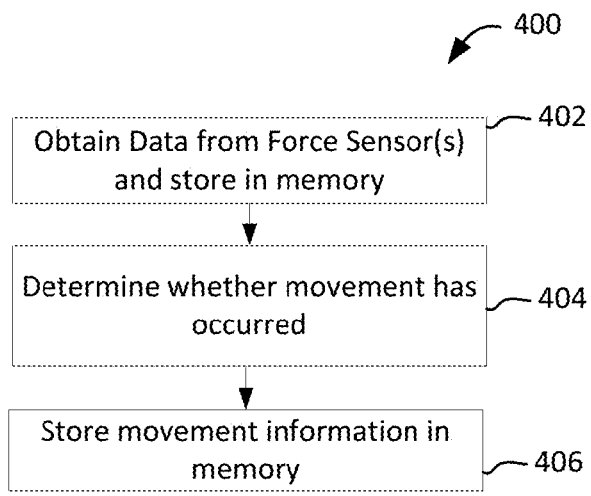
FIG. 4 is a flowchart of a method of obtaining movement information.

Referring now to FIG. 4, one example method 400 will now be discussed. The method 400 may, for example, be performed by one or more processors connected to or associated with the sleep system 100, such as the main processor 117 and the microprocessors 130a, 130b. More particularly, one or more memories associated with the one or more processors may include processor-executable instructions which, when executed, configure that processor to perform a method described below.

At 402, sensor data is obtained from the force sensor(s) 120a-120h. The sensor data may be periodically obtained; for example, at a predetermined interval and, in at least some embodiments, the sensor data may be obtained from each of the force sensors 120a-120h. The sensor data obtained at 402 may represent readings at discrete points in time which may be referred to as samples. Each sample is, therefore, associated with a specific point in time. In at least some embodiments, samples from all of the force sensor(s) may be obtained at each time interval. That is, all of the force sensors may be sampled at once to obtain a number of samples representing the force measured at various locations of the mattress 101 at a single point in time. The sensor data (i.e. the samples) may, in at least some embodiments, be stored at 402 in a memory associated with the sleep system 100, such as memory 372 associated with the main processor 117. In other embodiments, the sensor data may be stored in another type of memory, such as a cache.

At 404, the processor determines whether a movement occurred based on the sensor data obtained from the force sensor(s). In at least some embodiments, the processor may determine whether a movement has occurred at a given time, t1, by comparing the sensor data (i.e. the force reading) from a force sensor at that point in time to sensor data from that same force sensor before and/or after that given time (i.e. before or after t1).

In some embodiments, the processor may determine whether a movement has occurred at a given time by comparing front window readings to back window readings. The front window readings are sensor samples obtained before the given time for which movement is being evaluated and the back window readings are sensor samples obtained after the given time for which movement is being evaluated. In at least some embodiments, the processor may determine whether a movement has occurred at a given time by comparing an average of a predetermined number of front window readings with an average of a predetermined number of back window readings. That is, a moving average difference method may be used to determine whether a movement has occurred at a given time. This moving average difference may, in some embodiments, be a multi-point average difference method which calculates the average of multiple samples in the front window and multiple samples in the back window in order to determine whether a movement has occurred. By way of example, in some embodiments, a five point average difference method may be used which calculates the average of five samples in the front window and five samples in the back window.

By way of example, in some embodiments, the processor may determine whether a movement has occurred at a given time, t1, by evaluating the following equation to find a difference, D, between a front window average and a back window average for a sensor, k:

$$D = \sum_{i=n[k]-x}^{n[k]-1} i/x - \sum_{i=n[k]+1}^{n[k]+x} i/x$$

where k is used to identify the specific force sensor from which the data is obtained, n[k] is the current point of data (i.e. the data at time t1) from the force sensor, x is a predetermined number of samples which will be used to form each of the front window and the back window. In at least some embodiments, the predetermined number, x, is five.

After obtaining the difference, D, the processor may compare the difference to one or more predetermined thresholds. In at least some embodiments, if the difference, D, is above the predetermined threshold, then a movement is determined to have occurred. In other embodiments, a movement may be detected based on other criteria. For example, in some embodiments, the rate of change of the difference, D, and/or the magnitude of the difference, D, may be compared to respective thresholds to determine whether a movement has occurred. In at least some embodiments, a movement may also be categorized, by a processor, in terms of the speed and size of the movement.

This determination may be performed separately for each force sensor 120a-120h in a sensor set 150, 152. That is, the processor may analyze sensor data from each force sensor 120a-120h independently to determine whether a movement has occurred. For example, in some embodiments, the difference, D, between the front window average and the back window average may be evaluated for each force sensor 120a-120h and each of these differences may be compared with one or more predetermined thresholds. If any of the differences for the force sensors 120a-120h in a sensor set 150 associated with a first occupant exceed the respective threshold, then the processor may determine that the first occupant has moved at the time t1. That is, if any of the force sensors 120a-120h which are in the first sensor set 150 indicate that a movement has occurred, then the processor may determine that the occupant associated with the first sensor sent 150 has moved. This determination may be recorded in memory at 406. That is, movement information may be stored in memory at 406, which may be memory associated with the sleep system 100. For example, the processor may update the memory to, for example, increment a movement counter associated with the first sensor set 150 to indicate that the occupant associated with the first sensor set 150 has moved. By way of further example, in some embodiments, after determining that a movement has occurred, the processor may update the memory to indicate a time associated with the movement.

If, however, none of the differences for the force sensors 120a-120h in the sensor set 150 exceed the respective threshold (i.e. if none of the force sensors 120a-120h in the sensor set 150 indicate that a movement has occurred at time t1), then the processor determines that no movement of the occupant associated with that sensor set 150 has occurred at the given time, t1. In some embodiments, at 406 the processor may update memory to store movement information which indicates that a movement did not occur at time t1.

The movement determination described above may be performed independently for each sensor set 150, 152. That is, sensor data from the force sensors 120a-120h associated with the first sensor set 150 may be used to determine whether a first occupant has moved and sensor data from the force sensors 120a-120h associated with the second sensor set 150 may be used to determine whether a second occupant has moved.

Additionally, while the method 400 described above generally refers to a determination of movement at a single point in time, in practice, the steps of the method may be repeated to determine whether a movement has occurred over the course of an extended period of time. For example, in some embodiments, a determination as to whether a movement has occurred may be made for each sensor sample.

Furthermore, since a single movement may create a change in the force reported at a force sensor for an extended period of time, to prevent double recording of movements, in at least some embodiments, the processor may be configured to enforce one or more rules regarding the maximum number of movements that will be counted for each sensor set 150, 152 within a given time frame. For example, in at least some embodiments, the processor may only permit one movement to be registered for each sensor set 150, 152 each second. In such embodiments, when a movement is detected at one of the sensor sets 150, 152, the processor may wait until the predetermined period of time (e.g. one second) has expired before it will permit another movement to be registered.

Thus, the method 400 may be used to identify movements of an occupant from data obtained from the force sensors 120a-120h.

Determine Sleep Stage and/or Whether Occupant is Awake

As noted above, in at least some embodiments, sleep state information may be determined by a processor based on data obtained from the force sensors. This sleep state information is information about an occupant's sleep. In some embodiments, this sleep state information may indicate whether an occupant is asleep. In some embodiments, this sleep state information may indicate the sleep stage of the occupant.

Figure 5:
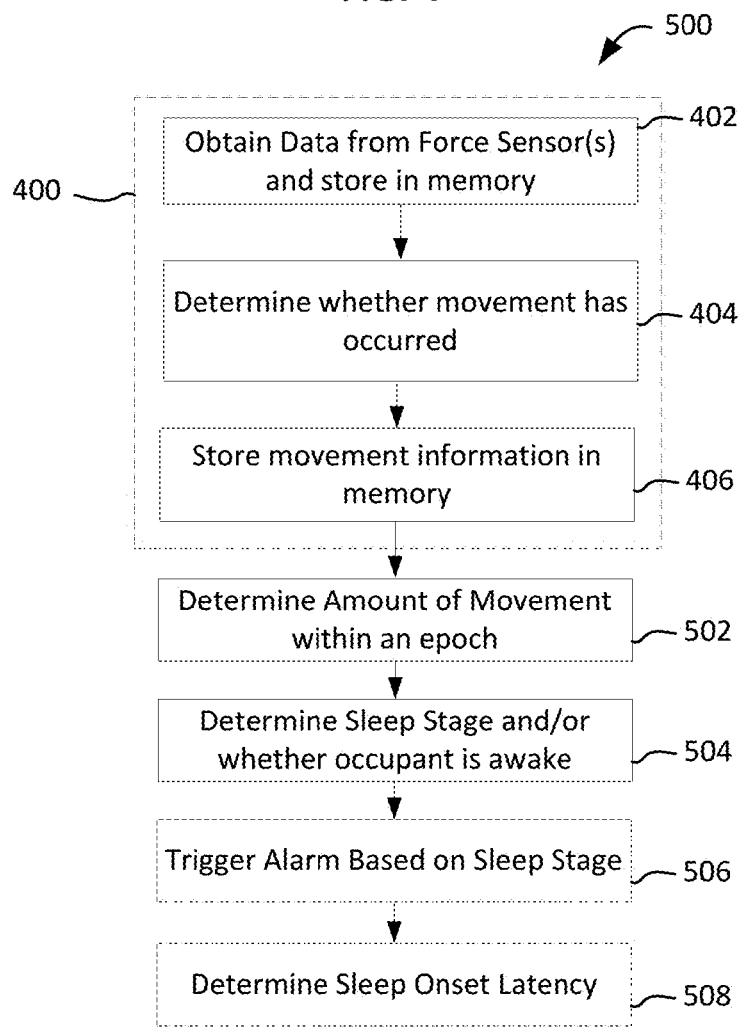
FIG. 5 is a flowchart of a method of determining sleep state information, such as a sleep stage.

Referring now to FIG. 5, an example method 500 for determining such sleep state information is illustrated. The method 500 may be used, for example, to determine a sleep stage of the occupant of a mattress 101 and/or to determine whether an occupant of the mattress 101 is either asleep or awake.

In at least some embodiments, the method 500 may include or be performed after the method 400 of FIG. 4. That is, during the method 500 of FIG. 5, the processor may use movement information to determine a sleep stage of an occupant and/or to determine whether the occupant is asleep or awake. That is, based on the frequency of movements of an occupant, the sleep stage and/or waking status of that occupant may be determined.

Accordingly, in at least some embodiments, the method 400 of FIG. 4 may be performed to obtain movement information. As noted in the discussion of FIG. 4 above, during the performance of this method 400, movements of an occupant are identified from data obtained from the force sensors. The steps 402, 404, 406 of the method 400 are described above with reference to FIG. 4.

At 502, the processor determines a frequency of movements. More specifically, the processor determines the amount of movements for an occupant that have occurred within an epoch of a predetermined duration. That is, the processor may determine the amount of movements that have occurred within a predetermined period of time. By way of example, in some embodiments, this period of time may be one minute. In some embodiments, this period of time may be in the range of thirty seconds to one minute. Other ranges are possible in other embodiments.

The determination of the frequency of movements at 502 is performed based on the movement information obtained during the method 400.

Then, at 504, the processor determines a sleep stage associated with the occupant and/or whether the occupant is awake or sleeping. This determination may be made, for example, based on the frequency of movements determined at 502. More particularly, the processor may determine the sleep stage of the occupant by comparing the amount of movements of the occupant within the epoch to one or more predetermined thresholds. The sleep stages may be the stages accepted by the American Academy of Sleep Medicine.

Similarly, in at least some embodiments, the processor may determine the waking status (i.e. whether the occupant is awake or asleep) by comparing the amount of movements of the occupant within the epoch to one or more predetermined thresholds.

In at least some embodiments, in determining a sleep stage which an occupant is in during a given epoch and/or in determining a waking status, the processor may either determine: 1) that the occupant is awake; 2) that the occupant is in a non-rapid eye movement (NREM) stage 1 state; 3) that the occupant is in a NREM stage 2 state; 4) that the occupant is in a NREM stage 3 state; or 5) that the occupant is in a rapid eye movement (REM) state. These various states and the respective thresholds associated with these states will now be described.

An awake state occurs when the occupant is not sleeping. During this state, the occupant's movement tends to have a higher relative frequency than other states. Accordingly, the processor may determine that the occupant was in a waking state during an epoch if the measure of movements of the occupant during the epoch exceeds a first predetermined threshold. The first predetermined threshold is relatively higher than the thresholds associated with the other states described below.

The NREM stage 1 state is a sleep stage which is between sleep and wakefulness. An occupant's muscles are active during this state and the movement of the occupant tends to be more frequent than in the REM, NREM stage 2, and NREM stage 3 states. The amount of movement is, however, typically less than in the waking state. Accordingly, the processor may determine that the occupant was in the NREM stage 1 state during the epoch if the measure of movements of the occupant during the epoch exceeds a second predetermined threshold and is less than the first predetermined threshold associated with the waking state. The second predetermined threshold is relatively lower than the first predetermined threshold but is relatively higher than the thresholds associated with the REM, NREM stage 2, and NREM stage 3 states.

REM sleep occurs when most muscles are paralyzed. Thus, the frequency of movements during REM sleep tends to be less than in the waking state and less than in the NREM stage 1 state, but more than in the NREM stage 2, and NREM stage 3 states. Accordingly, the processor may determine that the occupant was in the REM state during the epoch if the measure of movements of the occupant during the epoch exceeds a third predetermined threshold and is less than the second predetermined threshold associated with the NREM stage 1 state. The third predetermined threshold is relatively lower than the first predetermined threshold and the second predetermined threshold but is relatively higher than the thresholds associated with the NREM stage 2, and NREM stage 3 states.

NREM stage 2 sleep is a period of theta activity, where it is difficult to awaken the occupant. NREM stage 2 sleep is typically characterized by less frequent movements than the waking, NREM stage 1 and REM states, but more frequent movements than in the NREM stage 3 state. Accordingly, the processor may determine that the occupant was in the NREM stage 2 state during the epoch if the measure of movements of the occupant during the epoch exceeds a fourth predetermined threshold and is less than the third predetermined threshold associated with the REM state. The fourth predetermined threshold is relatively lower than the first, second and third predetermined thresholds.

NREM stage 3 is a slow wave sleep (SWS) stage. During this stage, the occupant is less responsive to the environment. This stage was formerly divided into two stages—3 and 4. Accordingly, the NREM stage 3 state may be referred to or separated into NREM stage 3 and NREM stage 4 states in some embodiments. NREM stage 3 sleep is typically characterized by less frequent movements than in the other sleep states referred to above. Accordingly, the processor may determine that the occupant was in the NREM stage 3 state during the epoch if the measure of movements of the occupant during the epoch is less than the fourth predetermined threshold.

Accordingly, in at least some embodiments, four predetermined thresholds may be used to determine which of the five sleep states discussed above an occupant is in during the epoch. It will be appreciated that a different number of thresholds may be used in other embodiments. For example, in some embodiments, the processor may be configured to determine whether the occupant is either in: 1) an asleep state; or 2) an awake state. An asleep state may be a state in which the occupant is either in the REM, NREM stage 2 or NREM stage 3 state. In some embodiments, the asleep state may also include the NREM stage 1 state. That is, if an occupant is in NREM stage 1, then they may be considered to be asleep. In some embodiments, such relationships may be used to determine that an occupant is asleep; for example, if the user is in either the REM, NREM stage 2, NREM stage 3 (and in some embodiments NREM stage 1) states, then the processor may determine that the occupant is asleep. However, in other embodiments, the determination of whether an occupant is asleep or awake may be performed in another manner. For example, a single threshold may be used in some embodiments. That is, the measure of movements of an occupant during an epoch may be compared to this threshold, and if the movements exceed the threshold then the occupant may be determined to be awake, but if the movements do not exceed the threshold then the occupant may be determined to be asleep.

Accordingly, in at least some embodiments, at 504, the processor may determine sleep state information which indicates whether the occupant is asleep during an epoch and/or a stage of sleep which the occupant was in during the epoch. Such sleep state information may be stored in memory associated with the sleep system 100, output to a display associated with the sleep system 100 or an associated device or system (such as a mobile device), etc. For example, in some embodiments, a sleep log may be updated and/or created. The log may indicate the time at which a user fell asleep, woke up, entered each stage of sleep and/or exited each stage of sleep.

The method 500 may be repeatedly performed to track such information over a prolonged period of time; for example, throughout the night.

The method 500 may be independently performed for each occupant. That is, for each sensor set 150, 152 that is associated with a different occupant, the method 500 may be independently performed so that, for each occupant, the processor independently determines the sleep stage which that occupant is in and/or whether that occupant is asleep.

In some embodiments, other information may be used instead of or in addition to the movement information described above to predict the sleep stage of an occupant. For example, in some embodiments, body temperature, heart rate and/or respiration rate may be used to predict the sleep stage of the occupant. Accordingly, the processor may be configured to determine the sleep state information based on temperature readings, heart rate, respiration rate, and/or other information, in some embodiments.

In some embodiments, at 506 an alarm associated with an alarm clock function may be triggered based on the sleep stage of the occupant. More particularly, an input interface provided on the sleep system 100 or on a device connected to the sleep system (such as a mobile device) may be used to allow an occupant to input timing information associated with the alarm. The timing information may, for example, indicate an ideal time when the user would prefer to wake up, a latest time when the user would like to wake up and/or a range of times during which the user would like to wake up. A wakeup window may be determined from such information by the processor. The wakeup window is the range of times during which an alarm will be triggered to wake up the occupant. The processor then uses the sleep stage information to predict the time during the wakeup window when the occupant will be in the lightest stage of sleep. An alarm may then be triggered at the predicted time. The alarm may, for example, be an audible, visual and/or vibratory alarm which may be produced through an output interface of the sleep system 100, such as a speaker or vibratory device (such as a vibration motor which may be embedded into the mattress on one of the sides of the mattress and which could be used for waking one occupant but not the other occupant i.e. it may be located at or near one side but away from the other side and each side may have a separate vibration motor, each associated with a separate one of the occupants), or through an output interface of a connected peripheral or device, such as a mobile device.

As noted above, in some embodiments, the mattress 101 may be configured for two occupants. In such embodiments, the sleep state of both occupants may be used by the processor when selecting a time for triggering the alarm during the wakeup window. For example, in some embodiments, the processor may determine a time when the occupants will collectively be in their lightest sleeps states. By way of example, this determination may be made by assigning scores to each of the sleep stages, with the lowest score representing the lightest stage of sleep and the highest the deepest sleep. A joint sleep score could be defined as the sleep score of all occupants of the mattress 101. Then, the processor may select a time for triggering the alarm by finding the time within the wakeup window that minimizes the joint sleep score.

Alternatively, in some embodiments where the mattress 101 is configured for use by two occupants, one of the occupants may be selected by the processor for the purposes of triggering the alarm. For example, in some embodiments, one of the occupants may be selected by determining which of the occupants had a worse sleep. In some embodiments, the alarm may then be triggered based on the sleep stage of the occupant having the relatively worse sleep. The occupant having a relatively worse sleep may be the occupant who: slept the least, woke up the most, had a lower sleep score, etc. Example methods of determining a sleep score for an occupant will be discussed in greater detail below.

In some embodiments, the alarm, once triggered may be shut off when the processor detects that one of the occupants gets off the bed. In some embodiments, the alarm, once triggered may be shut off when the processor detects that all of the occupants got off the bed. The processor may determine whether an occupant has gotten off the bed based on data obtained from the force sensors. For example, when the force sensors 120a-120h indicate forces below one or more thresholds, then the processor may determine that the occupant has gotten off the bed and may stop the alarm.

In some embodiments, the force sensors 120a-120h may also be used as an input interface which allows an occupant of the mattress 101 to input an instruction to the processor to instruct the processor to enable a snooze function of the alarm (or to input another instruction). For example, the processor may be configured to recognize one or more gestures which may be performed by movement of the occupant's body and which may be detected using data from one or more of the force sensors 120a-120h. By way of example, one possible gesture may involve a user briefly lifting one or more limbs (such as a leg) and then forcefully placing that limb back onto the mattress. Such a gesture may, for example, be interpreted as a snooze command.

The sleep stage information which is determined according to the method 500 of FIG. 5 may have other uses instead of or in addition to the alarm. For example, in some embodiments, at 508, sleep onset latency may be determined. The sleep onset latency is a measure of the difference between the time when an occupant attempted to fall asleep and the time when that occupant fell asleep (which may be determined at step 504). The time when the occupant attempted to fall asleep may be determined before 508 and this step is not specifically illustrated in FIG. 5. By way of example, it may be determined after step 402 of FIG. 5.

The time when an occupant attempted to fall asleep is, in at least some embodiments, the time when the occupant went to bed. The time when an occupant went to bed is the time when the occupant laid on the mattress after having previously not been on the mattress. This time may be identified by the processor based on data from the force sensors 120a-120h. That is, when an occupant goes to bed (i.e. lays on the mattress 101), the processor identifies a large increase in the force measured on at least some of the force sensors (i.e. it detects presence of the occupant). Thus, the processor may determine that an occupant enters the bed when the force measured at a predetermined number of the force sensors 120a-120h exceeds a predetermined threshold. In at least some embodiments, the force sensors 120a-120h may be calibrated so that when the sleep system 100 has no occupants, the force readings from each of the force sensors 120a-120h may be zero.

In some embodiments, a further check may be performed to confirm that the change in force was due to an occupant entering the mattress and not, for example, due to an object being placed on the mattress. For example, a temperature may be obtained from a temperature sensor 122 and compared to a threshold to determine that an occupant has entered the mattress. Furthermore, in at least some embodiments, the processor may require that at least a predetermined number of force sensors are engaged (e.g. are registering forces which exceed one or more thresholds) and/or may require that specific force sensors are engaged before determining that an occupant has entered the mattress. For example, if an upper body force sensor registers a force which exceeds a predetermined threshold, but a middle body force sensor does not register a force which exceeds a predetermined threshold, then the processor may determine that the occupant has not yet entered the bed; the force registered at the upper body force sensor may be caused by an object apart from a human occupant.

In some embodiments, to determine the time when the occupant attempted to fall asleep, the processor may also consult data from the light sensor 336 (FIG. 3). As noted in the discussion of FIG. 3 above, in some embodiments, the sleep system 100 may include or be associated with a light sensor 336. In some such embodiments, this light sensor 336 may be used to identify the time when a user attempted to fall asleep. That is, in some embodiments, the processor may determine that an occupant has attempted to fall asleep when at least the following two conditions are satisfied: 1) the user has entered the mattress (methods for determining whether the occupant has entered the mattress are described immediately above); and 2) the light measured at the light sensor 336 is less than a predetermined threshold. The predetermined threshold may, for example, be a threshold which indicates that the main source of artificial lighting in the room containing the mattress has been turned off or that all sources of artificial lighting are turned off.

After determining that an occupant has attempted to fall asleep and/or entered the mattress, the processor may store, in memory associated with the sleep system, timing information to indicate the time when the occupant first entered the mattress and/or first attempted to fall asleep. This timing information may then be retrieved at 508 and used to determine sleep onset latency. More particularly, the difference between the time when the occupant fell asleep (as determined at 504) and the time when that occupant attempted to fall asleep may be determined, and this elapsed time is the sleep onset latency.

The determination of the sleep onset latency may be performed independently for each occupant of the mattress 101.

The sleep onset latency, which is a further type of sleep state information, may be stored in memory of the sleep system 100. The sleep onset information may, in at least some embodiments, be used to determine a sleep score associated with an occupant and/or to determine whether the occupant suffers from a sleep disorder, such as insomnia. Techniques for determining a sleep score and detecting sleep disorders are described below.

In at least some embodiments, a sleep offset latency (which may also be referred to as wake latency) may be determined by the processor associated with the sleep system 100 or an associated device. This may, in some embodiments, be performed at 508 of FIG. 5. The sleep offset latency is a measure of the amount of time an occupant remains in bed after they wake up. For example, the processor may determine the elapsed time between when the occupant woke up (e.g. when they are no longer in one of the sleep stages in which they are considered to be "asleep") and when the occupant got out of bed (which may be determined from the force sensors and/or the light sensor 336 (e.g. if a light is turned on, in some embodiments, the occupant may be considered to have gotten out of bed since the occupant is no longer actively trying to sleep).

Heart Rate Determination

Due to the principle of ballistocardiography, the pumping of the heart causes oscillatory body motion and mechanical forces to be produced. This force can be measured using the force sensors 120a-120h over time and a heart rate determined.

Referring now to FIG. 6, one such example method 600 is illustrated.

At 602, data is obtained from one or more of the force sensor(s) and may be stored in memory. This feature may, for example, be performed together with step 402 of FIGS. 4 and 5 and may be performed in the manner described with reference to step 402. Since heart rate is typically between 0.5 to 4 Hz, the data may be obtained at 602 at a frequency that is greater than 4 Hz. For example, in at least some embodiments, samples may be obtained at 602 at a rate of 10 Hz.

At 604, the processor determines, from the data obtained from the one or more force sensors, a heart rate for an occupant. The heart rate may, for example, be determined based on data from the upper body force sensors, which are described above with reference to FIG. 1. More specifically, in at least some embodiments the lower body force sensors are not used for the determination of the heart rate. Furthermore, in at least some embodiments, the middle body force sensors are not used for the determination of the heart rate.

To determine the heart rate (at 604), the processor may filter out large changes in force measured at the force sensors 120a-120h which are caused by movement of an occupant. Voluntary body movement typically occurs in the frequency range of 0.25-4 Hz, which overlaps with the heart rate frequency range, so these signals must be discriminated. Changes in force measured at the force sensors that are caused when an occupant shifts positions tend to be greater in magnitude than the changes caused by the occupant's breathing or heart activity. This filtering may be done by comparing the change in force to one or more predetermined thresholds. The processor may also perform smoothing on the data obtained at 602, and may filter out lower frequency components, such as a component caused by respiration or movement, which will be described in greater detail below. Filtering of the frequency to remove frequencies outside of the range of the heart rate (0.5-4 Hz) may be done using linear cut-off filters or bandpass filters designed based on Window functions. Furthermore, the data may be smoothed, amplified, or otherwise processed to obtain a high quality heart rate signal. The heart rate can be extracted using a variety of techniques that can detect the peaks in the data, which can be used to find the interpeak separation and hence the heart rate. Peak detection can be done in a variety of ways such as detection of local minima or maxima in a moving window or by using a fast fourier transform (FFT) and examining the harmonics. The heart rate may be determined at predetermined intervals to obtain heart rate information for an extended period of time and to monitor for changes in the heart rate.

In at least some embodiments, the heart rate may be stored in memory at 606. The heart rate may, for example, be used to determine sleep state information for the occupant. For example, the heart rate may be used to determine a sleep stage of the occupant. The heart rate may, in some embodiments, be used by a processor associated with the sleep system or an associated device for evaluating other health related issues. For example, in some embodiments, a heart rate variability (HRV) may be determined by the processor. This HRV may be stored in memory. In some embodiments, the HRV may be used by a processor to detect other conditions. For example, a lower than normal HRV may be indicative of heart failure, diabetic neuropath, depression, post-traumatic stress disorder (PTSD), stress, susceptibility to sudden infant death syndrome, etc. HRV can also be related to having sleep apnea. Thus, in at least some embodiments, the HRV may be compared, by a processor, to one or more predetermined thresholds to determine whether an occupant has, is likely to have and/or is susceptible to any one or more of these conditions. Faster resting heart is a risk factor for cardiovascular mortality and can be an indicator of a heart attack. It may also be used to detect arrhythmias and other heart rate abnormalities. Accordingly, in some embodiments, a processor may use the heart rate to determine whether an occupant has, is likely to have and/or is susceptible to: cardiovascular mortality, heart attacks, arrhythmias, and/or heart rate abnormalities.

It will be appreciated that the method 600 may be performed independently for each occupant of the mattress. For example, the force sensors in the first sensor set 150 may be used to determine the heart rate of a first occupant and the force sensors in the second sensor set 152 may be used to determine the heart rate of a second occupant.

Respiration Rate Determination

In at least some embodiments, the processor may be configured to determine a respiration rate of the occupant based on data obtained from the force sensors. Referring now to FIG. 7, one such example method 700 is illustrated.

At 702, data is obtained from one or more of the force sensor(s) and may be stored in memory. This feature may, for example, be performed together with step 402 of FIGS. 4 and 5 and/or step 602 of FIG. 6 and may be performed in the manner described with reference to step 402. Since respiration rate is typically between 0.1 to 0.5 Hz, the data may be obtained at 702 at a rate that is greater than 0.5 Hz. For example, in at least some embodiments, samples may be obtained at 702 at a rate of 10 Hz.

At 704, the processor determines, from the data obtained from the one or more force sensors, a respiration rate for an occupant. The respiration rate may, for example, be determined based on data from the upper body force sensors, which are described above with reference to FIG. 1. More specifically, in at least some embodiments the lower body force sensors are not used for the determination of the respiration rate.

To determine the respiration rate (at 704), the processor may filter out large changes in force measured at the force sensors 120a-120h which are caused by movement of an occupant. Voluntary body movement typically occurs in the frequency range of 0.25-4 Hz, which may overlap with the respiration rate frequency range, so these signals are discriminated. Changes that are caused when an occupant shifts positions tend to be greater in magnitude than the changes caused by the occupant's breathing or heart activity. This filtering may be done by comparing the change in force to one or more predetermined thresholds. The processor may also perform smoothing on the data obtained at 702, and may filter out higher frequency components, such as movement components and may, in some embodiments, filter out higher frequency components, such as a component caused by heart activity. Filtering of the frequency to remove frequencies outside of the range of the respiration rate (0.1-0.5 Hz) may be done using linear cut-off filters or bandpass filters designed based on Window functions. As noted above, respiration rate is typically in the range of 0.1-0.5 Hz and heart rate is typically in the range of 0.5-4 Hz. These ranges may be used to separate the respiration component from the heart rate component. For example, one or more thresholds may be established based on these ranges to separate the heart rate component from the respiration component. Furthermore, the data may be smoothed, amplified, or otherwise processed to obtain a high quality respiration rate signal. The respiration rate can be extracted using a variety of techniques that can detect the peaks in the data, which can be used to find the interpeak separation and hence the respiration rate. Peak detection can be done in a variety of ways such as detection of local minima or maxima in a moving window or by using a fast fourier transform (FFT) and examining the harmonics. The respiration rate may be determined at predetermined intervals to obtain respiration rate information for an extended period of time and to monitor for changes in the respiration rate.

In at least some embodiments, the respiration rate may be stored in memory at 706. The respiration rate may, for example, be used to determine sleep state information for the occupant. For example, as will be described in greater detail below, the respiration rate may be used to determine whether the occupant has a sleep disorder. For example, in some embodiments, a processor may consider the respiration rate when determining whether an occupant has sleep apnea.

It will be appreciated that the method 700 may be performed independently for each occupant of the mattress. For example, the force sensors in the first sensor set 150 may be used to determine the respiration rate of a first occupant and the force sensors in the second sensor set 152 may be used to determine the respiration rate of a second occupant.

Sleep Position Monitoring

In at least some embodiments, the processor may be configured to determine sleep state information which identifies a sleep position of an occupant of the mattress 101 (such information may also be referred to as sleep position information). In at least some embodiments, the processor may be configured to determine the most common sleep position of the occupant.

In at least some embodiments, the processor may be configured to recognize predetermined common sleep positions. In some embodiments, these positions may include: a fetus position, a freefall position, a log position, a yearner position, a solider position and a starfish position. The characteristics of these positions are described below. The processor may be configured to identify other positions instead of or in addition to these positions in other embodiments.

In the fetus position, the occupant sleeps on their side in a curled up position. At least one of the occupant's hands is resting near their chin. The fetus is the most common sleep position. More particularly, approximately 41% of people sleep in the fetus position. Thus, the probability that a given occupant will prefer the fetus position is approximately 41%.

The freefall position is a position in which the occupant lies on their stomach with their hands typically elevated, so that they are near the occupant's head. The occupant's head is typically turned to one side. Approximately 7% of people sleep in the freefall position, and so the probability that a given occupant will prefer the freefall position is approximately 7%.

The log position is characterized by the occupant lying on their side with both arms down by their side. The back and legs of the occupant are generally straight in the log position. Approximately 15% of people sleep in the log position, and so the probability that a given occupant will prefer the log position is approximately 15%.

The yearner position is a position in which the occupant sleeps on their side with both arms extended in front of them (i.e. the arms are not at the side of the occupant's body but instead extend in a direction which is generally perpendicular to the occupant's torso). Approximately 13% of people sleep in the yearner position and so the probability that a given occupant will prefer the yearner position is 13%.

The soldier position is a position in which the occupant lies on their back with both arms at their sides. That is, the arms are generally parallel to the torso and typically rest on the mattress. Approximately 8% of people sleep in the soldier position and so the probability that a given occupant will prefer the soldier position is 8%.

The starfish position is a position in which the occupant lies on their back with both arms up around their pillow. That is, the occupant's hands are generally near their head. Approximately 5% of people are said to sleep in the soldier position and so the probability that a given occupant will prefer the starfish position is 5%.

The various sleep positions described above may create different force distributions across the force sensors 120*a*-120*h*. Thus, the sleep position of an occupant may be determined, by the processor, by examining the distribution of forces across the force sensors.

Figure 8:
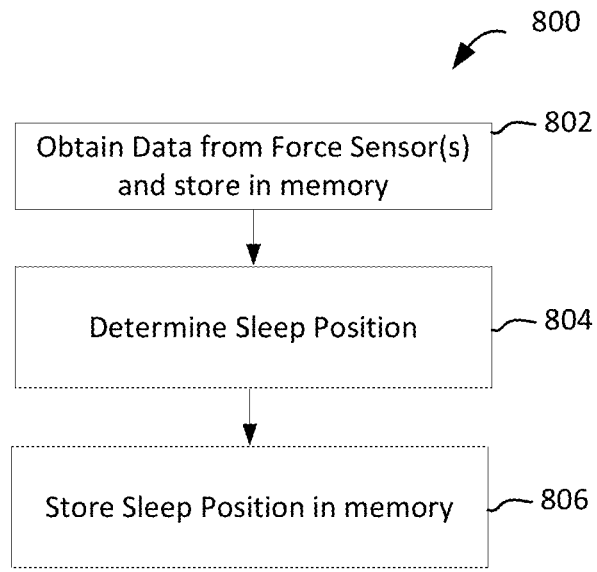
FIG. 8 is a flowchart of a method of determining sleep position.

More particularly, memory 372 associated with the processor 117 may store characteristic information associated with each of a plurality of sleep positions which the processor is configured to identify. This characteristic information may represent a force distribution pattern for each position. Referring to FIG. 8, which illustrates a method 800 of determining sleep position (i.e. determining "sleep position information"), the processor may obtain data at 802 from the force sensors 120*a*-120*h* in the manner described above with reference to step 402 of FIG. 4. This data may be used at 804 to determine the sleep position represented by the data. More particularly, the processor may compare the data obtained from the force sensor(s) with the characteristic information to determine the sleep position associated with the occupant. That is, the processor may determine which one of a plurality of predetermined common sleep positions are represented by the sensor data obtained from the force sensors in a sensor set. This determination may be performed independently for each sensor set so that the sleep position of each occupant may be separately determined.

In at least some embodiments, in determining the sleep position, the processor may consider other data in addition to the force distributions represented in the sensor data. For example, the processor may consider the relative probabilities of each sleep position occurring for an occupant. As noted above, certain sleep positions are more common than others in the general population. This information (i.e. the probability of a random occupant using each sleep position) may, in some embodiments, be considered by the processor when determining the sleep position. For example, in some embodiments, where the distribution of forces does not clearly suggest a specific position (i.e. where the result of this analysis suggests that the occupant may be in one of at least two positions), then the probability information may be used to resolve the ambiguity. For example, the freefall position and the starfish position may produce similar force distributions. Thus, in some circumstances, the force distribution analysis may suggest that the occupant is either in the freefall position or the starfish position, but the force distribution analysis may not clearly indicate which of these two positions are being used. In some embodiments, the processor may resolve this ambiguity by determining that the freefall position is being used, since this position is more common in the general population.

The sleep position of a user may be stored, as sleep state information, in memory associated with the sleep system 100 at 806.

The sleep position of the occupant may be determined repeatedly to account for changes in the occupant's sleep position. In some embodiments, the sleep position may be determined periodically. In some embodiments, the sleep position may be re-determined in response to changes in force distributions observed at the force sensors 120*a*-120*h*. Other triggers may be used to cause the sleep position to be re-determined in other embodiments.

In some embodiments, timing information may be associated with the determined sleep position. That is, the processor may record, in memory, a time at which an occupant entered and/or exited a sleep position. In some embodiments, this timing information may be used to determine an occupant's most common sleep position over an extended period of time, such as a week, a month, a year, etc.

In at least some embodiments, after the most common sleep position has been determined, it may be recorded in memory as sleep state information. In some embodiments, this sleep position may be output via an output interface associated with the sleep system 100. For example, in some embodiments, the sleep position may be displayed on a display associated with the sleep system. In some embodiments, the display may be provided on the sleep system itself and in other embodiments, the display may be provided on a mobile device 1200 which is connected to the sleep system.

Detection of Sleep Disorder(s)

In some embodiments, one or more of the processors associated with the sleep system 100 may be configured to detect one or more sleep disorders. A detected sleep disorder may, for example, be a type of sleep state information that is determined by the sleep system 100.

Figure 9:
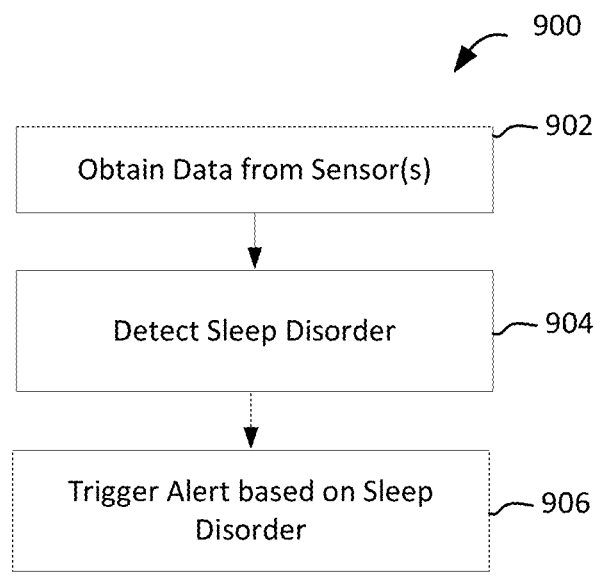
FIG. 9 is a flowchart of a method of detecting a sleep disorder.

Referring now to FIG. 9, an example of a method 900 for detecting a sleep disorder is illustrated. At 902, data is obtained from one or more of the sensors associated of the sleep system 100. For example, data may be obtained from the force sensors 120*a*-120*h*, the temperature sensor(s) 122, the humidity sensor(s) 122, the microphone 334, or any of the other sensors described above with reference to FIGS. 1 and 3. As will be understood from the discussion of the various sleep disorders below, the specific sensors from which data will be obtained will depend on the specific sleep disorders which the sleep system 100 is configured to detect. The data may, for example, be stored in memory associated with the sleep system 100.

At 904, the sleep system detects a sleep disorder. Techniques for detecting sleep disorders are described below and vary based on the specific disorder being detected.

In at least some embodiments, at 906, the one or more processors may be configured to trigger an alert via an output interface associated with the sleep system when one or more of the sleep disorders are detected. For example, the alert may be provided on a display 390 (FIG. 3) of the sleep system 100 and/or on a display 1290 (FIG. 12) of a mobile device 1200 (FIG. 12) associated with the sleep system.

In at least some embodiments, the alert may only be triggered if the sleep disorder appears to exist for a predetermined number of nights. For example, in some embodiments, the alert will be triggered only if the processor detects the sleep disorder for an occupant for a consecutive number of nights.

Various sleep disorders which may be detected by the sleep system 100 will now be described. The sleep system 100 may be configured to detect any one or more of the sleep disorders described below and any combinations thereof.

Insomnia Detection

In at least some embodiments, the one or more processor(s) may be configured to detect insomnia. Insomnia is a sleep disorder in which the occupant has an inability to fall asleep or to stay asleep as long as desired.

In at least some embodiments, insomnia may be detected at step 904 of the method 900 of FIG. 9 by one or more processors associated with the sleep system 100 based on sleep onset latency for an occupant. A method 500 for determining sleep onset latency is described in greater detail above with reference to FIG. 5 and, in particular, with reference to step 508.

In at least some embodiments, sleep onset latency may be compared (at 904 of the method 900 of FIG. 9) to a predetermined threshold to determine whether the occupant has insomnia. The predetermined threshold may effectively indicate a sleep onset latency which is considered too long. In some embodiments, if the threshold is exceeded (i.e. if it takes too long for the occupant to fall asleep), then the processor may determine that occupant may have insomnia. In at least some embodiments, the processor may quantify the likelihood that the occupant has insomnia based on the sleep onset latency.

Other indicators of insomnia may be used instead of or in addition to the sleep onset latency in order to detect insomnia. For example, in some embodiments, the sleep efficiency score (which will be described in greater detail below) may be considered. In some embodiments, the number of awakenings may be considered. That is, the number of times an occupant wakes up over a period of time (such as a night) may be used to determine whether the occupant has insomnia. The number of awakenings may be tracked using the techniques described above with reference to FIG. 5. For example, during step 504 of the method 500 of FIG. 5, if the processor detects that the occupant has woken up, a wakeup counter may be incremented. This wakeup counter may then be used to determine whether the occupant has insomnia. The wakeup counter may be reset upon occurrence of a condition; for example, the wakeup counter may be reset after the occupant has ceased resting on the mattress for at least a predetermined period of time. Generally, a higher number of wakings is interpreted as a higher likelihood of insomnia.

In at least some embodiments, the techniques for detecting insomnia described above may be used by one or more of the processors to generate an insomnia likelihood score which indicates the likelihood that the occupant has insomnia. In at least some embodiments, this insomnia likelihood score may be expressed as a probability. In some embodiments, if the insomnia likelihood score exceeds a threshold, then the processor may determine that an occupant has insomnia.

Narcolepsy Detection

In at least some embodiments, the one or more processor(s) may be configured to detect narcolepsy. Narcolepsy is a sleep disorder in which a person has an extreme tendency to fall asleep. More specifically, narcolepsy is a neurological disorder which is caused by the brain's inability to regulate sleep-wake cycles normally.

In at least some embodiments, narcolepsy may be detected at step 904 of the method 900 of FIG. 9 by one or more processors associated with the sleep system 100 based on sleep onset latency for an occupant. A method 500 for determining sleep onset latency is described in greater detail above with reference to FIG. 5 and, in particular, with reference to step 508.

In at least some embodiments, sleep onset latency may be compared to one or more predetermined thresholds to determine whether the occupant has narcolepsy. The predetermined threshold may effectively indicate a sleep onset latency which is considered too short. In some embodiments, if the sleep onset latency is less than the threshold (i.e. if it takes too little time for the occupant to fall asleep), then the processor may determine that occupant may have narcolepsy. By way of example, a threshold of 10 minutes may be used in some embodiments. In other embodiments, a threshold of 5 minutes may be used. In yet further embodiments, multiple thresholds (e.g. 5 minutes and 10 minutes) may be used and each of these thresholds may suggest likelihood that the occupant has narcolepsy. For example, if the sleep onset latency is below the lower threshold (e.g. 5 minutes), then the processor may determine that it is more likely that the occupant has narcolepsy than if the sleep onset latency is between the lower threshold and the higher threshold (e.g. 10 minutes), which also signifies a possibility of narcolepsy. Accordingly, in at least some embodiments, the processor may quantify the likelihood that the occupant has narcolepsy based on the sleep onset latency. For example, the likelihood that the occupant has narcolepsy may be expressed as a probability.

Other indicators of narcolepsy may be used instead of or in addition to the sleep onset latency in order to detect narcolepsy. For example, in some embodiments, the processor may identify the average time for the occupant to transition from NREM stage 1 sleep to REM sleep and may use this average time to detect narcolepsy. For example, if the average time is less than a threshold (e.g. 20 minutes), then the processor may determine that the occupant likely has narcolepsy. The times at which the occupant entered and exited sleep stages may be determined in the manner described above with reference to FIG. 5.

Similarly, the amount of time an occupant spends in NREM stage 1 before progressing to the next sleep stage may also be considered by the processor when detecting narcolepsy. For example, if the average time spent in a NREM stage 1 cycle is is less than a predetermined threshold, then the processor may determine that the occupant likely has narcolepsy (i.e. it may detect narcolepsy).

In at least some embodiments, the techniques for detecting narcolepsy described above may be used by one or more of the processors to generate a narcolepsy likelihood score which indicates the likelihood that the occupant has narcolepsy. In at least some embodiments, this narcolepsy likelihood score may be expressed as a probability. In some embodiments, if the narcolepsy likelihood score exceeds a threshold, then the processor may determine that an occupant has narcolepsy.

Sleep Apnea Detection

In at least some embodiments, one or more of the processor(s) may be configured to detect sleep apnea at step 904 of the method 900 of FIG. 9. In some embodiments, the processor may further be configured to detect a sleep apnea classification type. Sleep apnea is a sleep disorder in which an occupant experiences pauses in breathing or instances of infrequent or shallow breathing during sleep. The pauses may be referred to as apnea and the abnormally shallow breathing events may be referred to as hypoapnea.

Sleep apnea may, in some embodiments, be classified as either obstructive sleep apnea (OSA) or central sleep apnea (CSA). That is, a processor may determine whether an occupant of the sleep system 100 suffers from OSA and/or whether the occupant of the sleep system 100 suffers from CSA.

OSA is more common than CSA. Central sleep apnea is a neurological condition which occurs when a person's brain does not send the appropriate signals to the muscles which control breathing. This may be contrasted with OSA which is caused due to an obstruction of the upper airway.

In at least some embodiments, sound may be used by a processor to detect sleep apnea. More particularly, in at least some embodiments, an electrical signal (which may be referred to as an audio signal) representing received sound waves may be generated by a microphone 334 associated with the sleep system 100. Based on this electrical signal, a processor may determine whether an occupant has sleep apnea. In at least some embodiments, the processor may determine whether the electrical signal includes snoring and/or gasping events. In at least some embodiments, the processor may perform audio processing on the electrical signal to distinguish non-apnea snoring (i.e. snoring which is not caused by sleep apnea, which may be referred to as normal snoring) from apnea-caused snoring (i.e. from snoring caused by sleep apnea). The signal from the microphone is, in at least some embodiments, converted into the frequency domain through the use data processing techniques such as fast Fourier transforms, wavelet analysis, or linear predictive coding. Cut off filters and bandpass filters may be used to narrow the frequency range, such as 70-2000 Hz, where snoring and breathing typically occur. Numerous techniques can be used by a processor to identify snoring/breathing sounds that are characteristic of OSA or CSA. For example, the data can be characterized with a spectral envelope determined using linear prediction autoregressive modeling. Formant frequencies can be determined by finding the local maxima of the spectra envelope. The formant frequencies of OSA patients typically have greater variability in both snoring and breathing, so identifying these frequencies can be used by the processor to determine the presence of OSA. Other techniques involve looking at the frequency characteristics of the snoring. Simple snoring has a spectrum characterized by a fundamental frequency with harmonics, whereas OSA snoring has a spectrum centered around a fundamental frequency without harmonics. To distinguish between these two types of snoring, in some embodiments, the processor may consider the ratio of the power above 800 Hz to the power below 800 Hz in the electrical signal generated by the microphone. OSA snoring typically produces sound with higher power above 800 Hz, so ratios greater than one may represent OSA in some embodiments. Identification of intra-snoring pitch jumps can also be indicative of OSA. Also, OSA snoring typically has peak intensity above 1000 Hz, while simple snoring typically has a peak intensity between 100-300 Hz. Other techniques may utilize hidden Markov models or higher order statistics for analysis of the sound data to determine snoring/breathing sounds and those that are distinct for OSA. Thus, in at least some embodiments, the processor may detect apnea events in the audio signal. In at least some embodiments, an apnea event may be characterized by loud snoring or gasping followed by a quiet period of twenty to thirty seconds in duration and the processor may analyze the audio signal to detect such characteristics.

Apnea events typically occur when an occupant is in certain stages of sleep. More particularly, apnea events typically occur during NREM stage 3 and REM sleep. In some embodiments, to reduce audio processing and/or to improve the accuracy of the detection, the processor may be configured to consider the sleep stage of the occupant in the sleep apnea analysis. For example, the sleep stage of the occupant may be determined in the manner described above with reference to the method 500 of FIG. 5, and in particular with reference to step 504, and may be used to facilitate the detection of sleep apnea. In at least some embodiments, sleep stage information may be used, by the processor, to identify periods of interest within the audio signal. The periods of interest are periods in which sleep apnea is more likely to occur. In at least some embodiments, the periods of interest may be periods where the occupant has been determined to be in either NREM stage 3 or REM sleep.

The identification of periods of interest may be done before processing the audio signal (which may reduce the amount of processing) or may be done after the audio is processed (in which case the audio processing may not be reduced, but the accuracy of the detection may be improved). Where the periods of interest are identified before the audio signal is processed, the processor may analyze portions of the audio signal corresponding to the periods of interest but may ignore the portions of the audio signal that do not correspond to the periods of interest. If, instead, the audio processing is done after the audio signal is analyzed (e.g. after the processor has already identified possible apnea events), then in some embodiments the periods of interest may be used to filter these apnea events. For example, an apnea event identified during the sleep analysis may be determined by the processor to be a non-apnea event if it did not occur during a period of interest.

Furthermore, in some embodiments, the occupant's respiratory rate patterns may be used by a processor in the sleep apnea detection. Apnea episodes have distinct breathing patterns—in OSA, typically shallow breathing or a pause in breathing for a period from seconds to minutes will occur, followed by a large gasp, followed by a return to normal breathing until the next apnea episode. Shallow breathing or no breathing will manifest as a lower than normal respiration amplitude possibly paired with inconsistent or lower respiration rates, while a gasp will produce a larger than normal respiration amplitude. Identify this unique patterns of breathing can be used to identify apnea events. No breathing will result in a zero respiration rate. Force sensors can be used to confirm that the occupant is still in bed during periods of zero respiration. In CSA, the occupant's respiratory rate will be zero for period of time, followed by a return to normal breathing. The respiratory rate may be determined in the manner described above with reference to the method 700 of FIG. 7. The respiratory rate may be used to correlate the audio in the audio signal to the occupant's breathing pattern. The audio signal and respiration rate may be used together to distinguish normal breathing/snoring from OSA and CSA. The number of apnea events is tabulated over a period of time to determine the severity of the disorder.

In some embodiments, the respiratory rate may also be used by a processor to identify which of two occupants is snoring. More particularly, since the audio signal may contain sleep apnea events (such as snoring and/or gasping) associated with more than one occupant, in some embodiments, the audio signal may be co-related to the respiration rate to select the occupant who is likely associated with the sleep apnea event.

In some embodiments, a single apnea event may not, itself, cause the processor to determine that the occupant has sleep apnea. For example, in some embodiments, the processor will count the number of sleep apnea events and will only determine that sleep apnea has been detected if at least a predetermined number of sleep apnea events are detected. In some embodiments, the processor will detect sleep apnea when at least a predetermined number of sleep apnea events are detected over a predetermined period of time. For example, in one embodiment, sleep apnea may be detected if five or more sleep apnea events are detected in an hour. This is known as the apnea-hypopnea index (AHI) and is a measure of how often an individual suffering from OSA stops breathing over a certain amount of sleep time (usually per one hour of sleep time). Measurements of AHI under 5 are normal, 5-15 is mild, 15-30 is moderate, and above 30 is severe.

In some embodiments, other information may also be used by the processor to detect sleep apnea. For example, in some embodiments, the processor may determine a sleep apnea risk level associated with an occupant and may use the sleep apnea risk level when detecting sleep apnea. The sleep apnea risk level may, for example, be determined by the processor based on one more occupant characteristics defined in a user profile for the occupant. The user profile may be input to the sleep system 100 and/or an associated device (such as a mobile device) using an input interface such as a keyboard. After this information is input, it may be stored in memory 372 associated with the sleep system or device. The occupant characteristics used in the sleep apnea sleep apnea determination may, for example, include the age, weight, physical fitness level, height and/or sex of the occupant. In some embodiments, the occupant characteristics include an indication of whether the occupant suffers from dry mouth and/or morning headaches, since these are both factors that may be related to sleep apnea.

Thus, the occupant characteristics may be used to determine a sleep apnea risk level of the occupant and the sleep apnea risk level may be used when determining whether the occupant has sleep apnea. The greater the sleep apnea risk level, the more likely the occupant will be determined to have sleep apnea.

In at least some embodiments, the techniques for detecting sleep apnea described above may be used by one or more of the processors to generate a sleep apnea likelihood score which indicates the likelihood that the occupant has sleep apnea. In at least some embodiments, this sleep apnea likelihood score may be expressed as a probability. In some embodiments, if the sleep apnea likelihood score exceeds a threshold, then the processor may determine that an occupant has sleep apnea.

Bruxism Detection

In at least some embodiments, the one or more processor(s) may be configured to detect sleep bruxism. Bruxism is a disorder in which a person excessively grinds their teeth and/or excessively clenches their jaw. Sleep bruxism is a form of bruxism that occurs during sleep.

In at least some embodiments, sleep bruxism may be detected at step 904 of the method 900 of FIG. 9 by one or more processors associated with the sleep system 100. In at least some embodiments, sound may be used by a processor to detect bruxism. More particularly, in at least some embodiments, an electrical signal (which may be referred to as an audio signal) representing received sound waves may be generated by a microphone 334 associated with the sleep system 100. Based on this electrical signal, a processor may determine whether an occupant has bruxism. In at least some embodiments, the processor may determine whether the electrical signal includes teeth grinding events. The identification of bruxism by the processor may involve a pattern-based analysis. More particularly, the processor may compare the audio represented in the audio signal to a typical pattern resulting from bruxism.

Based on the audio-analysis, the processor may generate a bruxism likelihood score which indicates the likelihood that the occupant has bruxism. In at least some embodiments, this score may be expressed as a probability. In some embodiments, if the bruxism likelihood score exceeds a threshold, then the processor may determine that an occupant has bruxism.

In some embodiments, other information may also be used by the processor to detect sleep bruxism. For example, in some embodiments, the processor may determine a bruxism risk level associated with an occupant and may use the bruxism risk level when detecting sleep bruxism. The bruxism risk level may, for example, be determined by the processor based on one more occupant characteristics defined in a user profile for the occupant. The user profile may be input to the sleep system 100 and/or an associated device (such as a mobile device) using an input interface such as a keyboard. After this information is input, it may be stored in memory 372 associated with the sleep system or device. By way of example, in some embodiments, the user profile may indicate whether an occupant complains of jaw pain. In some embodiments, when the occupant complains of jaw pain, the bruxism risk level is greater than if the occupant did not complain of jaw pain. When the occupant complains of jaw pain, the bruxism likelihood score may be increased by the processor; for example, the bruxism likelihood score may be increased by 30% in some embodiments. In some embodiments, a threshold used to detect bruxism may be adjusted by the processor based on the bruxism risk level. For example, the threshold may be reduced when the occupant complains of jaw pain so that bruxism is more easily detected for such an occupant.

Delayed Sleep Phase Syndrome Detection

In at least some embodiments, the one or more processor(s) may be configured to detect delayed sleep phase syndrome (DSPS). DSPS, which may also be referred to as delayed sleep phase disorder (DSPD) or delayed sleep-phase type (DSPT) is a sleep disorder which affects the timing of a person's sleep. More particularly, people with DSPS often require a relatively large period of time to fall asleep and they often have difficulty waking up in the morning.

In at least some embodiments, DSPS may be detected at step 904 of the method 900 of FIG. 9 by one or more processors associated with the sleep system 100 based on sleep onset latency for an occupant. A method 500 for determining sleep onset latency is described in greater detail above with reference to FIG. 5 and, in particular, with reference to step 508.

In at least some embodiments, sleep onset latency may be compared (at 904 of the method 900 of FIG. 9) to a predetermined threshold to determine whether the occupant has DSPS. The predetermined threshold may effectively indicate a sleep onset latency which is considered too long. In some embodiments, if the threshold is exceeded (i.e. if it takes too long for the occupant to fall asleep), then the processor may determine that occupant may have DSPS. In at least some embodiments, the processor may quantify the likelihood that the occupant has DSPS based on the sleep onset latency. For example, the likelihood that the occupant has DSPS may be expressed as a probability.

In some embodiments, the processor may be configured to determine that the occupant has DSPS if the occupant experiences a sleep onset latency which is too long for at least a predetermined number of days and/or nights. In some embodiments, the processor may be configured to determine that the occupant has DSPS if the occupant experiences a sleep onset latency which is too long for at least a predetermined number of consecutive sleeps. That is, when the processor detects that the sleep onset latency exceeds a threshold, it may initiate a counter which counts the number of consecutive sleeps having excessive sleep onset latency. This counter may be incremented for each subsequent sleep having excessive sleep onset latency and may, in some embodiments, be reset after a sleep without excessive sleep onset latency. When the counter reaches a threshold, the processor may determine that the occupant has DSPS.

The processor may also, in at least some embodiments, consider the time when an occupant went to bed and/or the time when the occupant woke up when detecting DSPS. DSPS sufferers tend to go to bed late and wake up late.

In at least some embodiments, the ASPS detection may be performed based on the time of day when an occupant went to bed, fell asleep, woke up and/or got out of bed. As noted in the discussion of FIG. 3 above, in some embodiments, the sleep system 100 may include timing circuitry or timing components which are configured to track the time of day and/or the date. That is, in at least some embodiments, the sleep system may include a clock. The clock may be associated with one or more of the processors and may, in at least some embodiments, be provided on one or more of the processors. The processor may use timing information obtained from the clock to detect DSPS. More particularly, the timing information may be used to track when an occupant went to bed, fell asleep, woke up and/or got out of bed. Techniques of identifying when an occupant went to bed, fell asleep and woke up were described above with reference to the method 500 of FIG. 5. The sleep system may identify when an occupant got up from bed using a technique that operates in reverse to the technique for identifying when the occupant went to bed. For example, when a reading on the force sensors changes from a state where at least one of the force sensors in a sensor set 150, 152 is reading a relatively large amount of force to a state when none of the force sensors in that same sensor set 150, 152 are reading a relatively large amount of force, then the processor may determine that an occupant has gotten up from bed.

In some embodiments, temperature readings from a body temperature sensor may be used to detect when an occupant has gotten up from bed. More particularly, the processor may detect a decline in temperature sensor as the readings adjust from representing a body temperature to representing a room temperature. The processor may interpret such declines in temperature readings obtained from a body temperature sensor 122 as an indication that an occupant is or may have gotten up from bed.

In some embodiments, the processor may detect when an occupant has gone to bed based on data from one or more of the force sensors 120a-120h in a sensor set 150, 152. Then the processor may determine the time when the occupant went to bed using the clock associated with the processor. The processor may compare the time when the occupant went to bed to a predetermined threshold and may determine that the occupant went to bed late if the time when the occupant went to bed is greater than a predetermined time threshold. Otherwise (i.e. if the time when the occupant went to bed is less than the time threshold), then the processor may determine that the occupant did not go to bed late. The processor may interpret the occupant going to bed late as an indication that the occupant may have DSPS.

In some embodiments, to detect DSPS, the processor may also monitor when the occupant wakes up. This may be done, for example, by monitoring whether the occupant is asleep or awake in the manner described above with reference to FIG. 5. The processor may compare the time when the occupant woke up to another predetermined time threshold to determine whether the occupant has woken up late. When the time when the occupant woke up is greater than this threshold, then the processor may determine that the occupant has woken up late. When the time when the occupant woke up is less than this threshold, then the processor may determine that the occupant has not woken up late.

In response to determining that the occupant has went to bed late and woken up late, the processor may increment a counter. In some embodiments, the counter tracks the number of days that the occupant went to bed late and got up late. In some embodiments, the counter tracks the number of consecutive sleeps that the occupant went to bed late and got up late (i.e. the number of consecutive times that the occupant was sleeping in the mattress and went to bed late and woke up late). This counter may be reset in some embodiments when a predetermined trigger is detected. This trigger may, for example, occur when an occupant has gone to bed early or at a normal time (which may be determined based on a threshold) for a predetermined number of nights and/or has gotten up early for at least a predetermined number of nights.

In at least some embodiments, the processor may determine that an occupant has DSPS by comparing the counter to one or more predetermined count thresholds. If the counter exceeds the threshold, DSPS may be detected.

In at least some embodiments, sleep onset latency may be used by the processor together with at least one of the time when a user went to bed, fell asleep, woke up and/or went to bed, to detect DSPS.

In at least some embodiments, the processor may also consider sleep quality when determining whether an occupant has DSPS. Sleep quality may, for example, be determined based on the number of times the occupant wakes up during their sleep session and/or the amount of time elapsed between when the occupant falls asleep and when they wake up. A lower number of wakeups results in a higher sleep quality. In at least some embodiments, since high sleep onset latency may be an indicator for both DSPS and insomnia, the processor may be configured to distinguish between these two conditions based on the sleep quality. Insomnia sufferers tend to have a low sleep quality, but DSPS sufferers do not tend to have a low sleep quality. Thus, a measure of the sleep quality may be compared to one or more predetermined thresholds to determine whether an occupant has or is likely to have DSPS and/or whether the occupant has or is likely to have insomnia.

In at least some embodiments, the techniques for detecting DSPS described above may be used by one or more of the processors to generate a DSPS likelihood score which indicates the likelihood that the occupant has DSPS. In at least some embodiments, this DSPS likelihood score may be expressed as a probability. In some embodiments, the probability may be based on the number of consecutive sleeps during which the occupant experienced excessive sleep onset latency. For example, when the number of consecutive sleeps with excessive sleep onset latency reaches a first predetermined threshold, then the processor may determine that the likelihood of DSPS is at a first level (e.g. 60%). When the number of consecutive sleeps with excessive sleep onset latency reaches a second predetermined threshold, then the processor may determine that the likelihood of DSPS is at a second level (e.g. 70%). A greater number of thresholds may be used in other embodiments.

Advanced Sleep Phase Syndrome Detection

In at least some embodiments, the one or more processor(s) may be configured to detect advanced sleep phase syndrome (ASPS). ASPS, which may also be referred to as advanced sleep phase disorder (ASPD) or advanced sleep phase type (ASPT), is a sleep disorder in which a person feels very sleepy and goes to bed during the early evening and wakes up very early in the morning.

In at least some embodiments, ASPS may be detected at step 904 of the method 900 of FIG. 9 by one or more processors associated with the sleep system 100. In at least some embodiments, the ASPS detection may be performed based on the time of day when an occupant went to bed, fell asleep, woke up and/or got out of bed.

As noted in the discussion of FIG. 3 above and in the discussion of DSPS detection, in some embodiments, the sleep system 100 may include timing circuitry or timing components which allow a processor to identify a time when an occupant went to bed, fell asleep and woke up. Techniques for identifying when the occupant went to bed, fell asleep and woke up were described above with reference to FIG. 5 and techniques for identifying when an occupant got up from bed were described with reference to the DSPS detection described above.

In some embodiments, the processor may detect when an occupant has gone to bed based on data from one or more of the force sensors 120a-120h in a sensor set 150, 152. Then the processor may determine the time when the occupant went to bed using the clock associated with the processor. The processor may compare the time when the occupant went to bed to a predetermined threshold and may determine that the occupant went to bed early if the time when the occupant went to bed is less than a predetermined time threshold. Otherwise (i.e. if the time when the occupant went to bed is greater than the time threshold), then the processor may determine that the occupant did not go to bed early. In some embodiments, the time threshold may be in the range of 6 to 8 pm. The processor may interpret the occupant going to bed early as an indication that the occupant may have ASPS.

In some embodiments, to detect ASPS, the processor may also monitor when the occupant wakes up. This may be done, for example, by monitoring whether the occupant is asleep or awake in the manner described above with reference to FIG. 5. The processor may compare the time when the occupant woke up to another predetermined time threshold to determine whether the occupant has woken up early. When the time when the occupant woke up is less than this threshold, then the processor may determine that the occupant has woken up early. When the time when the occupant woke up is greater than this threshold, then the processor may determine that the occupant has not woken up early.

In response to determining that the occupant has went to bed early and woken up early, the processor may increment a counter. In some embodiments, the counter tracks the number of days that the occupant went to bed early and got up early. In some embodiments, the counter tracks the number of consecutive sleeps that the occupant went to bed early and got up early (i.e. the number of consecutive times that the occupant was sleeping in the mattress and went to bed early and woke up early). This counter may be reset in some embodiments when a predetermined trigger is detected. This trigger may, for example, occur when an occupant has gone to bed late or at a normal time (which may be determined based on a threshold) for a predetermined number of nights and/or has gotten up late for at least a predetermined number of nights.

In at least some embodiments, the processor may determine that an occupant has ASPS by comparing the counter to one or more predetermined count thresholds. If the counter exceeds the threshold, ASPS may be detected.

In some embodiments, the processor may consider other information instead of or in addition to the time when an occupant went to bed or got up from bed. For example, in some embodiments, the processor may determine an awake latency based on data from one or more of the force sensors. The awake latency represents the elapsed time between when an occupant woke up and when they got up from the mattress. That is, the awake latency indicates the time when the occupant remained in bed awake after a sleep period. In at least some embodiments, the awake latency may be compared by the processor to one or more thresholds to determine whether the awake latency is too long. In at least some embodiments, the determination of whether an occupant has ASPS is based on the awake latency. A long awake latency may, therefore, be interpreted by the processor as an indication that an occupant has or is likely to have ASPS.

In at least some embodiments, the techniques for detecting ASPS described above may be used by one or more of the processors to generate an ASPS likelihood score which indicates the likelihood that the occupant has ASPS. In at least some embodiments, this ASPS likelihood score may be expressed as a probability. In some embodiments, the probability may be based on the number of consecutive sleeps during which the occupant has gone to bed early and/or woken up early. For example, when the number of consecutive sleeps during which the occupant has gone to bed early and/or woken up early reaches a first predetermined threshold, then the processor may determine that the likelihood of ASPS is at a first level (e.g. 60%). When the number of consecutive sleeps during which the occupant has gone to bed early and/or woken up early reaches a second predetermined threshold, then the processor may determine that the likelihood of ASPS is at a second level (e.g. 70%). A greater number of thresholds may be used in other embodiments.

Periodic Limb Movement Disorder

In at least some embodiments, the one or more processor(s) may be configured to detect periodic limb movement disorder (PLMD). PLMD is a sleep disorder in which a person moves limbs involuntarily during sleep.

In at least some embodiments, PLMD may be detected at step 904 of the method 900 of FIG. 9 by one or more processors associated with the sleep system 100. In at least some embodiments, the PLMD detection may be performed by monitoring movements in a leg region of the mattress 101. The leg region of the mattress is a region which is associated with an occupant's legs. Accordingly, in at least some embodiments, lower body force sensors 120*g*, 120*h* may be used to detect PLMD. That is, the processor may monitor for movement in the leg region of the mattress by monitoring the lower body force sensors 120*g*, 120*h*. The processor may quantify leg movement based on readings obtained from the lower body force sensors 120*g*, 120*h*. More particularly, the processor may determine a measure of leg movement based on data from one or more force sensors that are located in the leg region (i.e. from the lower body force sensors 120*g*, 120*h*) and may detect PLMD based on the measure of leg movement.

In some embodiments, the measure of leg movement may be a measure of the average number of leg movements over a predetermined period of time (e.g. movements per hour). If the average number of leg movements exceeds a predetermined threshold, then the processor may determine that the occupant has or is likely to have PLMD. Movements may be detected in the manner described above with reference to 404 of FIG. 4.

PLMD movements often occur in NREM stage 1 sleep. Accordingly, in at least some embodiments, the processor may only consider movements of the legs that are observed during NREM stage 1 sleep when monitoring for PLMD. That is, movements which occur during a waking period, during REM sleep, during NREM stage 2 sleep or during NREM stage 3 sleep may be disregarded when detecting PLMD. Methods of identifying sleep stage are described in detail above with reference to FIG. 5.

In at least some embodiments, the techniques for detecting PLMD described above may be used by one or more of the processors to generate a PLMD likelihood score which indicates the likelihood that the occupant has PLMD. In at least some embodiments, this PLMD likelihood score may be expressed as a probability. In some embodiments, the probability may be based on the average number of leg movements during a predetermined period of time. For example, when the average number of leg movements reaches a first predetermined threshold, then the processor may determine that the likelihood of PLMD is at a first level (e.g. 60%). When the average number of leg movements reaches a second predetermined threshold, then the processor may determine that the likelihood of PLMD is at a second level (e.g. 70%). A greater number of thresholds may be used in other embodiments.

Sleep Walking Detection

In at least some embodiments, the one or more processor(s) may be configured to detect sleep walking. Sleep walking is a sleep disorder where a sleeping person performs activities that are usually performed during a full state of consciousness.

In at least some embodiments, sleep walking may be detected at step 904 of the method 900 of FIG. 9 by one or more processors associated with the sleep system 100. In at least some embodiments, the sleep walking detection may be performed based on the time of day when an occupant got out of bed.

As noted in the discussion of FIG. 3 above, in some embodiments, the sleep system 100 may include timing circuitry or timing components which are configured to track the time of day and/or the date. That is, in at least some embodiments, the sleep system may include a clock. The clock may be associated with one or more of the processors and may, in at least some embodiments, be provided on one or more of the processors. The processor may use timing information obtained from the clock to track when an occupant got out of bed. Techniques of identifying when an occupant got out of bed are described in greater detail above in the discussion of detection of ASPS and these same techniques may be used for detecting when an occupant has gotten out of bed in order to detect sleep walking.

In some embodiments, the processor may log information (i.e. may store data in memory) indicating the times when an occupant got out of bed. In at least some embodiments, these times may later be presented to a user via a display and the user may indicate whether they recall getting out of bed at the indicated times. If the user does not recall at least a predetermined number of instances where they got out of bed, then the processor may determine that the user is likely to suffer from sleep walking.

In at least some embodiments, the techniques for detecting sleep walking described above may be used by one or more of the processors to generate a sleep walking likelihood score which indicates the likelihood that the occupant is a sleep walker. In at least some embodiments, this sleep walking likelihood score may be expressed as a probability.

Sleep Talking Detection

In at least some embodiments, the one or more processor(s) may be configured to detect sleep talking. Sleep talking occurs when a person talks aloud while asleep.

In at least some embodiments, sleep talking may be detected at step 904 of the method 900 of FIG. 9 by one or more processors associated with the sleep system 100. In at least some embodiments, sound may be used by a processor to detect sleep talking. More particularly, in at least some embodiments, an electrical signal (which may be referred to as an audio signal) representing received sound waves may be generated by a microphone 334 associated with the sleep system 100. Based on this electrical signal, a processor may determine whether an occupant talks in their sleep. In at least some embodiments, a frequency-based analysis may be performed on the audio signal to determine whether the audio signal includes sound associated with a human voice. Typically, humans speak at a frequency of 300 to 3500 Hz. In at least some embodiments, in detecting sleep talking, the processor may determine whether the audio signal includes sound at a frequency associated with a human voice.

Based on the audio-analysis, the processor may generate a sleep talking likelihood score which indicates the likelihood that the occupant talks in their sleep. In at least some embodiments, this score may be expressed as a probability. In some embodiments, if the sleep talking likelihood score exceeds a threshold, then the processor may determine that an occupant talks in their sleep.

Figure 13:
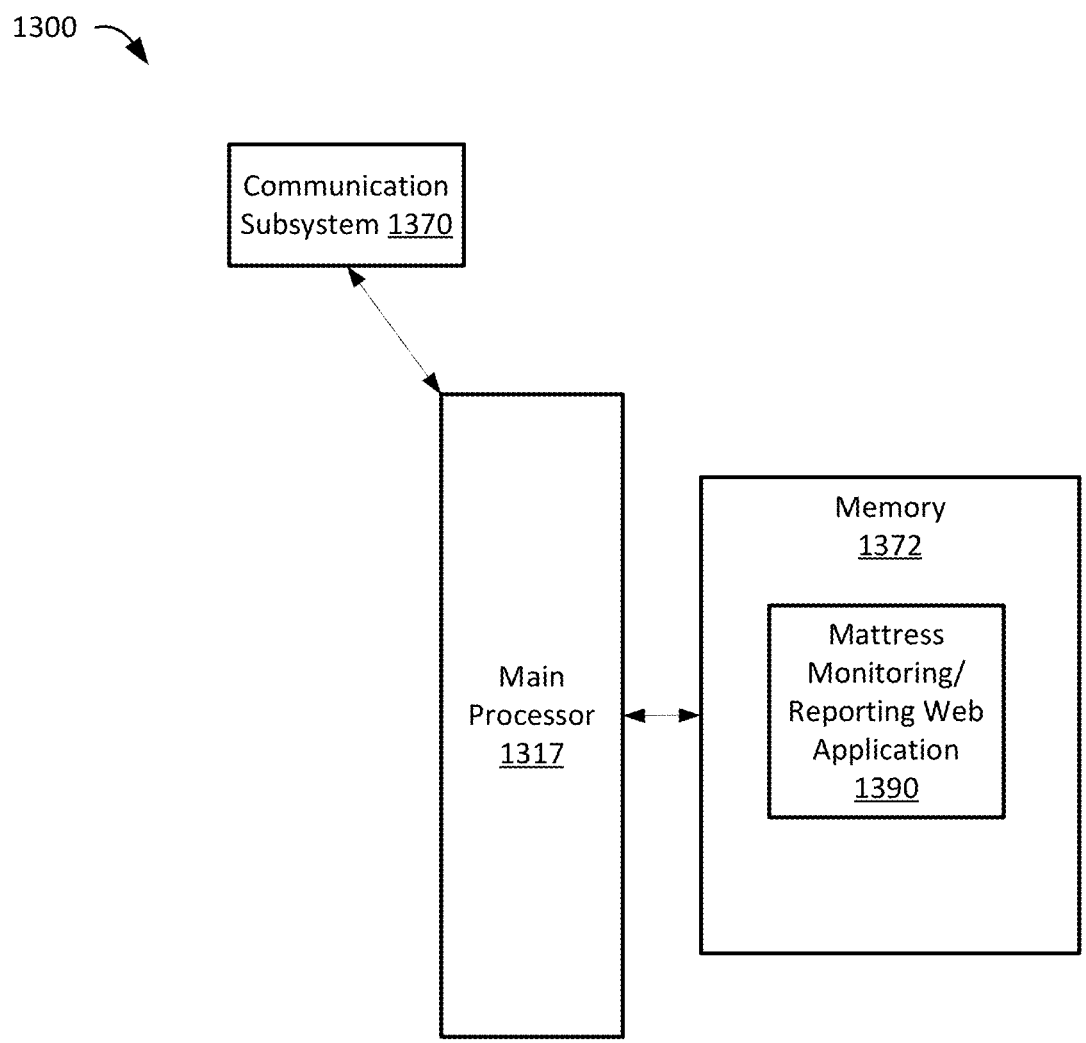
FIG. 13 is a block diagram of a server in accordance with example embodiments of the present disclosure.

In some embodiments, audio may be recorded in memory (for example, in a buffer) and audio containing sleep talking events may be recorded in a more permanent memory to allow a user to later listen to their sleep talking session. Playback may be provided either through a speaker associated with the sleep system 100 or on a speaker on a mobile device 1200 (FIG. 12) or on a client device accessing a web server 1300 (FIG. 13).

Bedwetting Detection

In at least some embodiments, the one or more processors may be configured to detect bedwetting, which may also be referred to as nocturnal enuresis or nighttime urinary incontinence. This is a condition in which a person urinates in bed.

In at least some embodiments, bedwetting may be detected at step 904 of the method 900 of FIG. 9 by one or more processors associated with the sleep system 100. In at least some embodiments, sound may be used by a processor to detect bed wetting. More particularly, in at least some embodiments, an electrical signal representing a humidity level may be generated by a body humidity sensor 124. In some such embodiments, the processor may compare the humidity level obtained from the body humidity sensor 124 to one or more predetermined thresholds to detect bedwetting. In some embodiments, when the humidity level exceeds one of the thresholds, then the processor may determine that bedwetting has occurred.

In at least some embodiments, the processor may also consider whether the occupant is in the bed and/or whether the occupant is asleep when determining bedwetting. Methods for detecting presence of an occupant (i.e. whether the occupant is in the bed) and whether the occupant is asleep are described in greater detail with reference to FIG. 5. Excessive humidity occurring when an occupant is not in bed and/or is not asleep may be caused by another source, apart from bedwetting. Accordingly, in at least some embodiments, such humidity readings are ignored by the processor when detecting bedwetting.

The processor may, in some embodiments, generate a bedwetting likelihood score which indicates the likelihood that the occupant wets the bed. In at least some embodiments, this score may be expressed as a probability. In some embodiments, if the bedwetting likelihood score exceeds a threshold, then the processor may determine that an occupant is a bed-wetter.

Sleep Score Determination

As noted above, in at least some embodiments, one or more processors associated with the sleep system 100 may be configured to determine sleep state information associated with one or more occupants of the sleep system 100. In at least some embodiments, this sleep state information may include one or more sleep scores. The sleep score may, for example, quantify the quality, efficiency and/or consistency of an occupant's sleep. Methods of determining sleep scores, such as a sleep efficiency score and/or a sleep consistency score, will now be discussed.

Sleep Efficiency Score

In at least some embodiments, one or more processors associated with the sleep system 100 may be configured to determine a sleep efficiency score. The sleep efficiency score provides a quantitative measure of quality and/or efficiency of sleep during a sleeping period. In some embodiments, this sleeping period may be a single night. That is, the sleep efficiency score may provide a quantitative measure of sleep quality during a single night of sleep. Thus, the metrics and measures described below may, in at least some embodiments, be determined based on data obtained during a single night's sleep.

The sleep efficiency score may be determined, by the processor, based on one or more of: the sleep onset latency, a subjective sleep quality metric, a sleep duration, a sleep efficiency metric, a number of sleep disturbances, an amount of time in a REM stage, and/or an amount of time in a deep sleep. In some embodiments, the sleep efficiency score may be determined as a weighted average of two or more of these metrics and measures.

The sleep onset latency is a measure of the difference between the time when an occupant attempted to fall asleep and the time when that occupant fell asleep. Methods of determining sleep onset latency are described with reference to 508 of FIG. 5.

Subjective sleep quality may, in at least some embodiments, be input by a user via an input interface associated with the sleep system and/or a mobile device associated with the sleep system. For example, a user may be presented with a prompt (which may be displayed on a display) to rate their sleep. Based on the input received from the user, the subjective sleep quality may be quantified.

Sleep duration may be determined by the processor and is a measure of the total amount of time that an occupant spent sleeping. That is, sleep duration is the amount of time that elapsed between the time when the occupant fell asleep and the time when the occupant woke up. Techniques for identifying when the occupant fell asleep and woke up are described above.

The sleep efficiency metric is also determined by the processor and may be based on the total amount of time that the occupant was in bed and the amount of time that the occupant spent sleeping. For example, the sleep efficiency metric may be the percentage of time in the bed that was spent sleeping. By way of example, in some embodiments, the processor may calculate the sleep efficiency metric as the dividend of the time spent sleeping divided by the total time in the mattress. Techniques for identifying when the occupant got into bed, fell asleep, woke up and got out of bed are described in greater detail above and the times associated with each of these events may be used to determine the sleep efficiency metric.

The number of sleep disturbances is a measure of the number of times an occupant wakes up during a sleep session (e.g. during the course of a night). In at least some embodiments, a sleep disturbance may be caused by an environmental factor, such as noise in the room where the occupant is sleeping, or it may not be caused by such environmental factors and may be part of that occupant's sleep routine (e.g. it may be caused by a sleep disorder such as sleep apnea). The number of sleep disturbances may be tracked by incrementing a counter each time a sleep disturbance is detected. The counter is occupant-specific. That is, sleep disturbances may be separately tracked for each occupant.

The amount of time in REM or a metric determined based on the amount of time in REM may also be used by the processor to determine the sleep efficiency score. The processor may determine the amount of time in REM by identifying periods in which an occupant is in the REM sleep stage and periods in which the user is not in the REM sleep stage (i.e. is either awake or in one of the non-REM stages) using the techniques described above with reference to FIG. 5. In at least some embodiments, the processor may determine a metric which is based on the total amount of time spent in the REM sleep stage during a single sleeping period or session (e.g. during a single night) as compared with the total amount of time spent in other sleep stages and/or the total amount of time spent in the bed. By way of example, in some embodiments, the metric may be determined as the dividend of the total time spent in REM during a sleep period divided by the total time spent in bed during the sleep period.

The amount of time in a deep sleep or a metric determined based on the amount of time in a deep sleep may be used by the processor to determine the sleep efficiency score. Certain sleep stages may be considered "deep sleep" stages. In at least some embodiments, only the NREM stage 3 sleep stage is considered to be a "deep sleep" stage. The processor may determine the amount of time in a deep sleep by identifying such sleep stages in the manner described above with reference to FIG. 5. In at least some embodiments, the processor may determine a metric which is based on the total amount of time spent during deep sleep stages during a single sleeping period or session (e.g. during a single night) as compared with the total amount of time spent in other sleep stages and/or the total amount of time spent in the bed. By way of example, in some embodiments, the metric may be determined as the dividend of the total time spent in deep sleep stages during a sleep period divided by the total time spent in bed during the sleep period.

Accordingly, a sleep efficiency score may be determined in the manner described above. In at least some embodiments, once determined, the sleep efficiency score may be stored in memory associated with the sleep system 100. In some embodiments, after the sleep efficiency score is determined, it may be output through an output interface associated with the sleep system 100. For example, the sleep efficiency score may be displayed on a display associated with the sleep system and/or an associated mobile device 1200.

Sleep Consistency Score

In at least some embodiments, one or more processors associated with the sleep system 100 may be configured to determine a sleep consistency score. The sleep consistency score provides a quantitative measure of quality and/or efficiency of sleep over an extended period of time. In some embodiments, this period of time may be a plurality of consecutive sleep sessions, such as a plurality of consecutive nights. For example, in some embodiments, this period of time may be the last two weeks.

The sleep consistency score may be determined, by the processor, based on one or more of: the sleep onset latency, a subjective sleep quality metric, a sleep duration, a sleep efficiency metric, a number of sleep disturbances, an amount of time in a REM stage, and/or an amount of time in a deep sleep. In some embodiments, the sleep efficiency score may be determined as a weighted average of two or more of these metrics and measures.

The sleep consistency score may also, in at least some embodiments, consider the variation in the time when an occupant goes to bed and/or wakes up. That is, the time when the occupant goes to bed and/or wakes up may be tracked over several sleep sessions (e.g. several nights) and the processor may determine a measure of the variability for one or both of these times. This measure of variability may be used by the processor when generating the sleep consistency score.

These metrics are described in greater detail above with reference when the method for determining a sleep efficiency score was described. The sleep consistency score differs from the sleep efficiency score in that it considers multiple sleep sessions.

In at least some embodiments, the sleep consistency score may be determined by comparing data from a most recent sleep session (e.g. from the previous night) to data from a plurality of prior sleep sessions. For example, a moving average over a predetermined number of sleep sessions may be used to determine the variability or standard deviation of one or more of the metrics noted above over the period.

Accordingly, a sleep consistency score may be determined in the manner described above. In at least some embodiments, once determined, the sleep consistency score may be stored in memory associated with the sleep system 100. In some embodiments, after the sleep consistency score is determined, it may be output through an output interface associated with the sleep system 100. For example, the sleep consistency score may be displayed on a display associated with the sleep system and/or an associated mobile device.

Mattress Health Information Determination

In at least some embodiments, one or more of the processors associated with the sleep system 100 may be configured to determine mattress health information. Mattress health information is information about the health of the mattress 101. The mattress health information may, for example, quantify the usage of the mattress over its lifetime (i.e. since manufacture of the mattress), quantify the usage of the mattress since a maintenance event (such as the usage since a last flip or rotation of the mattress, the usage since the last vacuuming of the mattress, the usage since the last change of bedding, the usage since the last deodorizing and/or disinfecting of the mattress), and/or may be based on the humidity level associated with the mattress.

In at least some embodiments, an alert may be generated based on such mattress health information. The alert may, for example, indicate to a user that maintenance is required.

Figure 10:
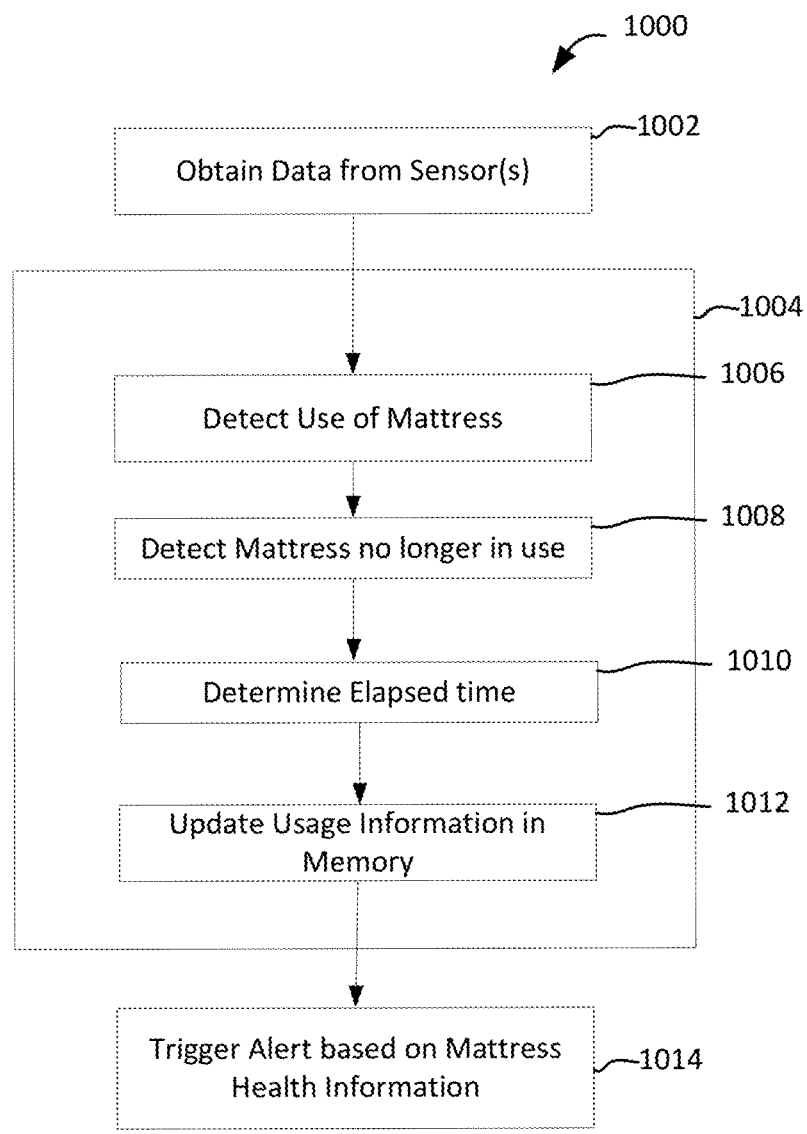
FIG. 10 is a flowchart of a method of triggering an alert based on mattress health information.

Referring now to FIG. 10, an example method 1000 for monitoring mattress health is illustrated in flowchart form. In at least some embodiments, one or more of the processors that are included in the sleep system 100 or in a server, system or device that is coupled to the sleep system may be configured to determine mattress health information for an occupant based on data obtained from one or more sensors embedded within the mattress 101. The one or more processors may include, for example, the main processor 117, the microprocessors 130a, 130b, a processor provided on an external peripheral of the type described above, a processor 1217 on a mobile device 1200 connected or connectable to the sleep system 100, a processor on a remote server connectable to the sleep system 100, and/or another processor associated with the sleep system 100.

More particularly, one or more memories associated with the one or more processors may include processor-executable instructions which, when executed, configure the processor to perform the method 1000. For example, in some embodiments, memory 372 associated with the main processor 117 may include such processor-executable instructions to configure the main processor 117 to perform the method 1000.

The method 1000 described below may be used to determine mattress health information. At 1002, the processor obtains data from one or more sensors that are embedded within the mattress. These sensors may include, for example, one or more force sensors 120a-120h and/or a humidity sensor 124.

At 1004, the processor determines mattress health information based on the data obtained from the one or more sensors.

In some embodiments, step 1004 may include a plurality of sub-steps which allow the processor to quantify mattress usage. That is, the processor may determine one or more numerical representations of the amount of usage of the mattress 101. As described above with reference to FIG. 1, in at least some embodiments, one or more force sensors may be embedded into the mattress and may be positioned within the mattress to sense presence of an occupant of the mattress. That is, the force sensors are positioned so that at least one of the force sensors is engaged when an occupant is lying in the mattress 101 in a typical sleeping position. In at least some such embodiments, the mattress usage may be quantified based on data from one or more of the force sensors.

More particularly, the force sensors may be used to detect whether the mattress is in use (at 1006). When the processor determines, based on data from the force sensor(s) that the mattress is in use, it may track the amount of time which the mattress is in use. That is, the processor may detect that the mattress is in use when an occupant goes to bed (i.e. when they enter the bed). When this happens, the processor may record the time when the occupant went to bed in memory associated with the processor.

The time when an occupant went to bed is the time when the occupant laid on the mattress after having previously not been on the mattress. As noted above, this time may be identified by the processor based on data from the force sensors 120a-120h. That is, when an occupant goes to bed (i.e. lays on the mattress 101), the processor identifies a large increase in the force measured on at least some of the force sensors. Thus, the processor may determine that an occupant enters the bed when the force measured at a predetermined number (which may be one in some embodiments) of the force sensors 120a-120h exceeds a predetermined threshold.

In some embodiments, a further check may be performed to confirm that the change in force was due to an occupant entering the mattress and not, for example, due to an object being placed on the mattress. For example, a temperature may be obtained from a temperature sensor 122 and compared to a threshold to determine that an occupant has entered the mattress. Furthermore, in at least some embodiments, the processor may require that at least a predetermined number of force sensors are engaged (e.g. are registering forces which exceed one or more thresholds) and/or may require that specific force sensors are engaged before determining that an occupant has entered the mattress. For example, if an upper body force sensor registers a force which exceeds a predetermined threshold, but a middle body force sensor does not register a force which exceeds a predetermined threshold, then the processor may determine that the occupant has not yet entered the bed; the force registered at the upper body force sensor may be caused by an object apart from a human occupant.

The sleep system 100 (and more particularly, a processor associated with the sleep system) may then detect that the mattress 101 is no longer in use at 1008. More specifically, the processor detects that the occupant has gotten up from bed. This may be detected, by the processor, using a technique that operates in reverse to the technique for identifying when the occupant went to bed. For example, when a reading on the force sensors changes from a state where at least one of the force sensors in a sensor set 150, 152 is reading a relatively large amount of force to a state when none of the force sensors in that same sensor set 150, 152 are reading a relatively large amount of force, then the processor may determine that an occupant has gotten up from bed.

In some embodiments, temperature readings from a body temperature sensor may be used to detect when an occupant has gotten up from bed. More particularly, the processor may detect a decline in temperature sensor as the readings adjust from representing a body temperature to representing a room temperature. The processor may interpret such declines in temperature readings obtained from a body temperature sensor 122 as an indication that an occupant is or may have gotten up from bed.

After detecting that an occupant has left the bed, the processor may determine, at 1010, the amount of time that the occupant was in the bed during their last sleep session. That is, the processor may determine the amount of time elapsed between when the mattress was detected to be in use and when the mattress was detected to be no longer in use.

The processor may then update (at 1012) one or more numerical representations of usage stored in memory associated with the processor. For example, in some embodiments, the memory may store one or more numerical representations of usage which indicate the usage of the mattress since a last maintenance event. One such numerical representation may be referred to as usage-since-maintenance information. The usage-since-maintenance information indicates usage of the mattress since a last maintenance event of a predetermined type. In some embodiments, the usage-since-maintenance information may indicate the usage of the mattress since it was last flipped and/or rotated. In some embodiments, the usage-since-maintenance information may indicate the usage of the mattress since it was last deodorized and/or disinfected. In some embodiments, the usage-since-maintenance information indicates the usage of the mattress since it was last vacuumed. In some embodiments, the usage-since-maintenance information indicates the usage of the mattress since the bedding (e.g. sheets) were last changed. The usage-since-maintenance information may indicate the usage of the mattress since other maintenance events in other embodiments. Further, it will be appreciated that the memory may store multiple types of usage-since-maintenance information and may separately track each type of such information. For example, the memory may store usage-since-maintenance information indicating usage since the last flip or rotation of the mattress and may store separate usage-since maintenance information indicating usage since the last time the bedding was changed.

In at least some embodiments, the processor may determine new usage-since-maintenance information by adding the amount of time elapsed between when the mattress was detected to be in use and when the mattress was detected to be no longer in use to the usage-since-maintenance information stored in memory. That is, the usage-since-maintenance stored in memory is updated to include usage from the most recent sleep session. The memory may then be updated to store the new usage-since-maintenance information.

In some embodiments, the numerical representations of usage stored in memory associated with the processor may include lifetime-usage information. The lifetime usage information indicates the total usage of the mattress since manufacture; that is, usage over the lifetime of the mattress. The lifetime-usage information is, in at least some embodiments, never reset since the lifetime-usage information acts as a type of odometer to track total usage of the mattress over its life. In at least some embodiments, after determining an amount of time that elapsed between when the mattress was detected to be in use and when the mattress was detected to no longer be in use, the processor may determine new lifetime-usage-information at 1010. The new lifetime-usage-information is determined by adding the amount of time elapsed between when the mattress was detected to be in use and when the mattress was detected to no longer be in use to the lifetime-usage information stored in memory. Then, at 1012, the processor may update the memory to store the new lifetime-usage information.

At 1014, an alert may be triggered based on the mattress health information. For example, an alert may be triggered based on the numerical representations of usage discussed above (i.e. the usage-since-maintenance information and/or the lifetime-usage information). More specifically, one or more of the numerical representations of usage may be compared, by the processor, to one or more predetermined thresholds (which may be stored in memory) and an alert triggered at 1014 based on the result. For example, when a threshold is exceeded, the alert may be generated.

The alert may, for example, be generated on an output interface associated with the sleep system 100, such as a display. Accordingly, in at least some embodiments, the processor is configured to output an alert via an output interface in response to determining that mattress maintenance is required.

In at least some embodiments, at 1014, usage-since-maintenance information is compared to an associated predetermined threshold. In at least some embodiments, the alert may be generated by the processor in response to determining that the usage-since-maintenance information exceeds the associated predetermined threshold. The predetermined threshold(s) compared to the usage-since-maintenance information represent time periods after which a maintenance event should be performed. Thus, by comparing the usage-since-maintenance information to its associated threshold, the processor determines whether mattress maintenance is required.

The thresholds that are used will depend on the nature of the usage-since-maintenance information being evaluated. For example, a threshold used to evaluate usage-since-maintenance information which indicates the amount of use since bedding was last changed may be in the range of forty to seventy hours. Similarly, a threshold used to evaluate usage-since-maintenance information which indicates the amount of use since a top cover of the mattress was washed may be in the range of eighty to one hundred and thirty hours. A threshold used to evaluate usage-since-maintenance information which indicates the amount of use since the mattress was deodorized, refreshed and/or disinfected may be in the range of forty to seventy hours. A threshold used to evaluate usage-since-maintenance information which indicates the amount of use since the mattress was vacuumed may be in the range of two hundred to two hundred and fifty hours. In some embodiments, the threshold used to evaluate usage-since-maintenance information which indicates the amount of use since the mattress was flipped and/or rotated may be in the range of one week to three months. In at least some embodiments, the threshold used by the processor to evaluate usage-since-maintenance information may depend on home long the mattress has been in use over its lifetime (e.g. it may depend on the lifetime-usage information). For example, in some embodiments, certain maintenance events may be required more frequently when the mattress is new. By way of example, more frequent flipping or rotation may be required when the mattress is new (e.g. flipping/rotation may be required weekly when new, but monthly when older). Similarly, in some embodiments, certain maintenance events may be required more frequency when the mattress is old (e.g. deodorizing and/or disinfecting may be more frequent when the mattress is older). Thus, in at least some embodiments, the processor may select a threshold to be used for evaluating usage-since-maintenance information based on the age of the mattress (e.g. based on the lifetime-usage information).

The nature of the alert that is generated may also depend on the type of usage-since-maintenance information which was found to exceed the associated threshold. For example, in some embodiments, when the usage-since-maintenance information suggests that it has been too long since the last flip and/or rotation, the alert may be a displayed message prompting a user to flip or rotate the mattress. The alert may, in other situations, prompt the user to: change the bedding, wash the top cover, deodorize, refresh and/or disinfect the mattress, and/or vacuum the mattress.

Where lifetime-usage information is obtained, this information may also be compared, at 1014, to an associated predetermined threshold. In some embodiments, in response to determining that the lifetime-usage information exceeds the predetermined threshold, an associated alert may be triggered. This alert may prompt the user to replace the mattress.

While the lifetime-usage information may not be reset, usage-since-maintenance information may be reset when the user completes an associated maintenance activity. For example, if the user changes the bedding, the usage-since-maintenance information which indicates the amount of time in which the bedding was in use may be reset. More particularly, usage-since-maintenance information may be reset by the processor when one or more predetermined reset conditions are detected. In some embodiments, an input interface may be provided on the sleep system 100 or an associated mobile device to allow a user to input instructions. In some embodiments, one or more of the predetermined reset conditions includes an instruction to reset specific usage-since-maintenance information. This instruction may be received via the input interface. For example, a user may use the input interface to inform the processor that the bedding has recently been changed, which may then cause the processor to reset the usage-since-maintenance information that tracks the amount of time that the bedding was in use.

In some embodiments, other reset conditions may be used. For example, in some embodiments, a flip of the mattress may be detected using the force sensors embedded into the mattress. In yet other embodiments (not shown) the sleep system 100 may include one or more orientation or acceleration sensors which may be used, by the processor, for detecting a mattress flip. Such sensors may include, for example, accelerometers, gyroscopes, magnetometers, etc.

"Flipping" the mattress and "rotating" the mattress are used herein to mean different actions. A mattress flip occurs when the side which is the upper side changes. That is, the side of the mattress that supports an occupant changes during a "flip" so that the side which supported the occupant before the flip no longer supports the occupant and is, instead, closer to the floor. In contrast, during a mattress rotation, the upper side does not lose its status as the upper side. More particularly, the side of the mattress which supported the occupant before the rotation continues to support the occupant after the rotation.

It will be appreciated that at least some of the sensors described above (e.g. the force sensor, accelerometers, gyroscopes, magnetometers, etc.) may be used to detect the orientation of the mattress. For example, the processor may determine which of the sides is currently the "upper" side based on data from one or more of these sensors. Furthermore, in some embodiments, the processor may determine which of the sides is currently a "headboard" side by analyzing data from one or more of these sensors. For example, headboard side may be determined based on the distribution of forces at the force sensors. In some embodiments, an input interface may be used to allow a user to specify which of the sides of the mattress is a top side and/or which of the sides is a headboard side.

To allow for mattress rotation, in at least some embodiments, the sensors embedded within the mattress may have rotational symmetry. An object is said to have rotational symmetry if it looks the same after a certain amount of rotation. A second order rotational symmetry means that the object looks the same after one hundred and eighty degrees of rotation. In a at least some embodiments, the force sensors that are embedded into the mattress and that are associated with the top side of the mattress are arranged to have a second order rotational symmetry to accommodate rotation of the mattress. It will be appreciated that the arrangement of force sensors illustrated in FIG. 1 did not have such rotational symmetry. However, the arrangement of FIG. 1 could be modified to have such rotational symmetry; for example, by including a third and fourth sensor set in addition to the first and second sensor sets 150, 152 illustrated in the example. The third and fourth sensor sets could be arranged so that they appear one hundred and eighty degrees out of rotational alignment with the first and second sensor sets. That is, if the third and fourth sensor sets were rotated one hundred and eight degrees, they would line up with the first and second sensor sets.

To allow for mattress flipping, sensors may be associated with both a top side of the mattress and a bottom side of the mattress. For example, force sensors may be located near the top side and other force sensors may be located near the bottom side. In some embodiments, the arrangement of the sensors on the top side is the same as the arrangement of the sensors on the bottom side.

As noted in the discussion of FIG. 1, in at least some embodiments, the mattress may be configured for use by two occupants. In some such embodiments, the usage information described above (such as the usage-since-maintenance information and/or the lifetime-usage information) may be separately tracked for each occupant. That is, usage may be separately tracked for each of two sides of the mattress. In some such embodiments, the memory may store first usage-since-maintenance information indicating total usage of a first side of the mattress since a last maintenance event and second usage-since-maintenance information indicating total usage of a second side of the mattress since the last maintenance event. The processor may be configured to modify the first usage-since-maintenance information based on detected usage of the first side of the mattress and to modify the second usage-since-maintenance information based on detected usage of the second side of the mattress. In some embodiments, the processor is configured to compare both the first usage-since-maintenance information and the second usage-since-maintenance information to a predetermined threshold and to generate the alert in response to determining that any one or both of the first usage-since-maintenance information and the second usage-since-maintenance information exceed the predetermined threshold. That is, if either side of the bed has been used too much since the maintenance event, then the alert may be triggered. In other embodiments, the usage-since-maintenance and lifetime-usage information may not be separately tracked for each occupant.

Furthermore, other sensors may be used obtain mattress health information and to generate associated alerts instead of or in addition to the force sensors. For example, in some embodiments, the sleep system 100 includes a humidity sensor 124 which may be embedded in the mattress or included in a peripheral. In at least some embodiments, the processor may generate an alert based on data obtained from the humidity sensor. For example, in some embodiments, the processor is configured to generate the alert if a humidity level obtained from the humidity sensor exceeds a threshold for at least a predetermined period of time. The threshold and/or the time may be selected to prevent mold growth.

Sleeping Condition Monitoring and Reporting

In at least some embodiments, one or more of the processors associated with the sleep system 100 may be configured to monitor sleeping conditions. More particularly, in some embodiments, the one or more processors associated with the sleep system 100 may be configured to determine sleep environment information. Sleep environment information is information about the sleeping conditions for an occupant. The sleep environment information may, for example, identify and/or evaluate conditions in the room in which the sleep system 100 is located. The sleep environment information and/or the conditions that are identified and/or evaluated based on the sleep environment information may, in some embodiments, be referred to as sleep hygiene information.

In at least some embodiments, an alert may be generated based on such sleep environment information. The alert may, for example, indicate to a user that the sleep environment should be improved.

Figure 11:
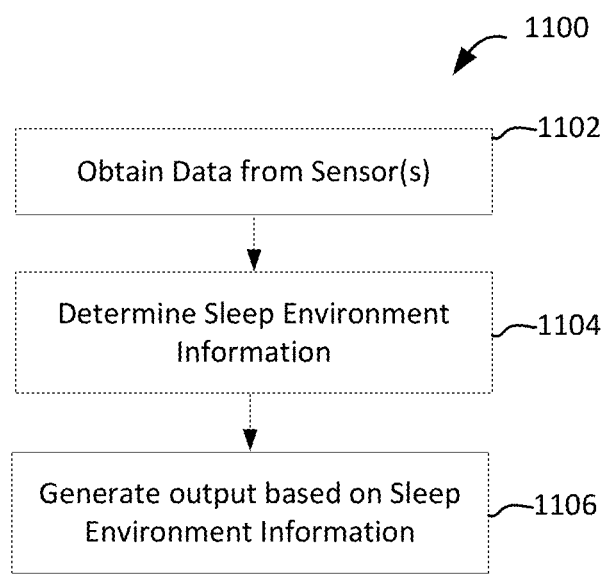
FIG. 11 is a flowchart of a method of determining sleep environment information.

Referring now to FIG. 11, an example method 1100 for determining sleep environment information is illustrated in flowchart form. In at least some embodiments, one or more of the processors that are included in the sleep system 100 or in a server, system or device that is coupled to the sleep system may be configured to determine sleep environment information for an occupant based on data obtained from one or more sensors embedded within the mattress 101 and data obtained from one or more sensors provided in a peripheral. The one or more processors may include, for example, the main processor 117, the microprocessors 130a, 130b, a processor provided on an external peripheral of the type described above, a processor on a mobile device connected or connectable to the sleep system 100, a processor on a remote server connectable to the sleep system 100, and/or another processor associated with the sleep system 100.

More particularly, one or more memories associated with the one or more processors may include processor-executable instructions which, when executed, configure the processor to perform the method 1100. For example, in some embodiments, memory 372 associated with the main processor 117 may include such processor-executable instructions to configure the main processor 117 to perform the method 1100.

The method 1100 described below may be used to determine sleep environment information. At 1102, the processor obtains data from one or more sensors embedded in the mattress 101 and also from one or more sensors provided in the peripheral which is external to the mattress (i.e. from the sleep environment sensing array 306). The peripheral may, for example, be coupled with a processor embedded into the mattress 101 via a wired or wireless connection.

In at least some embodiments, at 1102 data is obtained from one or more of: the force sensors 120a-120h embedded in the mattress, a dust sensor provided in the peripheral, a humidity sensor provided in the peripheral (humidity readings from this sensor may indicate a room humidity level), a light sensor provided in the peripheral (which may be used to provide light level readings for the room in which the mattress is located), a microphone provided in the peripheral (which may be used to provide ambient noise readings for the room in which the mattress is located), and/or a temperature sensor provided in the peripheral (which may be used to provide room temperature readings for the room in which the mattress is located).

At 1104, the data obtained from the sensors is used to determine sleeping environment information. More particularly, the sleeping environment information is obtained based on the data from one or more of the sensors embedded within the mattress and also based on data from one or more sensors provided in the peripheral.

The data from the force sensors embedded in the mattress may be used to determine whether an occupant is in bed and/or sleeping. Methods for determining whether the occupant is in bed and/or sleeping are described in greater detail above with reference to FIG. 5 and such methods may be performed by the processor during the method 1102 of FIG. 11. More particularly, the processor may detect a sleep session based on data obtained from the sensors embedded in the mattress. The sleep session may be said to occur when an occupant is in bed in some embodiments. In other embodiments, the sleep session may be said to occur when an occupant is asleep.

The sleep environment information may then be obtained based on data from one or more sensors in the peripheral which was obtained during the sleep session. Data obtained from the peripheral when a sleep session was not in progress may be discarded in at least some embodiments. That is, the sleep environment information may not consider data obtained from one or more of the sensors in the peripheral when a sleep session was not in progress.

As noted above, in at least some embodiments, the peripheral may include a dust sensor 338. In some such embodiments, the sleep environment information may be determined based on dust readings from the dust sensor. In some embodiments, the sensors provided in the peripheral include a room humidity sensor 330 and the sleep environment information is determined based on humidity sensor readings obtained from the humidity sensor. In some embodiments, the sensors provided in the peripheral include a light sensor 336 and the sleep environment information is determined based on light readings obtained from the light sensor. In some embodiments, the sensors provided in the peripheral include a microphone 334 and the sleep environment information may be determined based on an audio signal generated by the microphone. In some embodiments, the sensors provided in the peripheral include a room temperature sensor 332 configured to detect the room temperature and the sleep environment information is determined based on a temperature reading obtained from the temperature sensor.

In some embodiments, the sleep environment information may be a score which is determined based on data from at least two different types of sensors provided in the peripheral. This score may be referred to as a sleep environment score and it may indicate the quality of environmental factors (such as sound, humidity, temperature, dust, etc.) in a room in which the mattress is located.

In some embodiments, after determining sleep environment information, the processor may store such information in memory.

At 1106, an output may be generated on an output interface based on the sleep environment information. The output interface may, for example, be a display associated with the sleep system or a mobile device. In at least some embodiments, the output may indicate the sleep environment information. For example, the output may indicate a humidity level, dust level, light level, sound level, and/or temperature level in the room.

In at least some embodiments, an alert may be generated based on the sleep environment information. For example, in at least some embodiments, one or more predetermined thresholds may be used to evaluate humidity levels, dust levels, light levels, sound levels, and/or temperature levels in the room. For example, a humidity level, dust level, light level, sound level and/or temperature level which is determined based on data from one or more sensors in the peripheral may be compared by the processor to one or more associated predetermined threshold. In at least some embodiments, the processor may generate an alert if a level exceeds associated threshold (or is less than the threshold, depending on the nature of the threshold). For example, if the room is not humid enough (i.e. if the humidity level is less than the associated threshold), an alert may be generated.

Mobile Device

As noted above, in at least some embodiments, a mobile device 1200 may connect to the sleep system using a wireless communication subsystem 370 provided on the sleep system 100. An example of one such mobile device 1200 will now be discussed with reference to FIG. 12. The mobile device 1200 is illustrated in block diagram form. The mobile device 1200 may, in some embodiments, be a smartphone. In other embodiments, the mobile device 1200 may be a tablet computer. The mobile device 1200 may take other forms in other embodiments.

The mobile device includes a controller which controls overall operation of the mobile device. In the example, this controller is provided by a main processor 1217. The main processor 1217 connects to various device subsystems such as, for example, a wireless communication subsystem 1270, a display 1290, an input interface 1282, a power source 1212, a camera 1280 and/or a memory 1272. It will be appreciated that the mobile device 1200 will include other components that are not specifically illustrated.

The wireless communication subsystem 1270 is used for connecting the mobile device to the sleep system 100. Once connected, the mobile device 1200 may send data to and receive data from the sleep system 100. More particularly, the wireless communication subsystem 1270 provides for communications between the main processor 1271 of the mobile device and the main processor 117 of the sleep system 100. The mobile device 1200 may, for example, receive mattress health information, sleep state information and/or sleep environment information from the sleep system 100. In some embodiments, raw sensor data may be received from the sleep system 100.

The display 1290 is an output interface which is used for outputting information from the mobile device. By way of example, in some embodiments, display screens may be generated on the display based on mattress health information, sleep state information and/or sleep environment information received from the sleep system 100.

The input interface 1282 is an input mechanism which allows a user to input instructions to the mobile device 1200. The input interface 1282 may take a variety of forms including input buttons or a touchscreen display.

The power source 1212 provides power to at least some of the electrical components of the mobile device 1200. By way of example, in some embodiments, the power source may be a battery.

In some embodiments, a camera 1280 may be provided on the mobile device 1200. The camera includes an image sensor which generates an electrical signal responsive to received light.

The processor 1217 is associated with memory 1272. The memory may store data and processor-executable instructions. The processor-executable instructions may include a mattress monitoring application 1290. The mattress monitoring application 1290 may include instructions which configure the main processor 1217 to perform one or more of the methods described herein or a portion thereof. More particularly, the mattress monitoring application 1290 may analyze, process, relay and/or report data obtained via the wireless communication subsystem 1270 from the sleep system 100.

Figure 15:
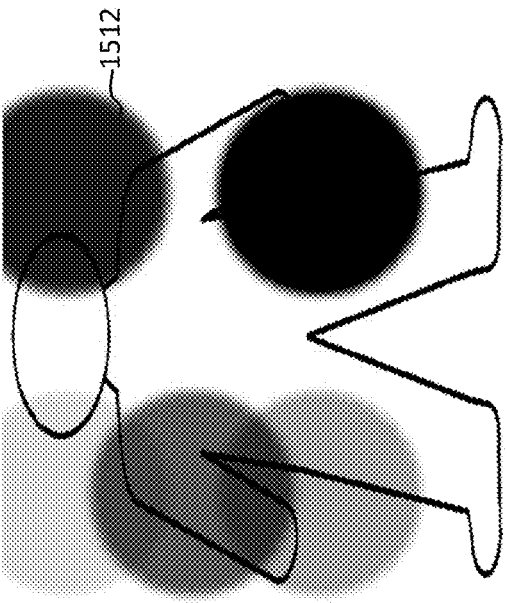
FIG. 15 is an example display screen.

In some embodiments, the mattress monitoring application 1290 may transmit a signal to a remote server based on the data obtained from the sleep system 100. For example, in some embodiments, the mobile device 1200 may be used as a conduit to transmit data (such as mattress health information, sleep state information, sleep environment information and/or raw sensor data) from the sleep system 100 to the remote server. The mobile device 1200 may transmit data that is received from the sleep system (i.e. it may receive the data at relay it to the server) or it may transmit data that is obtained at the mobile device 1200 based on the data received from the sleep system 100. In some embodiments, the mattress monitoring application 1290 may generate one or more display(s) based on the data obtained from the sleep system 100. For example, the mattress monitoring application may generate a display screen 1500 for display on the display 1290 which includes one or more sleep disorder indicators 1502 (FIG. 15) to indicate whether a user (who was an occupant of the sleep system 100 in the past and/or who has been registered on the mobile device 1200 as being with the sleep system 100) has one or more sleep disorders (see FIG. 15 for an example display). In some embodiments the sleep disorder indicator may indicate that a user has a sleep disorder, in some embodiments it may indicate that the user does not have a sleep disorder, in some embodiments it may indicate that a user is likely to have a sleep disorder, in some embodiments it may indicate that a user in unlikely to have a sleep disorder, and in some embodiment the sleep disorder indicator may quantify the likelihood of the user having a sleep disorder (i.e. it may display a likelihood score) The sleep disorders may include any of the sleep disorders described above including insomnia, narcolepsy, periodic limb movement disorder, DSPS, ASPS, sleep apnea, bruxism, sleep walking, sleep talking, and bedwetting. Any one or more of these sleep disorders may be detected by the mobile device 1200, by the sleep system 100 and/or by a server 1300 (FIG. 13) in the manner described above with reference to FIG. 9. In at least some embodiments, the display screens 1500 may provide access to one or more tips 1504 for dealing with and/or preventing one or more of these sleep disorders. In the example of FIG. 15, the tips 1504 are provided as a selectable interface element which may be activated by an input interface 1282 of the mobile device 1200 (e.g. a touchscreen display) to cause the processor of the mobile device 1200 to generate a display screen (not shown) which includes text describing the tip.

In at least some embodiments, the display screen 1500 (FIG. 15) may include one or more diagnostic report interface elements 1506 which may be activated by an input interface 182 of the mobile device 1200 to cause the processor to save, print, share (e.g. by email, social media such as Twitter™, on a social network such as Facebook™, etc.) a report based on information obtained from the sleep system 100. This report may, for example, specify whether the occupant has a sleep condition and/or may detail information derived from or based on data obtained from the sleep system's sensors. For example, the report may provide: information about when the occupant went to bed (i.e. entered the bed), fell asleep, woke up, got out of bed; information about the occupant's heart rate and/or breathing rate during one or more sleep sessions; information about any sleep apnea events detected during the night; information about the amount of movements of the occupant; information about any wakeups during the night; information about the various sleep stages such as the amount of time spent in each sleep stage and/or the times when the occupant entered and/or exited each sleep stage; and/or information about the time(s) when a user got out of bed during a sleep session (e.g. when they were sleepwalking). Other information may be included in other embodiments.

It will be appreciated that any of the display screens described below with reference to FIGS. 16 to 21 may include a diagnostic report interface element 1506 similar to what is described with reference to FIG. 15 and that the information contained in the report may depend on the page from which the report was generated. For example, the report may, as appropriate, contain: information about the occupant's sleep position(s); sleep environment information including information about room temperature, room humidity, room sound, room light and/or room air quality; mattress health information such as reminders about maintenance events, etc.

In some embodiments, the mattress monitoring application 1290 may generate a display screen 1500 (FIG. 15) which includes one or more sleep position indicators 1510, 1512. The sleep position indicator(s) are generated based on sleep position information. Techniques for determining sleep position information are described with reference to FIG. 8 and such techniques may be performed by the mobile device 1200, by the sleep system 100 and/or by a server 1300 (FIG. 13) prior to generating the display screen 1500. In the example of FIG. 15, a first sleep position indicator 1510 indicates the occupant/user's most common sleep position. A second sleep position indicator 1512 is a pressure map which visually indicates the frequency that the user sleeps on various areas of the mattress and/or the amount of force registered at various force sensors 120a-120h distributed on the mattress 101.

Figure 16:
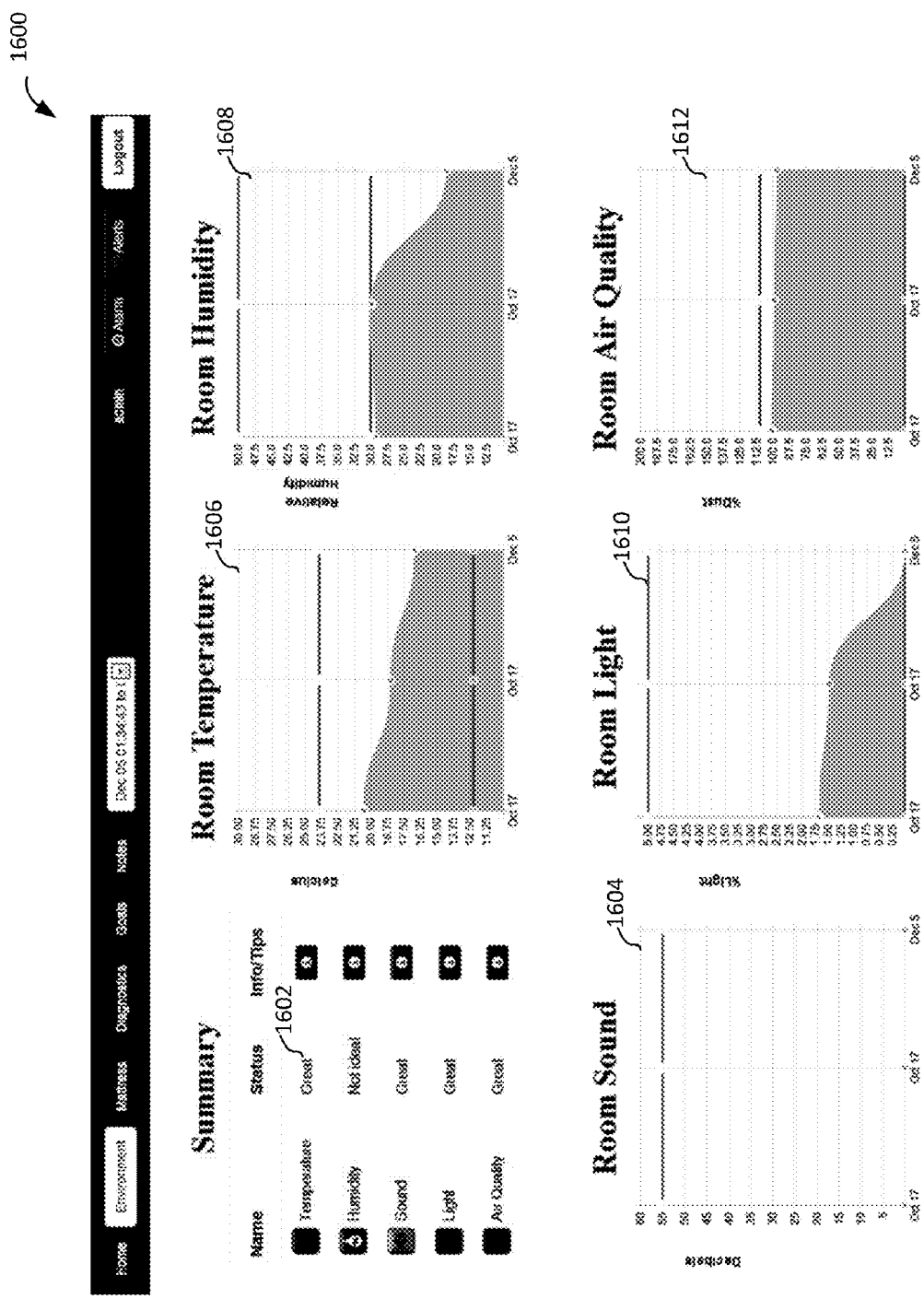
FIG. 16 is an example display screen.

Referring to FIG. 16, in some embodiments, the mattress monitoring application 1290 may generate a display screen 1600 which provides sleep environment information. More particularly, one or more sleep environment indicators 1602, 1604, 1606, 1608, 1610, 1612 may provide information about the sleep environment. In the example illustrated, a first sleep environment indicator 1602 provides an indication of a rank or scores one or more environmental factors. For example, in the example, illustrated, the first sleep environment indicators 1602 ranks the temperature in the room where the sleep system 100 is located. Other sleep environment indicators, which are not numbered in FIG. 16, rank the humidity, sound, light level and/or air quality in the room.

In the example, illustrated, each of these environmental factors (temperature, humidity, sound, light level and air quality) has an associated detailed sleep environment indicator 1604, 1606, 1608, 1610, 1612 which provides additional information about these environmental factors. For example, these detailed sleep environment indicators may graph the environmental factors over an extended period of time. In at least some embodiments, the mobile device 1600 (and/or the server 1300, as will be explained in greater detail below with reference to FIG. 13) generates one or more of these sleep environment indicators 1604, 1606, 1608, 1610, 1612 based only on data obtained while a sleep session was ongoing. That is, the sleep environment indicators may ignore data obtained while the occupant was not in bed and/or data obtained while the occupant was not asleep. Techniques for determining whether an occupant is in bed and/or asleep are described above. In some embodiments, data obtained during the daytime may be ignored and the sleep environment indicators may only be generated based on data obtained at night.

Figure 21:
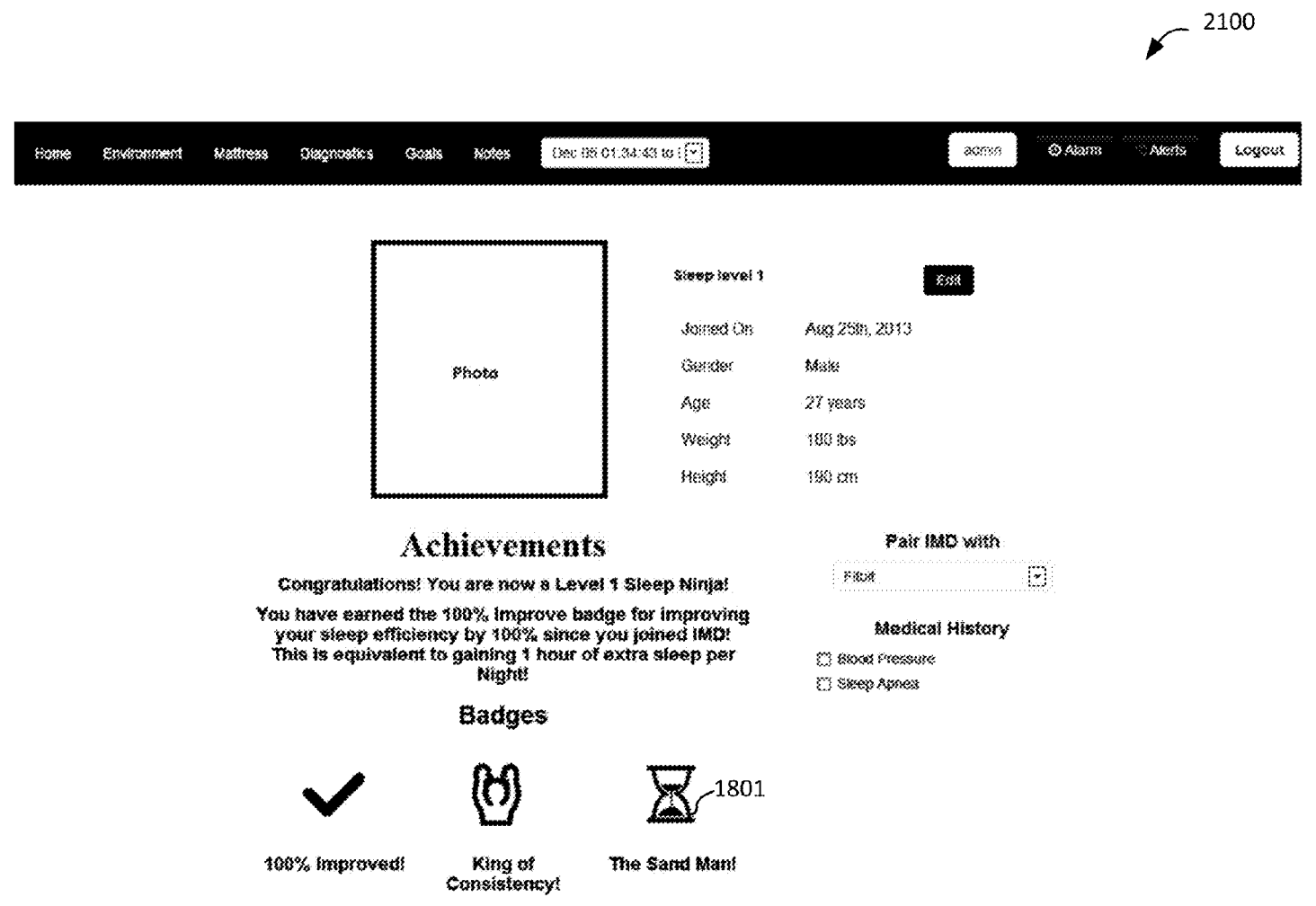

In some embodiments, the mattress monitoring application 1290 may include gamification features. Gamification features are features which set goals and/or which generate awards for a user/occupant. The gamification features are sleep-related and the awarding of awards is based on data obtained from the sleep system 100. Accordingly, in at least some embodiments, to implement the gamification features, the mattress monitoring application 1290 may cause the processor of the mobile device to determine whether predetermined sleep criteria associated with an award has been satisfied based on data obtained from the sleep system 100. If the sleep criteria associated with the award has been satisfied, then the processor may generate the award. In at least some embodiments, the award 1801 (FIGS. 18 and 21) is generated on a display screen 1800 (FIG. 18), 2100 (FIG. 21).

Figure 18:
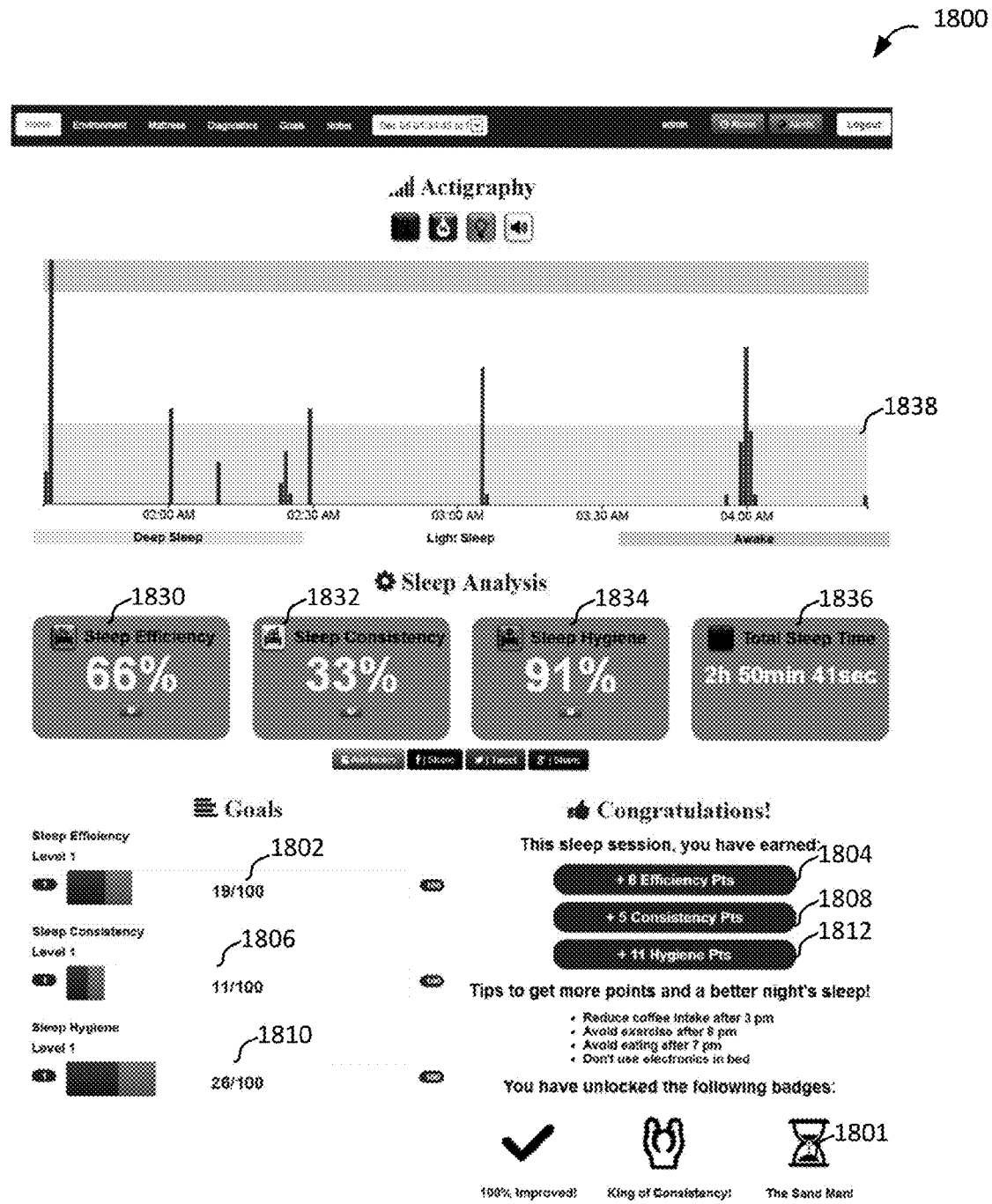
FIG. 18 is an example display screen.

As illustrated in FIG. 18 (and in the profile page of FIG. 21), the award 1801 may, for example, be in the form of a digital badge or trophy which may be displayed on a display screen displayed on the display of the mobile device.

The sleep criteria associated with an award may, for example, be based on any one or more of the following factors: the time when a user/occupant went to bed, the time when a user/occupant woke up, one or more scores such as a sleep score, a sleep environment score, a mattress health score, etc, one or more environmental factors such as the room temperature, room humidity, light level, air quality, and/or sound during a sleep session, whether a user attends to a maintenance event and/or the period of time elapsed between when a user was alerted regarding a maintenance event and when they indicated that the maintenance event was complied with. Other criteria may be used in other embodiments.

In at least some embodiments, a display screen 1700, 1800 may display an occupant/user's progress toward a goal, level, achievement and/or an award. For example, a display screen 1702 includes a plurality of progress indicators 1702, 1704, 1706 which indicate the user's progress towards one or more goals. In this example, a first progress indicator 1702 indicates progress towards achieving an increased sleep efficiency level. This progress indicator may be generated based on a sleep efficiency score, which is described in greater detail above. The sleep efficiency score for a sleep session may be determined by the sleep system 100, the mobile device 1200 and/or the server 1300 (FIG. 13) and may be added to a total sleep efficiency score that is stored in memory and which identifies the total sleep efficiency score for prior sleep sessions. In this way a new total sleep efficiency score is obtained, and the first progress indicator 1702 is based on this new total.

Figure 17:
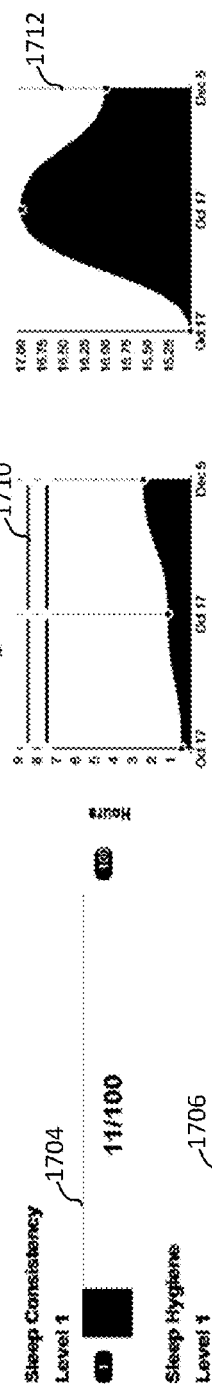
FIG. 17 is an example display screen.
Figure 17:
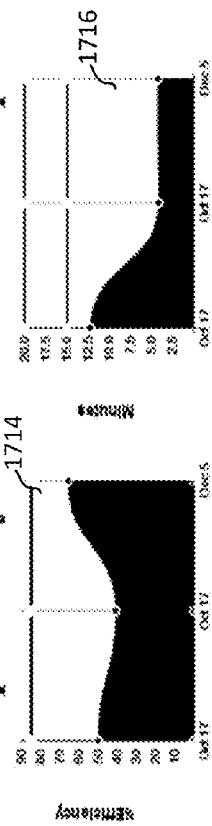
Figure 17:
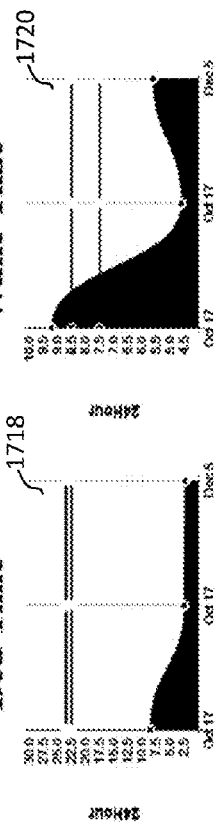

In the example of FIG. 17, a second progress indicator 1704 indicates the user's progress towards achieving an increased sleep consistency level. This progress indicator may be generated based on a sleep consistency score, which is described in greater detail above. The sleep consistency score for a sleep session may be determined by the sleep system 100, the mobile device 1200 and/or the server 1300 (FIG. 13) and may be added to a total sleep consistency score that is stored in memory and which identifies the total sleep consistency score for prior sleep sessions. In this way a new total sleep consistency score is obtained, and the second progress indicator 1704 is based on this new total.

In the example of FIG. 17, a third progress indicator 1706 indicates the user's progress towards achieving an increased sleep environment (aka hygiene) score. This progress indicator may be generated based on a sleep hygiene score, which is described in greater detail above. The sleep hygiene score for a sleep session may be determined by the sleep system 100, the mobile device 1200 and/or the server 1300 (FIG. 13) and may be added to a total sleep hygiene score that is stored in memory and which identifies the total sleep hygiene score for prior sleep sessions. In this way a new total sleep hygiene score is obtained, and the third progress indicator 1706 is based on this new total.

Referring now to FIG. 18, a further display screen 1802 is illustrated which also include progress indicators 1802, 1804, 1806, 1808, 1810, 1812. These additional progress indicators indicate the amount by which the user's progress towards a goal has changed during their most recent sleep session. In this example, first and second progress indicators 1802, 1804 illustrate the amount by which a user's sleep efficiency increased during the last sleep session. In the case of the first progress indicator 1802 this is indicated relative to the prior progress towards that goal (i.e. in sleep sessions prior to the most recent sleep session) and in the case of the second progress indicator 1804 the most recent progress is indicated in an absolute sense (i.e. not relative to the prior progress).

Similarly, third and fourth progress indicators 1806, 1808 may indicate recent progress towards achieving an increased sleep consistency level and fifth and sixth progress indicators 1810, 1812 may indicate recent progress towards achieving an increased sleep environment level.

Accordingly, mattress monitoring application 1290 may, in at least some embodiments, generate one or more display screens 1700, 1800 which provide feedback to the user about the gamification features referred to above.

In some embodiments, the mattress monitoring application 1290 may generate one or more display screens 1700, 1800 which include one or more of: a sleep time indicator 1710 (FIG. 17), 1836 (FIG. 18) indicating the amount of time that the user slept (this may indicate the sleep time for the last sleep session (as indicated by the sleep time indicator 1836 of FIG. 18) and/or over an extended period such as a plurality of consecutive sleep sessions (as indicated by the sleep time indicator 1710 of FIG. 17)), a number of times awakened indicator 1712 (FIG. 17) indicating the number of times that the user woke up (this may indicate the number of wakeups for the last sleep session and/or over an extended period such as a plurality of consecutive sleep sessions), a sleep efficiency indicator 1714 (FIG. 17), 1830 indicating the sleep efficiency score (this may indicate the sleep efficiency score for the last sleep session (as indicated by the sleep efficiency indicator 1830 of FIG. 18) and/or over an extended period such as a plurality of consecutive sleep sessions (as indicated by the sleep efficiency indicator 1714 of FIG. 17)), a sleep onset latency indicator 1716 (FIG. 17) which indicates the amount of time that it took a user to fall asleep (this may indicate the sleep onset latency for the last sleep session and/or over an extended period such as a plurality of consecutive sleep sessions), a bed time indicator 1718 (FIG. 17) indicating the time at which an occupant went to bed (this may indicate the bed time for the last sleep session and/or over an extended period such as a plurality of consecutive sleep sessions), a wake time indicator 1720 (FIG. 17) indicating the time at which an occupant woke up (this may indicate the wakeup time for the last sleep session and/or over an extended period such as a plurality of consecutive sleep sessions), a sleep consistency indicator 1832 (FIG. 18) indicating a sleep consistency score (this may indicate the sleep consistency for the last sleep session and/or over an extended period such as a plurality of consecutive sleep sessions), a sleep environment (a.k.a. hygiene) indicator 1834 indicating a sleep environment score (this may indicate the sleep environment score for the last sleep session and/or over an extended period such as a plurality of consecutive sleep sessions), a heart rate indicator (not shown) which may indicate information about the occupants heart rate for the last sleep session or over an extended period of time, a respiratory rate indicator (not shown) indicating information about the occupant's respiration rate during the last sleep session and/or over an extended period of time, and/or a sleep stage indicator 1838 which may indicate the times at which an occupant entered and/or exited sleep stages. Other types of information that is described in the detailed description above which is determined based on information obtained from sensors associated with the sleep system may also be included on display screens in other embodiments.

Techniques for determining the various information represented by the various indicators referred to above are described above and these techniques may be performed by the mobile device 1200, sleep system 100 and/or server 1300 (FIG. 13) using data obtained from the sleep system.

In some embodiments, the mattress monitoring application 1290 may generate one or more display screens 1900 based on mattress health information. Techniques for determining mattress health information are described above (e.g. with reference to FIG. 10) and these techniques may be performed by the mobile device 1200, sleep system 100 and/or server 1300 (FIG. 13) using data obtained from the sleep system.

In at least some embodiments, the display screen 1900 may include one or more alerts 1902, 1904, 1906 that are triggered based on the mattress health information. These alerts 1902, 1904, 1906 may be generated in the manner described above with reference to 104 of FIG. 10 and may, for example, indicate whether a maintenance event is required. In the example illustrated, the display includes a visual alert 1902 informing the user that it is time to change the bedding, a visual alert 1904 informing the user that it is time to refresh the mattress 1904 (which may indicate that the mattress should be deodorized and/or disinfected) and a visual alert 1906 informs the user that it is time to rotate and/or flip their mattress. In some embodiments, one or more indicator may project an expected date when a maintenance event is required.

In some embodiments, a display screen 1900 may display other information about the mattress health. For example, usage-since-maintenance information may be displayed and/or lifetime-usage information may be displayed. By way of example, a total usage indicator 1920 is provided on the display screen 1900 of FIG. 19 to indicate the lifetime-usage information. The display screens that are generated may, in some embodiments, include one or more display screens 2000 (FIG. 20) which provide interface elements for inputting information associated with a user profile and/or user feedback regarding a sleep session. As noted above, user profile information may, in some embodiments, be used for determining a risk level associated with one or more sleep disorders (e.g. sleep apnea). In some such embodiments, a display screen 2000 may be generated by the mattress monitoring application 1290 to allow a user to input information about the user and/or a sleep session. By way of example, the display screen 2000 of FIG. 20 allows a user to input information relevant to a recent sleep session. This information may include, for example, an overall rating of the sleep session (as determined by the user), an indication of whether the user consumed alcohol, exercised late, consumed caffeine, consumed food late at night, was on medication, watched television before bed, used their mobile device immediately before bed, felt stressed, uses a continuous positive airway pressure (CPAC) device, etc. In at least some embodiments, the mattress monitoring application 1290 may cause the processor to correlate such information with nights where the occupant had poor sleep quality (as reflected by the sleep quality score) and/or when the occupant suffered from a sleep disorder. In at least some embodiments, when the results of the correlation suggest that there is a connection between one of the inputted factors and the poor sleep quality or sleep disorder, an alert may be generated (e.g. on a display of the mobile device 1200). This alert may, in at least some embodiments, be in the form of a suggestion or tip which suggests the user eliminate or reduce the factor which may have a causal link to the poor sleep quality or the sleep disorder.

In at least some embodiments, the mattress monitoring application 1290 may generate one or more display screens 2100 (FIG. 21) which display information associated with a user profile, such as a gender, age, weight, height, name, photograph, etc. associated with a user/occupant.

While the description immediately above has described an embodiment in which the mattress monitoring application 1290 associated with the mobile device 1200 generated the display screens 1500, 1600, 1700, 1800, 1900, 2000, 2100, in other embodiments, one or more of these display screens may be generated by a web server 1300 (FIG. 13) which sends such display screens (e.g. in the form of Hyper Text Markup Language (HTML) documents or other web-standard documents) to the mobile device 1200. An Internet browser application which resides in memory on the mobile device 1200 may receive such display screens 1500, 1600, 1700, 1800, 1900, 2000, 2100 and update the display 1290 accordingly. Such embodiments will be described below with reference to FIG. 13. While a single memory is illustrated, in practice the mobile device 1200 includes a plurality of memory components of various types.

In at least some embodiments, a code reader application 1292 may be provided in memory of the mobile device 1200. The code reader application 1292 includes processor-executable instructions which configure the main processor 1217 to scan a machine-readable code, such as a QR code and/or a wireless tag such as an NFC tag or RFID tag (in which case the mobile device may include a short range communication subsystem such as an NFC subsystem). For example, the code reader application 1292 may cause the camera 1280 to obtain an image of a code 180*a*, 180*b* (FIG. 1) and to decode information contained in that code. In some embodiments, the code reader application may wirelessly receive the code 180*a*, 180*b* from a nearby wireless tag, such as an NFC tag, and may decode information contained in the received code.

As noted in the discussion of FIG. 1 above, in some embodiments, one or more machine readable codes 180*a*, 180b may be provided on the mattress 101. In at least some such embodiments, the information contained in the code may specify a location at which the mattress monitoring application 1290 may be downloaded, unique identifying information for the mattress and/or information which identifies one of the portions 112, 114 of the mattress.

Where the code specifies a location at which the mattress monitoring application 1290 may be downloaded, the code reader application 1292 may be configured to cause the processor 1217 to automatically download and/or install the mattress monitoring application 1290 to the mobile device 1200.

Where the code specifies unique identifying information for the mattress, the code reader application 1292 and/or the mattress monitoring application 1290 may use this information to register the mattress in a user profile for a user of the mobile device. This user profile may be stored locally on the mobile device or may be located on a remote server.

Where the code identifies a specific side of the mattress, the code reader application 1292 and/or the mattress monitoring application 1290 may use this information to register the side of the mattress in a user profile for a user of the mobile device. As noted in the discussion of FIG. 1 above, in some embodiments, both portions 112, 114 of the mattress may include two machine-readable codes 180a, 180b which may be used to associate a mobile device with a specific side of the mattress. Each of these machine-readable codes is associated with a separate portion 112, 114 of the mattress 101. For example, a first code 180a may be located at a left portion 112 of the mattress and associated with the left portion 112 and a second code 180b may be located at a right portion 114 of the mattress and associated with the right portion 114. A user of a mobile device 1200 (FIG. 12) may use the camera 1280 to scan the code 180a, 180b. The codes 180a, 180b uniquely identify the mattress from other mattresses, and each of the codes uniquely identifies the side of the mattress associated with that code. For example, the first code 180a may identify the left side and the second code 180b may identify the right side.

In such embodiments, the code 180a, 180b may be used by the mobile device to associate the mobile device 1200 with a specific side of the mattress. That is, an occupant who sleeps on the left side may scan the code 180a associated with the left side. In at least some embodiments, by doing so the mattress monitoring application 1290 will then be automatically configured to obtain and/or display information obtained from the sleep system about the left side of the mattress. For example, sleep state information and/or raw data generated from a first sensor set 150 located at the left side may be retrieved by the mobile device which has scanned the code 180a on the left side, but sleep state information and/or raw data generated from the second sensor set 152 located at the right side may not be retrieved by the mobile device which has scanned the code 180a on the left side. Accordingly, in at least some embodiments, a mobile device 1200 may only retrieve and/or display information associated with a side of the bed for which it has scanned the associated code 180a, 180b.

The mobile device 1200 may include a number of components that are not illustrated in FIG. 12. By way of example, the mobile device 1200 could include a number of sensors. In at least some embodiments, data obtained from the sensors in the mobile device 1200 may be used in conjunction with data obtained from the sensors embedded into the sleep system 100. For example, one or more of the sensors in the sleeping environment sensing array 306 (FIG. 3) may be provided on the mobile device 1200.

Server

Referring now to FIG. 13, an example server 1300 is illustrated in block diagram form. The server 1300 is, in at least some embodiments, a web server which may be configured to host a website. The web server is, in at least some embodiments, configured to generate one or more display screens, such as the display screen(s) 1500, 1600, 1700, 1800, 1900, 2000, 2100 of FIGS. 15 to 16.

The server 1300 includes a controller which controls overall operation of the server 1300. In the example, this controller is provided by a main processor 1317. The main processor 1317 connects to various device subsystems such as, for example, a communication subsystem 1370, an input interface (not shown), a power source (not shown), and/or a memory 1372. It will be appreciated that the server 1300 will include other components that are not specifically illustrated.

The communication subsystem(s) 1370 are used for connecting the mobile device to other systems, servers and/or devices, such as the sleep system 100, the mobile device 1200 and/or another client device such as a computer. More particularly, in at least some embodiments, the communication subsystem(s) 370 may allow the server 1300 to receive data from the sleep system 100. Such data may include, for example, mattress health information, sleep state information and/or sleep environment information. In some embodiments, raw sensor data may be received from the sleep system 100. Such data may, in some embodiments, be sent from the sleep system 100 to the server 1300 using a mobile device 1200 as a conduit. In other embodiments, the mobile device 1200 may not be used as a conduit and the data may be sent directly from the sleep system 100 to the server 1300.

As noted above, in at least some embodiments, the server 1300 is a web server which is configured to generate display screens in the form of web pages which may be provided to other devices, such as the mobile device 1200 of FIG. 12 or a client device of another type, such as a computer. The web pages may be displayed via an Internet browser associated with such devices.

Accordingly, in at least some embodiments, the server 1300 has a mattress monitoring and/or reporting web application 1390 stored in memory 1372. This application 1390 is, in at least some embodiments, configured to analyze data received from the sleep system. More particularly, this application may be configured to cause the processor 1317 to perform any one or more of the methods described herein to obtain information based on data obtained from sensors embedded into the sleep system 100. For example, in some embodiments, the processor may obtain movement information in the manner described with reference to FIG. 4. In some embodiments, the processor may determine a sleep stage and/or whether an occupant is awake and/or a sleep onset or offset latency in the manner described with reference to FIG. 5. In some embodiments, the processor may determine a heart rate in the manner described with reference to FIG. 6 and in some embodiments a respiration rate is determined in the manner described with reference to FIG. 7. Sleep position may, in some embodiments, be determined in the manner described above with reference to FIG. 8. In some embodiments, a sleep disorder may be detected by the processor 1317 in the manner described with reference to FIG. 9 and in some embodiments, mattress health information is determined in the manner described above with reference to FIG. 10. In some embodiments, sleep environment information is determined by the processor 1317 using techniques described with reference to FIG. 11.

Accordingly, in at least some embodiments, the server 1300 may determine at least some of the information described above. In some embodiments, the server 1300 may not, itself, determine at least some of this information but may instead be provided with this information by the sleep system 100.

In at least some embodiments, the server 1300 may generate one or more web pages based on information obtained from the sleep system 100. These display screens may be of the type described above with reference to the mobile device 1200 of FIG. 12. That is, instead of relying on a mattress monitoring application on the mobile device 1200 to generate these display screens 1500, 1600, 1700, 1800, 1900, 2000, 2100, these display screens may instead be generated by the web server (i.e. by the processor 1317 executing the mattress monitoring and/or reporting web application 1390) and provided to a client device such as the mobile device 1200 for display via a web browser or for display via a mobile application. Thus, any one or more of the display screens of FIGS. 15 to 21 may be generated by the server 1300.

Generating Display Screen(s)

Figure 14:
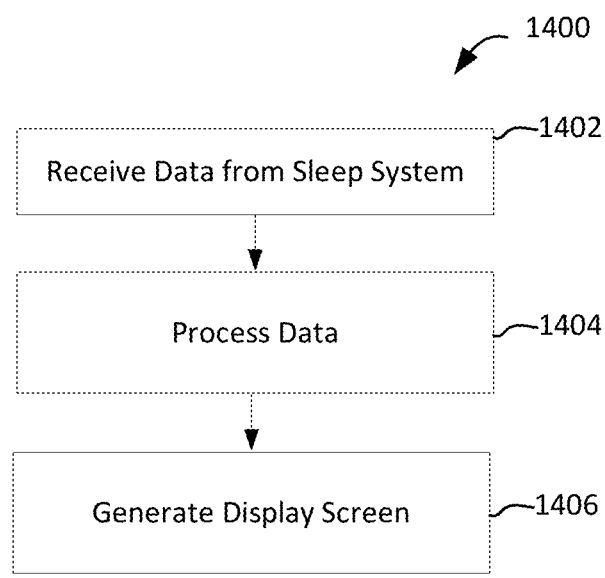
FIG. 14 is an example flowchart of a method for generating a display screen in accordance with example embodiments of the present disclosure.

Referring now to FIG. 14, an example method 1400 of generating a display screen 1500, 1600, 1700, 1800, 1900, 2000, 2100 is illustrated in flowchart form. The method 1400 may be performed by a processor associated with the mobile device 1200 (FIG. 12) or server 1300 (FIG. 13). More particularly, computer-executable instructions such as a mattress monitoring/reporting web application 1390 (FIG. 13) and/or a mattress monitoring application 1290 (FIG. 12), may configure an associated processor to perform the method 1400.

At 1402, data from the sleep system 100 is received from the sleep system via a communication subsystem 1270, 1370. The received data may be raw data (e.g. sensor samples) from the sleep system 100 sensors or it may be data which was previously processed, such as mattress health information, sleep state information and/or sleep environment information.

Optionally, in some embodiments, at 1404 the received data may be processed. The nature of this processing may depend on the form that the data is received in (e.g. whether processing has already been performed on the data by another system such as the sleep system 100). For example, where raw data is received or where data is received that has not been fully processed, processing may be performed to determine information included in the display screen(s) 1500, 1600, 1700, 1800, 1900, 2000, 2100.

Then, at 1406, a display screen 1500, 1600, 1700, 1800, 1900, 2000, 2100 is generated based on either the received data or the processed data. These display screens may be of the type described above with reference to FIG. 12 and FIGS. 15 to 21.

While the embodiments described herein have generally referred to embodiments in which sensors are embedded in a mattress, in other embodiments, a mattress sheet or sock could be used to retrofit a traditional mattress with the components described herein. For example, the force sensors 120a-120h, temperature sensor 122 and/or humidity sensor 124 of FIG. 1 could instead be affixed to a mattress sheet or a sock which is configured to be applied to a mattress.

Furthermore, in at least some embodiments, at least some of the sleep monitoring functions described above may be performed automatically. That is, the sleep system 100 may perform background processes which monitor for an occupant's presence. Thus, a user may not have to actively turn the sleep system on or off.

The various embodiments presented above are merely examples. Variations of the innovations described herein will be apparent to persons of ordinary skill in the art, such variations being within the intended scope of the present application. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A sleep system comprising:
one or more occupant-monitoring sensors associated with a mattress;
an output interface;
one or more processors coupled with the one or more sensors and the output interface; and
a memory coupled with the at least one processor,
at least one of the processors being configured to:
determine mattress health information based on data obtained from one or more of the sensors, wherein determining mattress health information comprises quantifying mattress usage based on data from the occupant-monitoring sensors; and
generate an alert via the output interface based on the mattress health information, the alert prompting a user to perform one or more of: flipping the mattress, rotating the mattress, changing bedding on the mattress, deodorizing the mattress, disinfecting the mattress or vacuuming the mattress.

2. The sleep system of claim 1, wherein the occupant-monitoring sensors include one or more force sensors that are positioned within the mattress to sense presence of an occupant of the mattress and wherein mattress usage is quantified based on data from one or more of the force sensors.

3. The sleep system of claim 2, wherein the at least one processor is further configured to determine that mattress maintenance is required based on the quantified mattress usage.

4. The sleep system of claim 3, wherein the at least one processor is configured to output the alert via the output interface in response to determining that mattress maintenance is required.

5. The sleep system of claim 4, wherein the alert is a displayed message prompting a user to flip or rotate the mattress.

6. The sleep system of claim 5, wherein the occupant-monitoring sensors include a plurality of force sensors embedded into the mattress and wherein the plurality of force sensors associated with a top side of the mattress are arranged to have second order rotational symmetry.

7. The sleep system of claim 5, wherein at least some of the occupant-monitoring sensors are associated with a top side of the mattress and at least some of the occupant-monitoring sensors are associated with a bottom side of the mattress and wherein the arrangement of the occupant-monitoring sensors on the top side is the same as the arrangement of the occupant-monitoring sensors on the bottom side.

8. The sleep system of claim 4, wherein the alert is a displayed message prompting a user to change bedding.

9. The sleep system of claim 4, wherein the alert is a displayed message prompting a user to deodorize the mattress, disinfect the mattress or vacuum the mattress.

10. The sleep system of claim 1, wherein the memory stores usage-since-maintenance information, the usage-since-maintenance information indicating usage of the mattress since a last maintenance event of a predetermined type, and wherein the at least one processor is configured to:
    detect that the mattress is in use;
    detect that the mattress is no longer in use;
    determine an amount of time elapsed between when the mattress was detected to be in use and when the mattress was detected to be no longer in use;
    determine new usage-since-maintenance information by adding the amount of time elapsed to the usage-since-maintenance information stored in memory; and
    update the memory to store the new usage-since-maintenance information.

11. The sleep system of claim 10, wherein the processor is further configured to compare the usage-since-maintenance information to a predetermined threshold, and wherein the alert is generated, by the processor, in response to determining that usage-since-maintenance information exceeds the predetermined threshold.

12. The sleep system of claim 11, wherein the processor is configured to reset the usage-since maintenance information in response to detecting one or more predetermined reset conditions.

13. The sleep system of claim 12, further comprising an input interface for receiving input from a user, and wherein the one or more predetermined reset conditions include an instruction to reset the usage-since-maintenance information, the instruction received via the input interface.

14. The sleep system of claim 1, wherein the processor is configured to separately track usage associated with each of two sides of the mattress, and wherein the memory stores first usage-since-maintenance information indicating total usage of a first portion of the mattress since a last maintenance event and second usage-since-maintenance information indicating total usage of a second portion of the mattress since the last maintenance event, and wherein the processor is configured to modify the first usage-since-maintenance information based on detected usage of the first portion of the mattress and to modify the second usage-since-maintenance information based on detected usage of the second portion of the mattress, and wherein the processor is configured to compare both the first usage-since-maintenance information and the second usage-since-maintenance information to a predetermined threshold and to generate the alert in response to determining that any one or both of the first usage-since-maintenance information and the second usage-since-maintenance information exceed the predetermined threshold.

15. The sleep system of claim 1, wherein the memory stores lifetime-usage information, the lifetime-usage information indicating total usage of the mattress since manufacture, and wherein the at least one processor is configured to:
    detect that the mattress is in use;
    detect that the mattress is no longer in use;
    determine an amount of time elapsed between when the mattress was detected to be in use and when the mattress was detected to be no longer in use;
    determine new lifetime-usage information by adding the amount of time elapsed to the lifetime-usage information stored in memory; and
    update the memory to store the new lifetime-usage information.

16. The method of claim 15, wherein the lifetime-usage information is never reset.

17. The method of claim 15, wherein the at least one processor is further configured to compare the lifetime-usage information to a predetermined threshold, and wherein the alert is generated, by the processor, in response to determining that lifetime-usage information exceeds the predetermined threshold.

18. The sleep system of claim 1, wherein the one or more occupant-monitory sensors include a humidity sensor, and wherein the at least one processor is configured to generate the alert based on data obtained from the humidity sensor.

19. The sleep system of claim 18 wherein the at least one processor is configured to generate the alert if a humidity level obtained from the humidity sensor exceeds a threshold for at least a predetermined period of time.

20. The sleep system of claim 1, wherein the output interface is provided on a mobile device.

* * * * *